US008032397B2

(12) United States Patent
Lawless

(10) Patent No.: US 8,032,397 B2
(45) Date of Patent: Oct. 4, 2011

(54) INTEGRATED PRESCRIPTION MANAGEMENT AND COMPLIANCE SYSTEM

(76) Inventor: Oliver Charles Lawless, Highland, MD (US)

( * ) Notice: Subject to any disclaimer, the term of this patent is extended or adjusted under 35 U.S.C. 154(b) by 1205 days.

(21) Appl. No.: 11/624,293

(22) Filed: Jan. 18, 2007

(65) Prior Publication Data

US 2007/0168228 A1 Jul. 19, 2007

Related U.S. Application Data

(60) Provisional application No. 60/759,962, filed on Jan. 19, 2006.

(51) Int. Cl.
*G06Q 50/00* (2006.01)
(52) U.S. Cl. .................................... 705/3; 705/2
(58) Field of Classification Search ................... 705/2–3
See application file for complete search history.

(56) References Cited

U.S. PATENT DOCUMENTS

| | | | | |
|---|---|---|---|---|
| 5,623,242 | A * | 4/1997 | Dawson et al. | 340/7.3 |
| 2002/0022973 | A1* | 2/2002 | Sun et al. | 705/3 |
| 2002/0068551 | A1* | 6/2002 | Strunk et al. | 455/414 |
| 2003/0009355 | A1* | 1/2003 | Gupta | 705/2 |
| 2004/0002872 | A1* | 1/2004 | Wright | 705/2 |
| 2006/0064327 | A1* | 3/2006 | Simon et al. | 705/3 |

* cited by examiner

*Primary Examiner* — Gerald J. O'Connor
*Assistant Examiner* — Sind Phongsvirajati

(57) ABSTRACT

A system and method for prescription therapy management and compliance are provided. The system framework integrates primary databases from pharmacies, pharmacy benefit managers (PBMs), health plans, and EHR providers with a secondary database system, user interface, and wireless messaging platform, in order to extract and aggregate user-specific prescription data and make it available to users through a personalized account and as a part of a wireless prescription reminder service. The system helps users access, aggregate, manage, update, automate, and schedule the prescriptions they are currently taking. Users receive real-time wireless prescription dosing reminders based on their prescribed drug, dosage, and other indications, tailored to each individual's daily schedule. These wireless dosing reminders (i) include additional instructional content such as pill images, compliance tools, and Web or WAP drug links, (ii) are automatically scheduled and transmitted based on the user's prescription source data, in conjunction with selections indicated on their personal account, and (iii) are transmitted via SMS, EMS, MMS, WAP, email, and other formats to the user's mobile phone, PDA, or other wireless device. The integrated interface and secondary database system enable a number of additional system features which focus on compliance and management of the underlying source prescription data.

64 Claims, 11 Drawing Sheets

> Dear Mr. Smith,
> It is now 2:00 pm.
> Please take 20 mg of Lipitor
> (Atorvastatin calcium) with a glass of water.
> Thank you.

FIGURE 9A

> Dear Mr. Smith,
> It is now 2:00 pm.
> Please take 20 mg of Lipitor
> (Atorvastatin calcium) with a glass of water.
> Thank you.
>
> 

FIGURE 9B

> Dear Mr. Smith,
> It is now 2:00 pm.
> Please take 20 mg of Lipitor
> (Atorvastatin calcium) with a glass of water.
> For further instructions for this medication,
> please visit http://www.[   ].com
> Thank you.

FIGURE 9C

> Dear Mr. Smith,
> It is now 2:00 pm.
> Please take 20 mg of Lipitor
> (Atorvastatin calcium) with a glass of water.
> Thank you.
>
> 

FIGURE 9D

Dear Mr. Smith,
It is now 2:00 pm.
Please take 20 mg of Lipitor
(Atorvastatin calcium) with a glass of water.
Thank you.

Dear Mr. Smith,
It is now 2:00 pm.
Please take 20 mg of Lipitor
(Atorvastatin calcium) with a glass of water.
Thank you.

Lipitor - $4.80
(Atorvastatin 20mg)
SAVE 80%

Generic Lipitor - $99¢
(Atorvastatin 20mg)

INTEGRATED PRESCRIPTION MANAGEMENT AND COMPLIANCE SYSTEM

The present application claims priority under 35 U.S.C. §1119 to U.S. Provisional Application No. 60/759,962, filed Jan. 19, 2006, the entire disclosure of which is herein expressly incorporated by reference.

FIELD OF THE INVENTION

The present invention relates to the field of prescription therapy management and compliance, as well as wireless and database technology.

BACKGROUND OF THE INVENTION

Prescription drug therapy is now a standard component of most medical treatments. The volume and growth of prescription drug consumption has increased at record rates over the past decade. The primary drivers for this growth have been (i) an increase in drug usage due to an increasing number of chronic conditions and preventative treatments, (ii) advances in technology and newer drugs, (iii) accelerated FDA drug approvals, (iv) an aging population with a higher consumption rate, and (v) increased insurance and prescription drug coverage.

Once only an elderly or infirm phenomenon, prescription drugs are now being consumed on a regular basis by all age groups. Several chronic conditions and preventative treatments for each age group have made high per capita consumption rates the norm for a majority of Americans. In 2003, 3.4 billion prescriptions were dispensed in the United States, with an average per capita consumption rate of 11.8 prescriptions per person. By 2005, IMS Health reported that this number had grown to 15.4 prescriptions per person. In a recent survey by the Kaiser Family Foundation, 91% of Americans reported that they take prescription drugs, and more than half said they take prescription drugs regularly.

Despite numerous advances in modern medicine, prescription compliance remains a problem which continues to plague the healthcare industry. A study by the Kaiser Family Foundation has shown that over 70% of Americans either forget to take their medications or don't take them at the right times. There are multiple reasons for this phenomenon including: busy schedules with multiple demands, forgetfulness, an increasingly mobile culture, overestimation of negative side effects, and the cost of the drugs themselves. The most obvious reason may be that people don't seem to remember to take their medications when they don't feel sick.

This failure to comply with prescribed drug treatments results in ineffective drug treatments, hospitalizations, and emergency room visits, which in turn leads to increased health care costs for consumers, insurance companies, and the U.S. government. Prescription drug non-compliance costs society nearly $100 billion a year and leads to an estimated 125,000 deaths, according to statistics cited by the Department of Health and Human Services.

One of the biggest reasons for prescription non-compliance is the lack of interaction between patients and health care providers after drugs are dispensed and patients commence their prescription treatments. A prescription received by a pharmacy may come complete with drug name, dosage, dosing, and indications, but it does not associate dosing with specific times of the day, events, or in relation to other drugs consumed. It is left to the patient to adapt the prescription to his or her daily schedule, manage multiple prescriptions, remember each set of instructions at precise times of the day, and adapt their treatment regimens as new prescriptions are added or terminated. This process becomes much more complicated when patients are prescribed multiple drugs with different dosing regimens such as (i) once in the morning, (ii) every eight hours, (iii) three times a day, (iv) with meals, and (v) to be taken with drug X. Although the instructions and indications are printed on the container, they may be forgotten over the course of weeks and months. In addition, certain patients simply be incapable of adhering to a particular routine or regimen, and require personal compliance assistance from an individual such as a mother, spouse, sibling, or other caregiver. In these cases, those additional individuals need real-time access to the user's prescription instructions in order to assist them in taking their medications. Lastly, in cases where users sustain adverse reactions to a prescription dose taken, the user's prescription source data, used in conjunction with a real-time notification system, may be a critical step in getting the user timely, targeted health care support or emergency medical care.

There is currently a huge need for a system cheap and easy enough for the average consumer to use which can help users manage their prescription therapies and increase their rate of prescription compliance. Online, wireless, and other technologies which have high rates of consumer penetration are now routinely being used in numerous applications. U.S. wireless penetration currently exceeds 65%, and a majority of Americans use mobile phones throughout the day for business and personal use. Wireless data technologies such as wireless short message service (SMS), enhanced message service (EMS), multi-media message service (MMS), wireless application protocol (WAP), binary runtime environment for wireless (BREW), session initiation protocol (SIP), and instant messaging (IM) make efficient use of a wireless carrier's network and are available to all mobile phone users with a basic handset.

The present invention outlines a prescription therapy management and compliance system which uses standard technologies available to all consumers. Several health care entities such as pharmacies, pharmacy benefit managers (PBMs), health insurance companies or health plans, and electronic health record (EHR) providers maintain primary databases which store user-specific prescription information and HIPAA Protected Health Information (PHI). Although important, this information on its own is of no use from a drug management or compliance perspective. The proposed invention aggregates, customizes, formats, and otherwise uses the data stored on these primary databases in order to provide users with a real-time prescription management account, wireless dosing reminders, and other compliance features using standard technologies such as mobile phones and wireless devices. The use of accessible consumer technologies makes it easy for the average consumer to incorporate the system into their daily routine, thereby achieving the system's end goals of enhancing prescription therapy management and increasing prescription compliance.

DESCRIPTION OF THE PRIOR ART

Prescription compliance has been a problem for decades, and a number of patents have been issued for inventions designed to assist individuals comply with their prescription drug regimens. There are four categories of designs for compliance-based inventions. These are: (i) compliance devices affixed to drug containers, (ii) portable compliance devices, (iii) drug dispensers with compliance enhancements, and (iv) compliance communications systems.

The first category, compliance devices affixed to drug containers, are inventions designed to provide medication reminders which accompany the associated prescription medication. U.S. Pat. No. 6,545,592 "Medication reminder device" issued to Weiner, describes a removal prescription vial cap with an embedded electronic unit which generates an alarm alerting the user that it is time to take a dose of his or her medication. U.S. Pat. No. 7,017,762 "Medication reminder system" issued to Shane, describes a cap or closure for medication bottles which provide indicators for different drugs dispensed by a pharmacist.

The significant limitations of this class of inventions are that they must be manually programmed, cannot be separated from the drug containers, making them cumbersome and impractical for a mobile user, require a separate container for each drug taken by the user, and must be replaced with each refill or new drug, making them expensive and somewhat difficult to use.

The second category, portable compliance devices, are inventions designed to remind mobile users when to take their medications by generating alarms which notify the user that it is time to take that medication. U.S. Pat. No. 5,157,640 "Medication alert watch and system" issued to Backner, describes a watch worn by the user which must be programmed either electronically or by a pharmacist, and omits an audible alarm and an LCD display with the name and dosage of the programmed medication, alerting the wearer that it is time to take said medication. U.S. Pat. No. 6,934,220 "Portable programmable medical alert device" issued to Cruitt, Chan, and Tichy, describes a portable medical alert device, which may be programmed to emit an audible and visual alarm at certain times, reminding the user of their medication schedule, medical procedure, or other treatment.

The significant limitations of this class of inventions are that must be manually programmed and re-programmed for each new drug, require the user to carry a device which he or she would not normally carry, are only available to the immediate user, lack features such as compliance analysis, and are expensive and somewhat difficult to use.

The third category, drug dispensers with compliance enhancements, are systems designed to store, manage, and monitor prescription drug regimens for individuals through the use of interactive drug dispensers. U.S. Pat. No. 6,330,957 "Automatic medication dispenser" issued to Bell-Greenstreet, describes a medication dispenser which distributes medication and activates appropriate alarms according to at least one prescribed time schedule. U.S. Pat. No. 4,768,176 "Apparatus for alerting a patient to take medication" issued to Kehr and Hedrich, describes a container having four compartments which store medications and alert the user via signals indicating what medication in what quantity should be taken from what container and any instruction for taking that medication.

The significant limitations of this class of inventions are that they are not mobile and only work at the location in question, making them ineffective for mobile users requiring doses taken at different locations throughout the day. In addition, they must be manually programmed, lack features such as compliance analysis, and are expensive and somewhat difficult to use.

The fourth category of prescription compliance inventions are compliance communications systems, which are designed to alert the user of medications to be taken. U.S. Pat. No. 5,850,344 "Medication dispensing and timing system" issued to Conkright, describes a system whereby a central monitoring computer sends medication prompts in accordance with a drug regimen over a two-way paging system to a communicator carried by a patient. U.S. Pat. No. 5,872,505 "Medication alert pager and paging system" issued to Wicks and Sciammarella, describes a system to assist a patient with treatment reminders whereby patient treatment data is maintained in a database by a paging systems provider and then transmitted to a pager carried by a medical practitioner to remind him or her to administer the treatment in question to the patient.

The significant limitations of this class of inventions are that these systems are not fully updated and automated, do not aggregate or compile source data from a variety of data sources, require an individual to program or transmit the relevant data, lack the ability to analyze compliance, lack features allowing users to customize and schedule their drug treatments, and do not allow the addition of over-the-counter drugs, vitamins, or other alternative therapies to their notifications. In addition, they do not have the capability for enhanced message content such as pill images, Internet or WAP links with additional instructions, and reply options, and are not designed for use with intelligent mobile devices such as mobile phones, PDAs, RIM, PocketPC, and others.

The present invention was designed to overcome limitations of the prior art and provide consumers with a wireless prescription management and compliance solution which is cheap, easy to use, personalized, automated, and easily incorporated into their daily lives. The invention is designed for use with any mobile phone or wireless device, so that the system is made easy to use even for individuals unskilled in the use of wireless or other technologies.

BRIEF DESCRIPTION OF THE FIGURES

The figures depict a preferred embodiment of the present invention for purposes of illustration only. One skilled in the art will readily recognize from the following discussion that alternative embodiments of the structures and methods illustrated may be employed without departing from the principles of the invention described herein.

FIGS. 9A-9F illustrate exemplary wireless prescription message reminders containing text, enhanced text, graphics, logos, WAP links, auto-reply buttons, pill images, and advertisements in accordance with the present invention;

SUMMARY OF THE INVENTION

Figure 1:
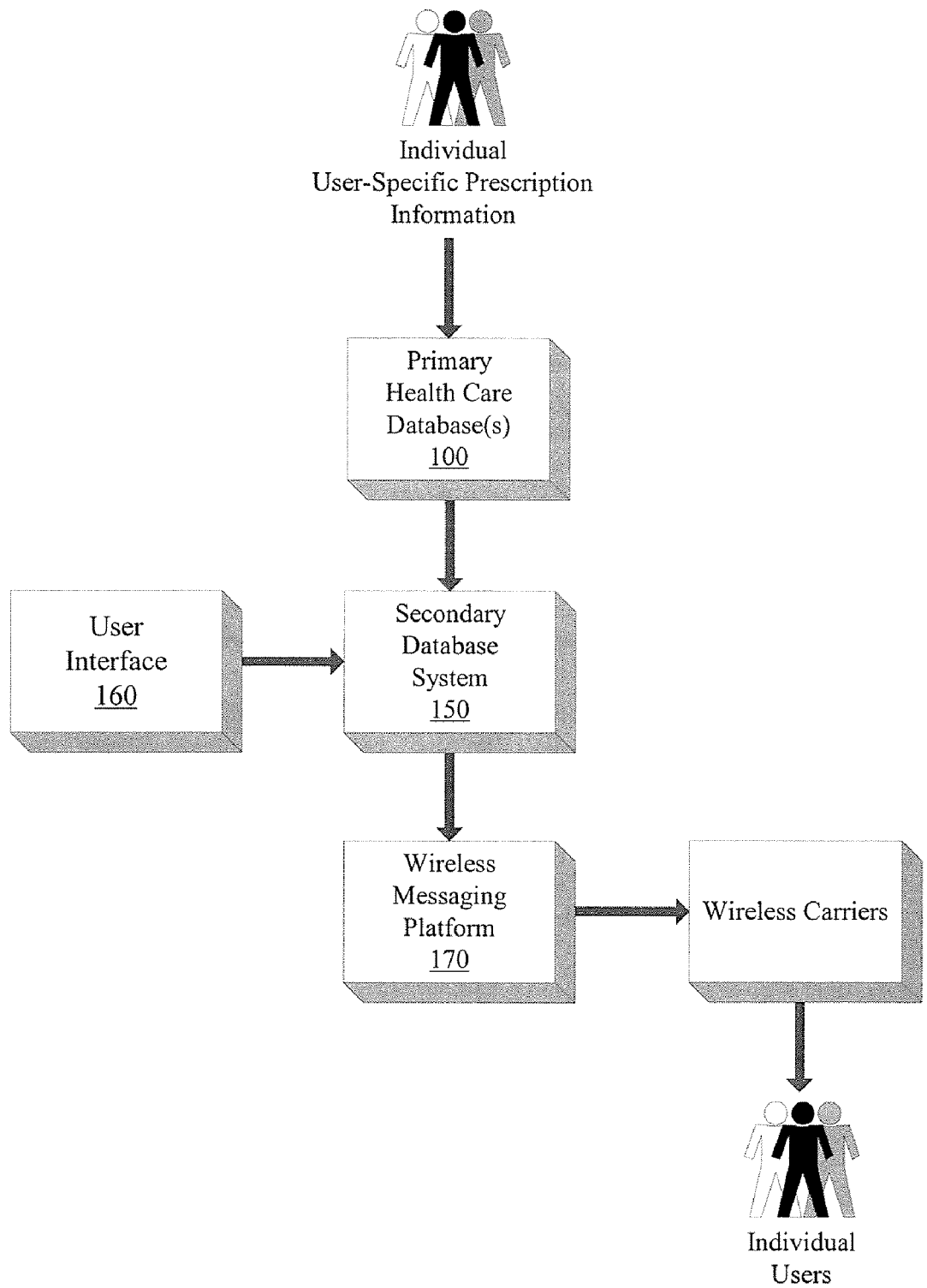
FIG. 1 is a block diagram of an exemplary system framework comprising primary health care database(s), a secondary database system, user interface, and wireless messaging platform, which are integrated according to the flow arrows.

The system outlined in the invention is an integrated framework comprised of one or more primary health care database (s), a secondary database system and program module, user interface, and wireless messaging platform which is connected to wireless networks and wireless subscribers. The objective of the system is to provide users with an account to manage their prescription treatments and automated, real-time, enhanced wireless prescription dosing reminders to increase the user's prescription compliance.

It does so by (i) enabling the user to set up a user account in order to access their source prescription data, (ii) aggregating prescription data from a number of disparate sources so that the user's account is both complete and continually updated, (iii) automatically scheduling prescribed doses to be taken by superimposing the user's source dosing indications with his or her selected hourly/daily schedule, and (iv) providing scheduled real-time wireless prescription dosing reminders complete with text-based dosing instructions, pill images, online and WAP resources, audio/video, and compliance verification and other features. The system enables the user to further customize notifications for each prescription and add vitamins, OTC drugs, supplements, and herbal remedies to their account, so that they can comprehensively manage their entire health care regimen. Users can also view and analyze their compliance by responding to their wireless reminders through two way messaging, WAP links, or IVR sessions and viewing those statistics in the user interface.

In addition, the system enables users to add authorized individuals to their account and direct their wireless prescription reminders to said individuals, so that they may help administer and manage the user's prescription treatments.

Lastly, the system allows the user to set up a notification system wherein selected individuals may be automatically notified and given specific protected health information in the event of an emergency or adverse event due to a particular drug dose taken.

This integrated framework enables automation and updating of the system, so the user need not manually reprogram the system every time prescriptions are added, terminated, or changed. Users can simply customize their account once, and use those settings for the term of their enrollment.

There are a number of alternatives for integrating the components that comprise this system framework. Different components and technologies may be adapted depending on the underlying primary database technologies used. For example, one embodiment of the system framework involves aggregating and integrating one or more primary health care databases into a Microsoft SQL Server 2000 Enterprise Edition database or data warehouse using an open database connectivity (ODBC) database driver which executes the data migration and transformation process with Structured Query Language (SQL)-based commands. This secondary database is then integrated into the wireless messaging platform by using Web Services middleware with a simple object access protocol (SOAP) interface. The wireless messaging platform may be connected to any number of wireless carriers for distribution of wireless messaging content to end users through mobile phones or other wireless devices. This XML-over-HTTP architecture allows for the streamlined incorporation of a Web-based, WAP, or mobile application-based user interface with the secondary database system used to customize the user's account, manage prescriptions, and drive wireless message content.

This proposed embodiment is only one of several which are known to those skilled in the art of wireless and database technologies, and is in no way no way intended to be limiting. Other objects, advantages, and novel features of the present invention will become apparent from the following detailed description of the invention when evaluated in conjunction with the accompanying drawings.

DETAILED DESCRIPTION OF THE PREFERRED EMBODIMENTS

FIGS. 1-6 outline various alternative embodiments of the system's framework and integrated components.

FIG. 1 is a block diagram of an exemplary system in accordance with one aspect of the present invention. User-specific prescription information enters the system and is stored on one or more primary health care database(s) 100. The primary heath care database(s) 100 are integrated with a secondary database system 150, which is linked to both the user interface 160 and wireless messaging platform 170. Wireless prescription reminders, messages, and other electronic transmissions are routed from the wireless messaging platform 170 to the wireless carriers, wireless networks, and ultimately to the original users and other individuals on their wireless phones and devices.

Figure 2:
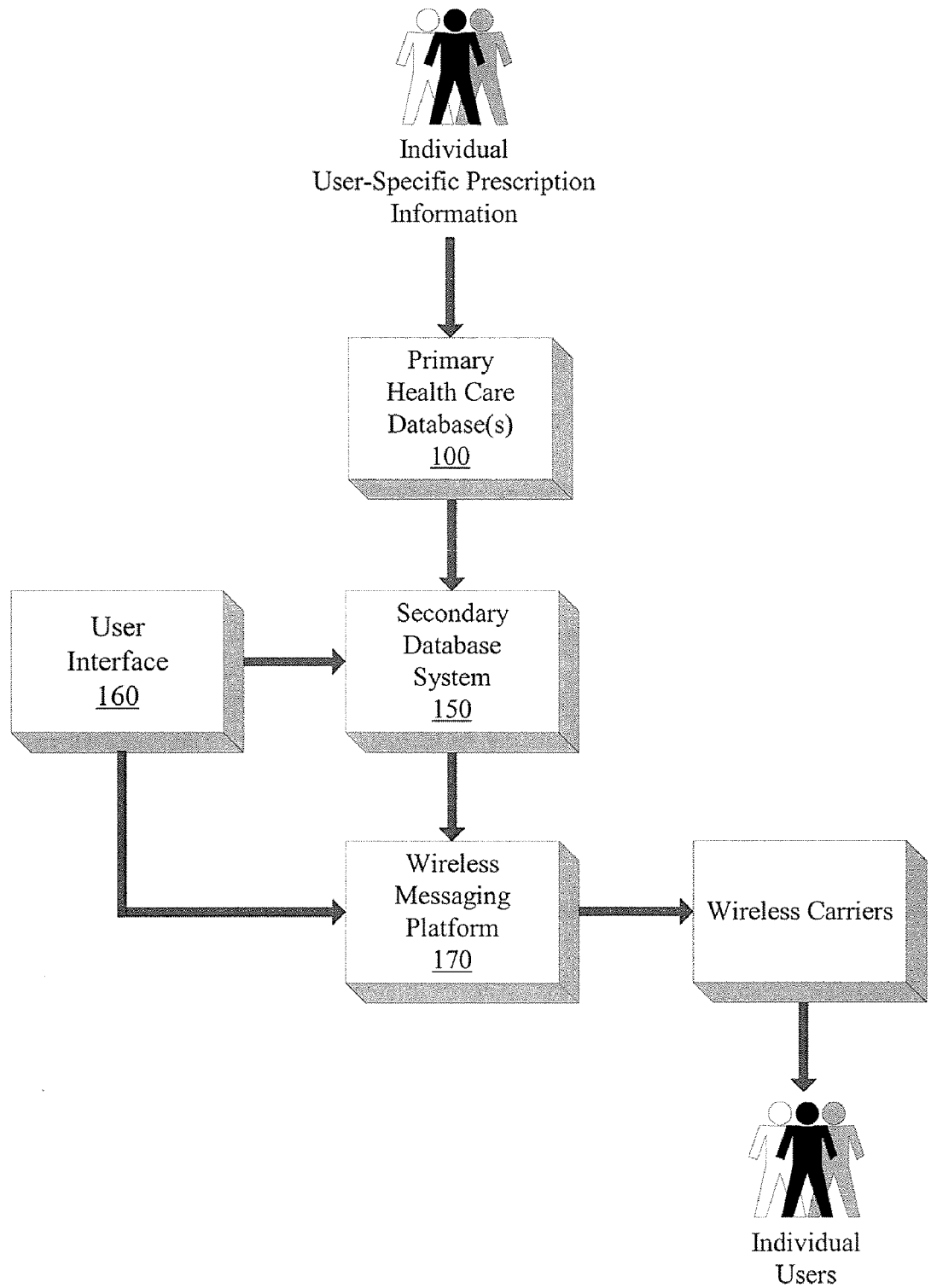
FIG. 2 is a block diagram of the exemplary system framework in FIG. 2, except that the user interface is integrated with both the secondary database system and wireless messaging platform.

FIG. 2 is a block diagram of an exemplary system in accordance with another aspect of the present invention. The system of FIG. 2 is similar to that of FIG. 1 except that the user interface 160 is coupled to both the secondary database system 150 and wireless messaging platform 170 to provide enhanced functionality.

Figure 3:
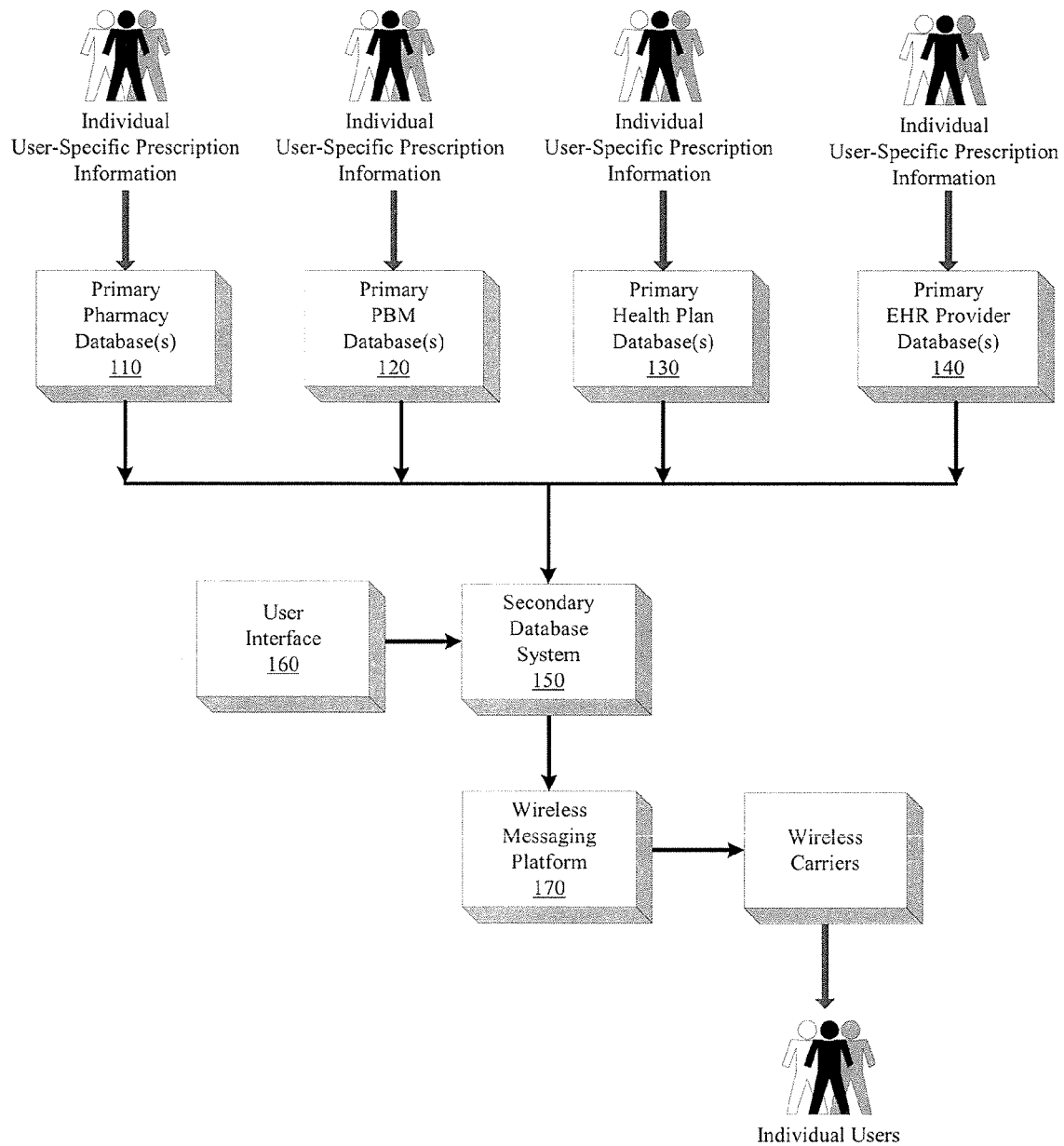
FIG. 3 is a block diagram of an exemplary system framework in which multiple primary databases from multiple pharmacies, PBMs, health plan, and/or EHR providers are integrated with the secondary database system, user interface, and wireless messaging platform according to the flow arrows.

FIG. 3 is a block diagram of an exemplary system in accordance with another aspect of the present invention. The system in FIG. 3 is similar to that of FIG. 1, except that it illustrates the fact that the primary health care database(s) 100 may be comprised of multiple primary pharmacy databases 110, primary PBM databases 120, primary health plan databases 130, and primary EHR provider databases 140, all of which are integrated with the secondary database system 150 and linked to the user interface 160 and wireless messaging platform 170.

Figure 4:
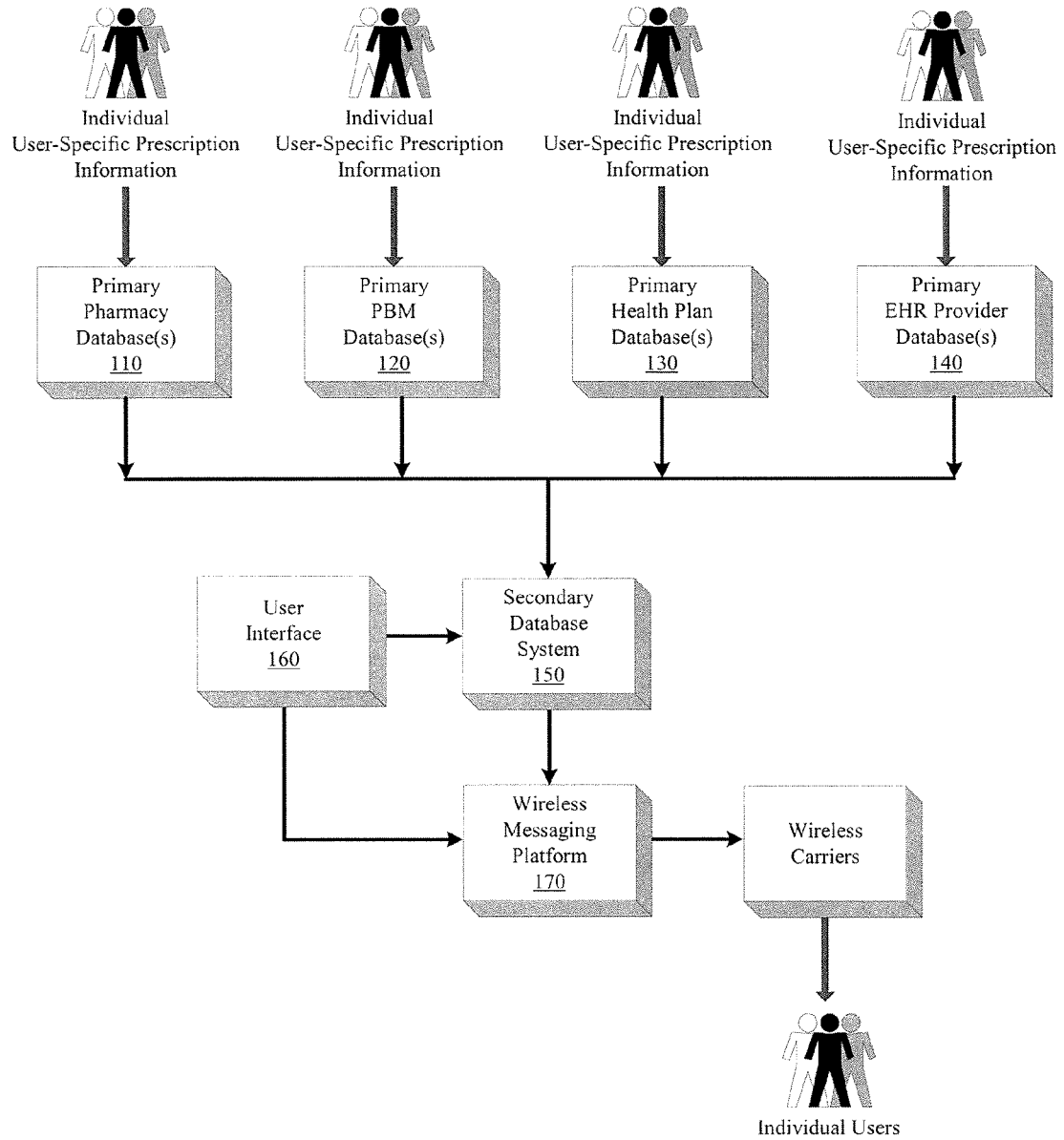
FIG. 4 is a block diagram of the exemplary system framework in FIG. 3, except that the user interface is integrated with both the secondary database system and wireless messaging platform.

FIG. 4 is a block diagram of an exemplary system in accordance with another aspect of the present invention. The system of FIG. 4 is similar to that of FIG. 3 except that the user interface 160 is coupled to both the secondary database system 150 and wireless messaging platform 170, to provide enhanced functionality.

Figure 5:
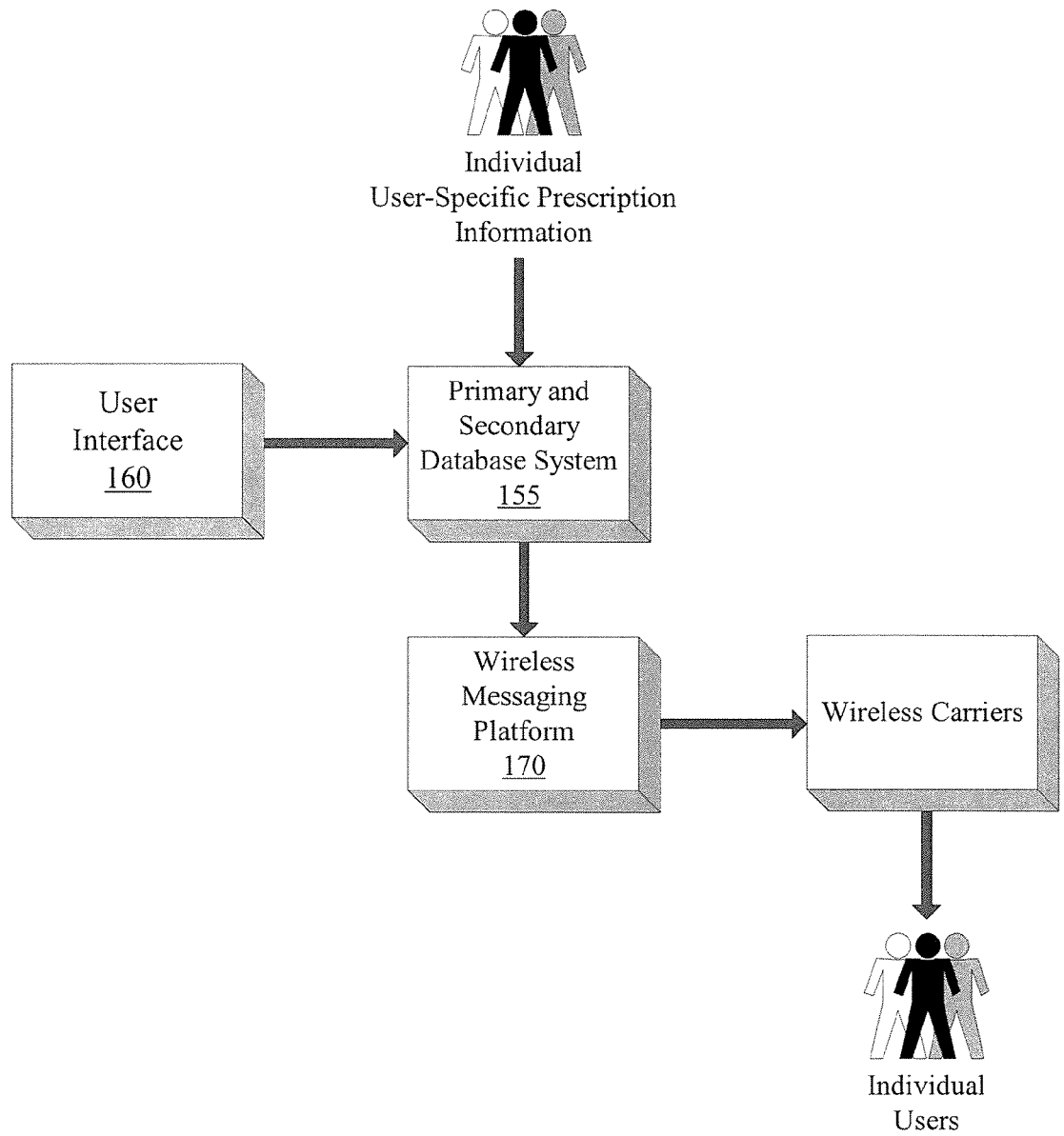
FIG. 5 is a block diagram of an exemplary system framework in which the use of a single primary database enables the primary and secondary databases to operate as one system which is integrated with both the user interface and wireless messaging platform according to the flow arrows.

FIG. 5 is a block diagram of an exemplary system in accordance with another aspect of the present invention. In the case where only one pharmacy, PBM, health plan, or EHR provider primary database is used, the primary and secondary databases 155 may be combined into one database system and integrated with both the user interface 160 and wireless messaging platform 170.

Figure 6:
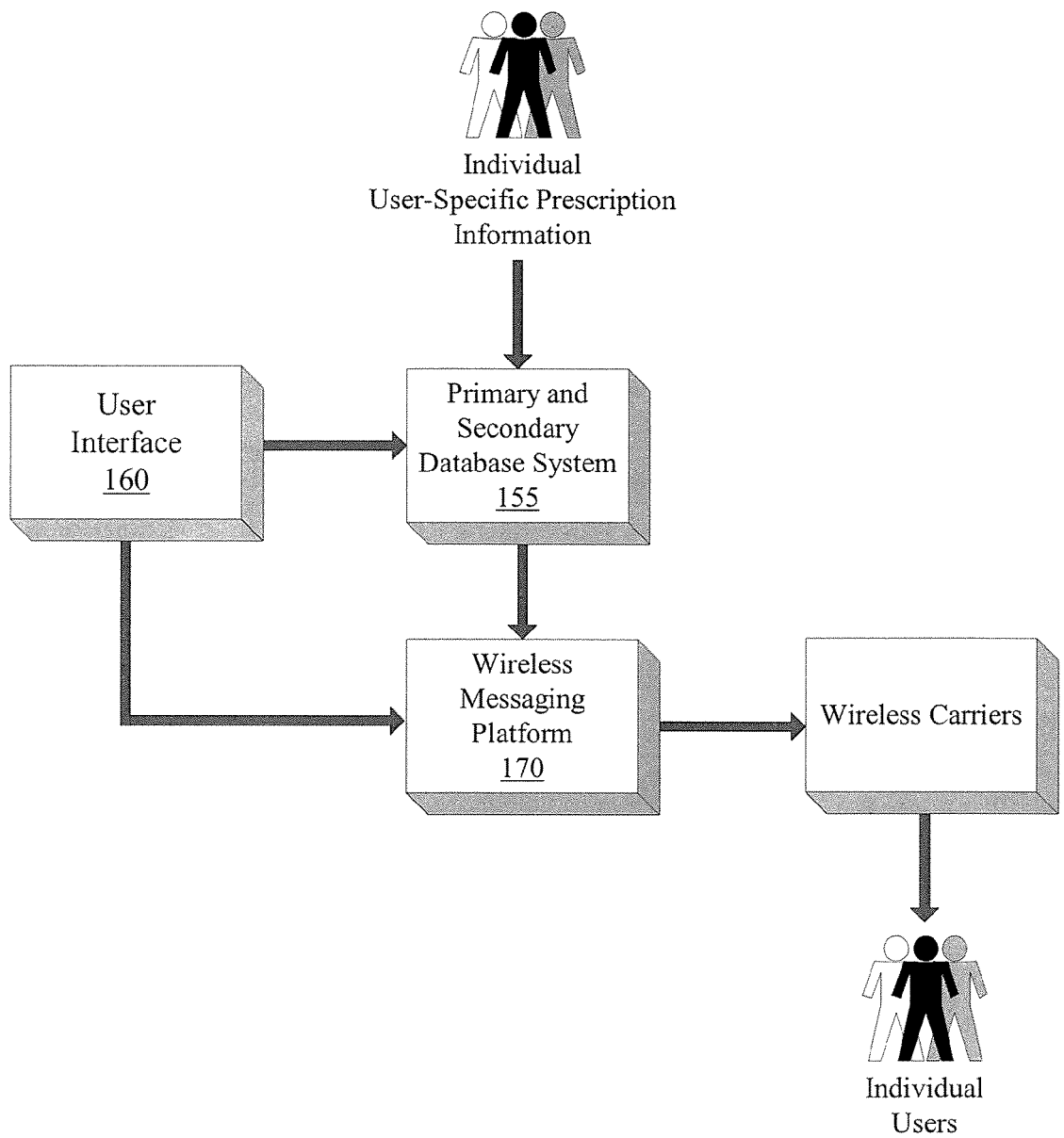
FIG. 6 is a block diagram of the exemplary system framework in FIG. 5, except that the user interface is integrated with both the primary/secondary database system and wireless messaging platform.

FIG. 6 is a block diagram of an exemplary system in accordance with another aspect of the present invention. The system of FIG. 6 is similar to that of FIG. 5 except that the user interface 160 is coupled to both the primary and secondary database system 155 and wireless messaging platform 170, to provide enhanced functionality.

In any of the aforementioned figures, any of the primary database(s), secondary database system, user interface, and wireless messaging platform may be owned and/or operated by one of the health care entities.

Primary Health Care Database(s)

User-specific prescription information is stored on a number of databases controlled by different classes of health care entities. These entities include: pharmacies, PBMs, health insurance companies or health plans, and EHR providers. This individually identifiable health information is termed protected health information under the Health Insurance Portability and Accountability Act of 1996 (HIPAA). The aforementioned entities all maintain and share patient-specific prescription and health information in order to manage health care, medical treatments, claims, and billing for their customers and perform their business functions.

Of these entities, pharmacies are still the primary source of user-prescription source data and remain the primary suppliers of prescription drugs to individuals, although mail order and online purchasing through PBMs is becoming increasingly popular. Pharmacies receive and process prescription orders from physicians which contain drug related information and indications for treatment. This data is loaded into the pharmacy's database network in order to authorize and dispense prescriptions, process claims and billing, and perform other health care operations on behalf of the individual. Examples of the data inputted by a pharmacy processing a prescription include data fields such as the user's name, drug name, NDC code, dosage, dosing, duration, treatment indications, number of refills authorized, physician's name, and contra-indications, among others. In database terms, pharmacy data sources include all electronic repositories of information that contain user-specific prescription data of interest for management, use, or analytics.

In addition to the computers and local databases which organize and manage prescription orders for each retail outlet, pharmacies now maintain central databases and servers which aggregate and consolidate patient specific data from their individual retails outlets. These central databases enable the pharmacies to maintain up-to-date information and drug histories for each customer so that the customer can receive value-added prescription services such as checking for drug-drug interactions, warnings, and other indications, irrespective of the retail outlet from which the prescription is dispensed.

The detailed prescription information inputted at the branch pharmacy level is made available to the networked health care system through database systems which communicate, store, manage, and process this PHI and health-related information. These organizations use a range of databases, systems, and servers for this purpose. With reference to the present system, the term primary health care database is used to encompass a number of formats for data storage and management. These primary health care databases may be comprised of legacy systems, data warehouses, relational databases, database management systems (DBMS), online transaction processing system (OLTP) databases, client-server databases, mainframe databases, development, test, staging, and production databases, data marts, and their servers, among others. The properties and design of these database systems can vary widely as there are a variety of databases and technology platforms used by the different companies in the health care industry. Some of these include: IBM DB2, Oracle, Microsoft SQL Server, Sybase, Informix, PostgreSQL, Progress, Apache Derby, DB2, FileMaker, Helix, Informix, Microsoft Access, Sybase, Teradata and other databases. There are also a varied number of DBMS such as Lotus Approach, Microsoft Access, and FileMaker Pro.

In addition to pharmacies, each class of health care entity utilizes user-specific prescription information and/or HIPAA protected PHI in conjunction with their business function. For example, health plans store member-specific personal and medical health information in order to manage billing, claims, and medical treatments for their members. Most health plans now outsource prescription drug claims and billing to PBMs who administer drug benefit programs for employers and insurance companies, as well as managing pharmacy benefits such as the purchasing, dispensing, and reimbursement for prescription drugs. PBMs consolidate a wide variety of prescription data and information on behalf of their members, including user-specific prescription information stored by multiple pharmacies. PBMs use the National Council of Prescription Drug Programs' ("NCPDP") Telecommunication Standard Version 5.1 to process pharmacy claims, an electronic infrastructure by which in excess of 90% of retail pharmacies are connected. Since an individual may purchase their prescribed drugs from a variety of sources, at any one time an individual's PBM may maintain the most up-to-date drug history for a particular individual. Electronic health record (EHR) providers are new networked entities whose function is to aggregate and consolidate member-specific health care records for use by physicians and hospitals in patient treatments. These providers are just emerging and it has yet to be seen whether one provider can accurately consolidate medical information from all sources where a given patient interacts.

Although user-specific prescription information is stored on a number of databases controlled by different health care entities, individual users do not readily have access to this information in part or in whole.

Pharmacies, PBMs, health plans, EHRs, and other health care-related entities in the United States are subject to extensive regulation by the Department of Health and Human Services (HHS) and the Health Insurance Portability and Accountability Act of 1996 (HIPAA). Dispensing of prescriptions and management of prescription drug benefits require the ability to use an individual's PHI. PHI is any individually identifiable health information created by or received from a health care provider, health plan, or clearinghouse, related to the provision of healthcare or payment for healthcare, which identifies or could reasonably be used to identify an individual and has been transmitted electronically or maintained in any other form or medium. At the federal level, HIPAA and HHS have adopted extensive regulations governing the transmission, use, and disclosure of health information by all participants in healthcare delivery. Specifically, HIPAA has created new federal Security and Privacy Standards regarding PHI, and is currently making new rulings on electronic maintenance and transmission of PHI within and outside of the healthcare system.

As such, users and other individuals must sign a HIPAA release to get access to this PHI, and all entities involved in the proposed invention must be either HIPAA Covered Entities or sign Business Associate or Sub-Business Associate Agreements with the Covered Entities to get access to an individual's PHI. Covered Entities include pharmacies, health plans, health care providers, and other entities that transmit PHI in electronic form. Business Associates and Sub-Business Associates include PBMs, consultants, auditors, subcontractors, and other entities that perform a business function or activity involving the use or disclosure of PHI on behalf of the Covered Entity. These entities and all databases, servers, and hosting methods used in the system by such qualified entities must comply with HIPAA Privacy and Security Standards for electronic PHI.

Source user-specific prescription information is very important, but it is of no use to the individual in its current electronic format. It must be aggregated, personalized, transformed, adapted to the user's schedule, and made available on standard technologies in order to be effective as a prescription management tool and compliance aid.

Secondary Database System

The secondary database system gives the user access to prescription source data that he or she would not normally be able to access or use in its original electronic format. Users may create, access, and modify a user account by using an interface which is integrated with the secondary database system. This user account is stored in the database within the secondary database system. Setting up and customizing a user account enables the user to aggregate, customize, enhance, and manage their prescription source data for use in prescription management and compliance.

The secondary database system serves as the hub for the system as a whole. It aggregates, transforms, stores, organizes, manages, and processes data being inputted and manipulated by each component of the system. The secondary database system program module receives, processes, and integrates data from the primary health care databases, user interface, and wireless messaging platform and creates transformed user output data fields and parameters which then drive the wireless prescription reminder service, network notification, and other features. The data inputs, selections, and settings in the user's account determine the message content, parameters, and system functionality for each user.

Data processed through the user interface and stored in the user account in the secondary database enables each user to manage their prescriptions and system features including scheduling wireless prescription dosing reminders, managing their prescriptions and other OTC drugs and vitamins, giving other individuals access to their data, and setting up a networked notification service in the event of an emergency or adverse reaction to a dose taken. Information processed through the user interface may simply add information, turn system triggers and features on and off, create additional network connections for that user account, or enhance, enable, and disable features which use the user's underlying data and information as drivers for those features.

Other outside data may also be incorporated into the secondary database system in order to provide enhanced information and content for prescription data stored in the user's account and used in the wireless reminder service. Examples of outside data include medication images, marketing offers, corporate logos, icons, and graphics, Web and WAP links, and other features. The secondary database system may also maintain additional integrated connections with communications platforms such as IVR systems, GPRS systems, autodialers, and others which are a part of one or more of the system's functional features.

Figure 7:
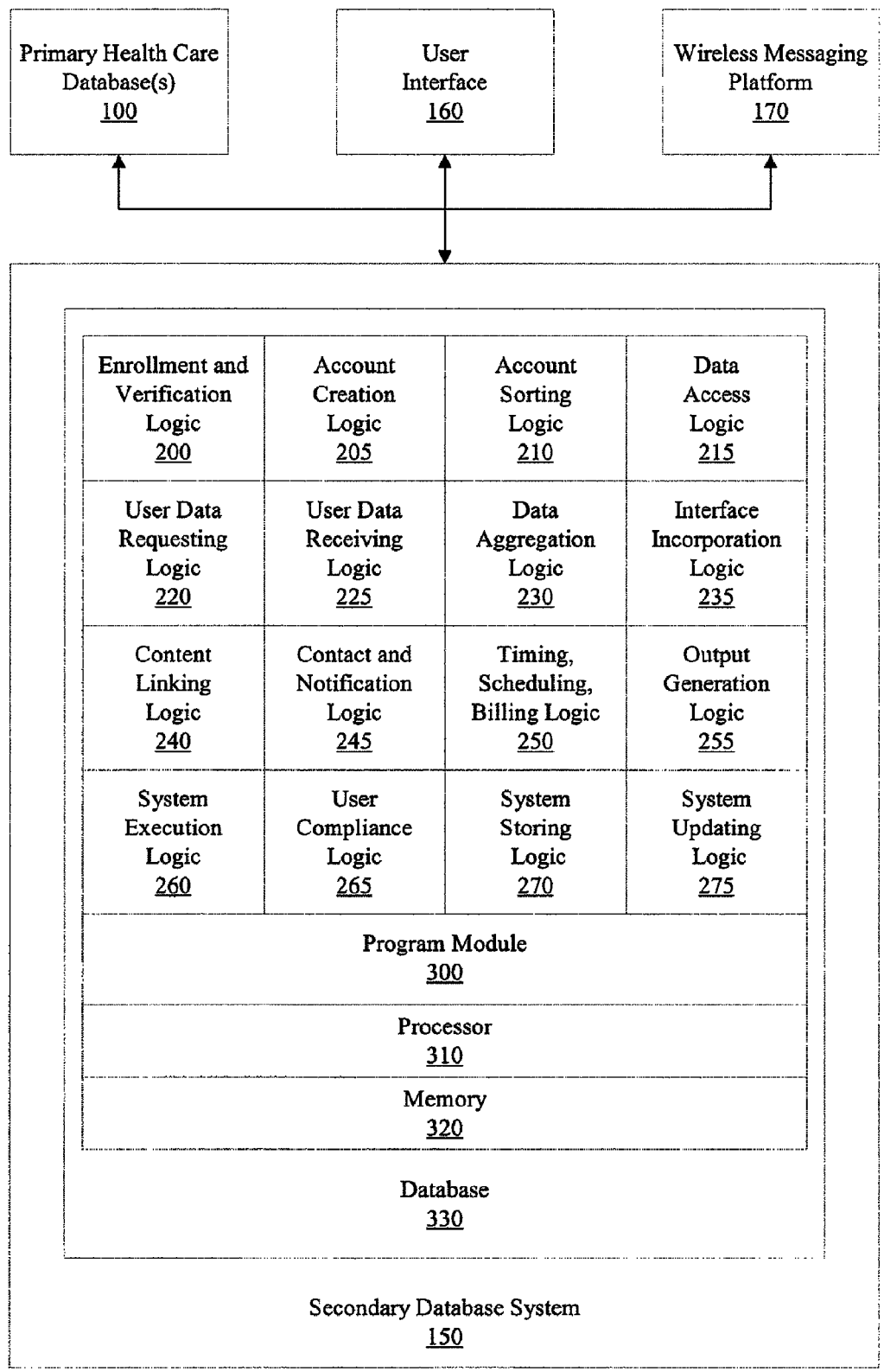
FIG. 7 is a block diagram of an exemplary secondary database system and method for a program module in accordance with the present invention.

FIG. 7 is a block diagram of an exemplary secondary database system in accordance with the present invention. The secondary database system 150 is comprised of a program module 300, processor 310, memory 320, and database 330. Program module 300 includes Logic 200-275. Logic 200-275 can be processor 310 executable code loaded from memory 320. This processor-executable code can be part of a single executable program or can be components of a number of different executable programs. Program module 300 has an execution flow that can handle events, transformations, and conditional logic and is programmed to automatically process, store, and execute system triggers and functions based on default settings, personalized settings, and/or data field outputs generated by integrating and processing data from the primary health care databases 100, secondary database 330, user interface 160, and wireless messaging platform 170.

Specifically, enrollment and verification logic 200 verifies and processes prerequisite system sign up information and HIPAA PHI releases. Account creation logic 205 creates a user account in the secondary database 330, which is set up initially using default settings, but with a full range of modifiable data fields, settings, and functions. Account sorting logic 210 organizes and sorts accounts by social security number, user name, and/or other personal identifiers. Data access logic 215 initiates integration and communication between the secondary database system 150 and primary health care databases 100 through the selected integration architecture, and enables the exchange of data between the two systems. Data access logic 215 also enables integration, communication, and processing of data between the secondary database system 150, user interface 160, and wireless messaging platform 170. User data requesting logic 220 and user data receiving logic 222 outline the commands, transformations, links, and tags which enable this data transfer between heterogeneous systems. User data requesting logic 220 queries primary health care databases 100 for data based on the user's record identifiers stipulated in account sorting logic 210. Data aggregation logic 230 aggregates and compiles user-specific prescription data from participating primary health care databases into each user's account. Interface incorporation logic 235 incorporates data, content, and input selections from the user interface 160 into the user's account. Content linking logic 240 links, integrates, and consolidates additional content into user's account in order to enhance the user's prescription data and wireless prescription messages. This additional content may include pill images, audio, video, logos, informational Web or WAP links, and other content stored on the database 330. Contact and notification logic 245 creates additional network connections in the user's account and additional reply options for the wireless prescription reminder messages by verifying, processing, and adding additional contacts to the user's wireless reminder and notification system. Timing, scheduling, and billing logic 250 amends the system's functionality for the user, based on conditional logic using data fields and selections made on the interface 160. Output generation logic 255 creates data field outputs or parameters derived from integrating user source prescription data with customized user account data selections, modifications, and additions from the interface 160. System execution logic 260 sorts and processes data field outputs and parameters in conjunction with data and content in the user's account to drive the wireless messaging platform and its features. System execution logic 260 then confirms execution of system processes and organizes execution data such as wireless prescription message receipts, confirmed billing, and other data in user's account. User compliance logic 265 integrates additional reply options into the wireless prescription reminder messages and enables two-way compliance data received from the user through the wireless messaging platform 170, IVR session, or other communication method. System storing logic 270 stores user data, settings, outputs, execution history, and other information from the user's account in sequential time based files in the secondary database 330. System updating logic 275 automatically updates the user's account at given time intervals for changes in the user account due to system execution, time lapsed, and new and modified data from the primary health care databases 100, user interface 160, and wireless messaging platform 170.

Lastly, the secondary database system 150 is integrated with all primary health care databases 100, the user interface 160, and the wireless messaging platform 170. The integrated nature of the framework results in a continually automated and updated system, so that the user need not reprogram the system or settings for each new prescription, change in dosing, or other event.

Primary Database(s)—Secondary Database System Integration

To achieve full automation and functionality, the primary database(s) and secondary database system must be connected and integrated so that data, methods, objects, schema, and other parameters from the primary database(s) may be updated and made available to the secondary database system on a continual basis. Some existing primary database engines natively support common methods for producing connectivity, such as using extensible markup language (XML) for integration of relational data. XML is a meta-markup language that provides a format for describing structured data. Unlike HTML, XML does not handle the presentation of data. Instead, the tags used to encompass the data are used to describe the data. This allows for a simplified passing of data between two programs. There are a number of methods for utilizing XML over a network to enable connectivity and inter-operability including XML-RPC, Web Services, Middleware, and other systems.

Certain existing primary databases also have data transformation service (DTS) enhancements so that the DBMS can perform tasks or set variables based on properties of the run-time environment such as: importing data from and sending data and completed packages to Internet and FTP sites, running packages asynchronously, building packages that send messages to each other, building packages that execute other packages, or joining multiple package executions as part of a transaction. Other enhancements include data mining, data analysis, HTTP or HTTPS connections, linked cubes, drillthough, multi-user administration, meta data enhancements, and other features.

Pharmacy, PBM, health plan, and EHR technology platforms are often run on a variety of different proprietary technologies and use a variety of different hardware, databases, programming languages, and operating systems to manage their data. Extracting and integrating data from heterogeneous database environments presents a number of data access challenges related to the disparate number of technologies used in each system. As a result, system integration with multiple primary databases may be effected within the secondary database system program module through one or more of the following data integration methods which use data abstraction, loose application couplings, application programming interfaces, technology bridges, middleware, objects, and other protocols and technologies.

Data warehousing using extraction, transformation, and loading (ETL) can be perceived architecturally as a tightly coupled approach because the data reside together in a single repository at query time. During the process of data migration, data from several sources is extracted, transformed, and loaded into a database or data warehouse where it may be queried with a single schema. The ETL meta data functional element is responsible for maintaining information about the movement and transformation of data, and the operation of the data warehouse. There are a number of homogenous or heterogeneous ETL architectures for integration with single or multiple data sources. Data migration and ETL can be done at several levels in the database architecture including at the repository, primary, or central database or data warehouse level, including sub-sets of the source data such as dependent data marts, logical data marts, and operational data stores, among others. The end result is a real-time and integrated data warehouse derived from multiple heterogeneous sources.

Alternative data integration solutions use data abstraction to address the data access challenges associated with data heterogeneity and data contextualization. These integration solutions include: enterprise application integration (EAI) solutions such as the enterprise service bus (ESB), enterprise information integration (EII) solutions such as those using APIs and bridges including ODBC, JDBC, OLE-DB, or ADO.NET, Service-Oriented Architectures (SOA) using Web Services, SOAP, or XML-RPC, Middleware such as Common Object Request Broker Architecture (CORBA), Component Object Model (COM), and Distributed Component Object Model (DCOM), among others.

Enterprise Application Integration (EAI) solutions are used to share data between applications as well as processes. A health care entity may have existing legacy applications and databases and want to continue to use them while adding or migrating to a new set of applications that exploit the Internet, e-commerce, extranet, and other new technologies. An EAI architectural system can address large scale interdisciplinary problems with multiple, heterogeneous, distributed systems that are embedded in networks at multiple levels. EAI encompasses methodologies such as object-oriented programming, distributed, cross-platform program communication using message brokers, the modification of enterprise resource planning (ERP) to fit new objectives, enterprise-wide content and data distribution using common databases and data standards implemented with the extensible markup language (XML), middleware, message queuing, and other approaches. It is currently thought that the best approach to EAI is to use an enterprise service bus (ESB), which connects numerous, independent systems together. The advantages of EAI are enabling real-time information access among systems, streamlining business processes, and maintaining information integrity across multiple systems.

Enterprise Information Integration (EII) solutions involve using data abstraction to circumvent issues with data access and translation. There are a number of standardized data access application programming interfaces (APIs) such as open database connectivity (ODBC), Java database connectivity (JDBC), OLE-DB, and PERL DBI which provide a standard software API method for using DBMS. These APIs provide bridges for connectivity, extraction, and translation by creating homogeneous data representations for heterogeneous and disparate data sources. Regardless of which EII product is chosen, there is essentially a common four step process involved, subject to variation based on the back-end technology used by the primary health care database.

EII products enable loose couplings between applications associated with the secondary database system and the heterogeneous primary health care data sources. EII products translate heterogeneous data into commonly used formats such as SQL, XML, data-returning web services, and other URI-based resources. This process entails linking the secondary database system to an applicable driver such as ODBC, JDBC, OLE-DB, or PERL DBI which serves as a bridge between the primary database and programming language used by the secondary database system program module, selecting a programming language such as ASP, PHP, or PERL that enables execution of SQL or other commands against it, and finally processing the information using a discrete or composite Web Service, Dynamic HTML/

XHTML/XML Web Page, or XML transformation, and integrating the data over an open connection. In this way, a single EII product can provide access to data in several relational database tables, each associated with a different database engine, from a different database vendor, and associated with a myriad of enterprise applications.

Service-Oriented Architectures (SOA) are a style of information system architectures that enable the creation of applications built by combining loosely coupled and interoperable services. Like EII, these services inter-operate based on or using a standard language which is independent of the underlying platform and programming language. In this way, SOA removes some of the restrictions that proprietary software systems impose on data integration. SOA-compliant systems can therefore be independent of the development technologies and platforms employed by different primary health acre entities.

There are a variety of custom built designs and interfaces in a SOA-based system. One class of SOA architecture employs the use of the Web Service Protocol Stack. Web Services connect disparate systems and resources together via a universal language and framework. Web Services typically uses XML as the mark up language to describe data in message payloads, HTTP as the response/request protocol, SOAP, REST, RPC, or another method for exchanging XML-based or other messages over a computer network, WSDL to describe the public interface, protocol bindings, and message formats required for interaction with the service, and a listing in a UDDI registry.

Component Object Model (COM), Distributed Component Object Model (DCOM), and now .NET are Microsoft proprietary technologies used to enable software components distributed across several networked computers to communicate with each other. They provide the communication substrate under Microsoft's COM+ and .NET application server infrastructure. The first service-oriented architecture used in the past was DCOM, in conjunction with the use of Object Request Brokers (ORBs). ORBs are pieces of middleware that allow programmers to make program calls from one computer to another, via a network. DCOM is designed for use across multiple network transports, including Internet protocols such as HTTP.

Common Object Request Broker Architectures (CORBA), a form of Middleware, wrap code written in some programming language into a bundle containing additional information on the capabilities of the code inside and how to call it. The resulting wrapped objects can then be called from other programs or CORBA objects over the network. CORBA can be considered a machine-readable documentation format, similar to a header file found in a SOAP envelope, but with considerably more information. CORBA uses an Interface Definition Language (IDL) to specify the interfaces that objects will present to both client and server, and then specifies a mapping from IDL to a specific implementation programming language. Both standard and non-standard mappings exist for ORBs written for those languages. General and Internet Inter-Orb Protocol™ (GIOP/IIOP™) are abstract protocols by which ORBs can communicate over networks and TCP/IP. Using IOP™, a CORBA-based program can interoperate with another CORBA-based program from any vendor, on any operating system, network, or programming language. CORBA therefore enables integration of multiple primary health care databases with disparate operating systems and programming languages by linking each to the same interface.

There are a number of variations and enhancements to CORBA including Java RMI-IIOP, the CORBA component model, and OMG's data distribution service (DDS), among others. There are a wide variety of commercial implementations of CORBA designed for use with specific platforms and programming languages.

Microsoft ActiveX Data Objects (ADO) is a set of COM objects for accessing data sources. It provides a layer between database programming languages and OLE DB, by which a program can be integrated to access data on the underlying database. ADO.NET is an upgraded version of ADO for use with Microsoft's .NET framework. ADO.NET provides consistent access to data sources such as Microsoft SQL Server, as well as data sources exposed through EII APIs such as OLE DB and XML. ADO.NET provides access to relational data, XML, and application data and supports a variety of development needs, including the creation of front-end databases for integration and middle-tier business objects used by applications, tools, languages, or Internet browsers. The ADO-.NET platform allows for enterprise data integration and the creation of data-sharing consumer applications which can connect to these data sources and retrieve, manipulate, and update data. The ADO.NET architecture is comprised of (i) a data provider that provides the connection, translation, commands, and a bridge used to transfer data between a data source and, (ii) the DataSet, a data-source-neutral relational database. ObjectSpaces are a new set of data access APIs for the Microsoft .NET Framework which treat data as objects, independent of the underlying data store, and encapsulate their physical structure of tables, rows, and columns. These ObjectSpaces objects can be used to retrieve data from the datastore, navigate data using its relationships, modify the data, and commit the changes back on the datastore. ObjectSpaces have classes which enable connections to both relational databases and XML data stores. These classes can be extended to create adapters for other types of data stores as well. There are a number of ADO.NET variations and providers including Microsoft, Simba Technologies, DataDirect Technologies, OpenLink Software, and others.

There are a number of variations, implementations, and alternatives to each of these data integration solutions as a result of the diversity in software, hardware, databases, operating systems, and programming languages employed by different health care entities. The convenience of these data integration solutions is that new sources can be added by simply constructing an adapter for them. An ETL system or single database solution may also be used where the entire new dataset must be manually integrated into the system. Regardless of the type of integration solution selected, each accomplishes the objective of this component in the system, which is to integrate, aggregate, update, and automate the secondary database system with the source data from one or more disparate primary health care entity databases.

User Interface

The system utilizes a user and/or system interface and processor which is integrated with the secondary database system and may be integrated with the wireless messaging platform as well. The interface allows users and system administrators to access, add, delete, amend, and otherwise modify data fields, switches, and settings relevant to the user's account within the system. The interface may be a secure website accessible from any PC or other Web-based device, graphical user interface (GUI), Web-based, WAP, mobile application-based, or other interface which allows integration and communication between the interface and secondary database system.

The interface may be set to a default setting upon establishing a user account and then customized as desired. For example, the interface may use default settings including (i) a daily schedule setting of 7 am-10 pm, with a ½ hour lead time in the morning and pre-set meal times at 7:30 am, 12:30 pm, and 7 pm, (ii) billing by the user's wireless carrier, (iii) no additional individuals linked to the account, (iv) no additional contacts for the notification service, and (v) no set up or use of compliance analysis using two-way messaging.

In one example, if a prescription were incorporated into the user's account from a primary health care database that stipulated three times a day dosing for that medication, the secondary database system program module would create dosing output data fields using conditional logic by superimposing and processing the user's default schedule with the prescription dosing indications stored in the secondary database system. The system would then automatically schedule and transmit wireless prescription dosing reminders, evenly spaced at 7:30 am, 2:45 pm, and 10:00 pm for the duration of the medication term.

However, since no two users have the same preferences, the interface allows users to specify and customize system settings and features based on their individual needs and preferences. For instance, not every user's schedule is the same, and a user may wish to have another individual assist them with medication management, evaluate their treatments in terms of actual versus perceived compliance, and set up a notification network in case of adverse events or emergencies.

In another example, a user could set their daily schedule to 10 am-1 am, with meal times at 10:30 am, 2 pm, and 10 pm, select multiple primary data sources such as CVS™ and Walgreen's™ pharmacies, give their spouse access to their account data and direct their wireless prescription reminder service to their spouse's mobile phone, activate compliance analysis in order to evaluate their compliance in relation to treatment, and set up and authorize a notification network including their spouse, parents, and physician in the event of emergencies. If a prescription from each pharmacy was then incorporated into the user's account stipulating (i) three times a day dosing, and (ii) doses taken with meals, the secondary database system program module would process the amended data fields and settings in conjunction with the primary source prescription data to arrive at new system parameters for that user. The system would subsequently schedule wireless prescription dosing reminders for 10:30 am, 5:45 pm, 1:00 am, and 10:30 am, 2:00 pm, and 10:00 pm for each respective medication, directed and billed to their spouse's mobile phone, with two-way messaging reply features enabled, and EMS notification contacts including their spouse, parents, physician, and local hospital.

In general, the interface allows the user to access their personal account and aggregate multiple data sources, customize data, settings, and system functions, personalize the content, timing, recipients, and other aspects of their wireless prescription reminders, and view other inputs and outputs of the system such as graphs outlining compliance analysis.

Figure 8:
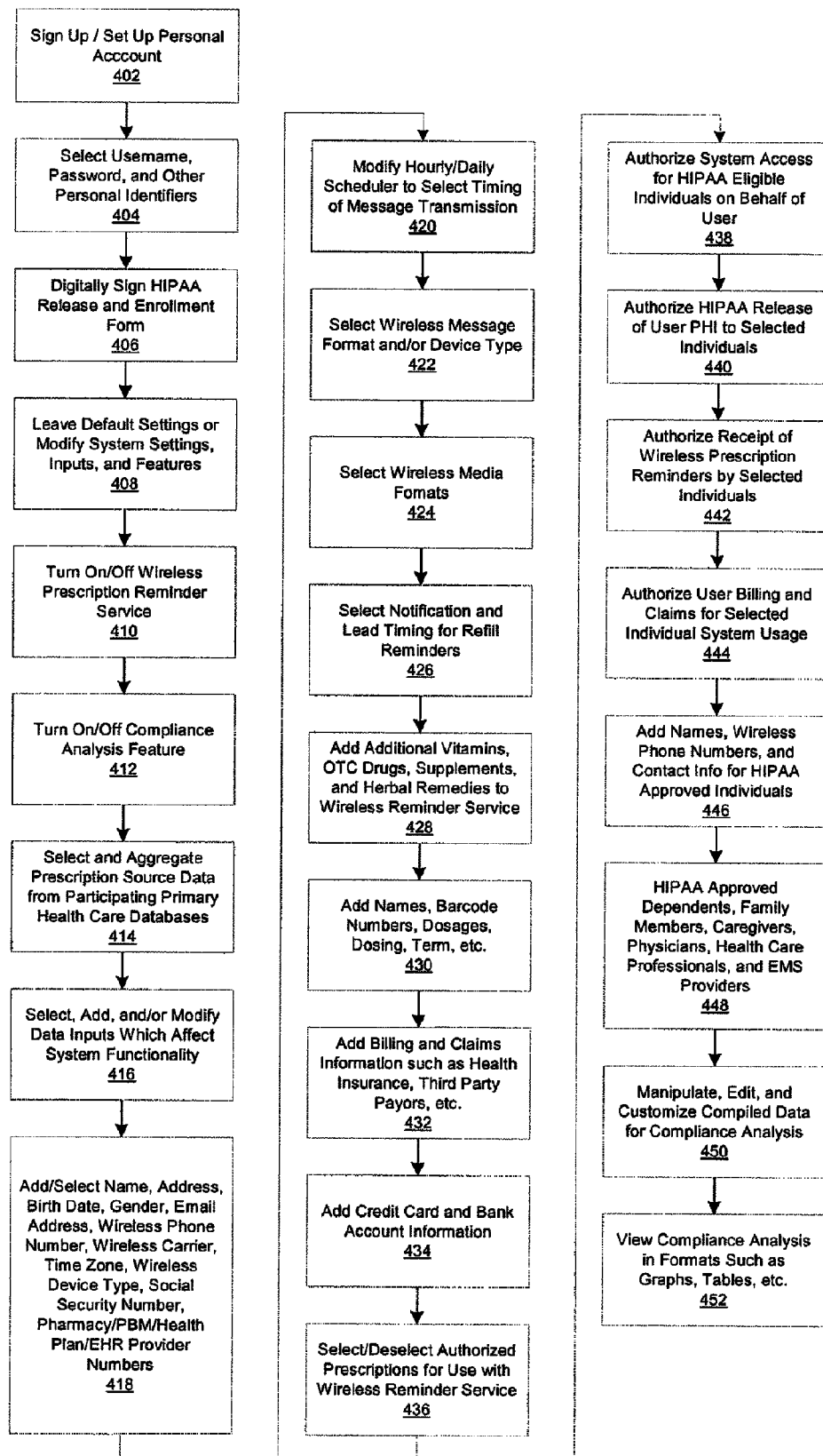
FIG. 8 is a flow diagram illustrating some of the selections and input options available on the user interface.
Figures 9E, 9F:

FIG. 8 illustrates several steps of a user account set up algorithm, accessible via the user interface, which determines the user-specific settings and functionalities of the system. Specifically, the user account, accessible via the user interface, allows the user, system administrator, and/or other individual to:

sign up and set up a user account 402 which may be accessed from multiple mobile sources including the Internet, interactive website, WAP application, mobile application based interface, or other type of interface;
    select a username, password, and other personal identifiers 404 for secure access;
    digitally sign a HIPAA release and enrollment form for the system 406;
    leave the system's default setting in place or modify the system settings, inputs, and features 408;
    switch their wireless prescription reminder service on or off 410;
    switch the compliance analysis feature on or off 412;
    select and aggregate prescription source data from participating primary health care databases 414;
    select, add, and/or modify system inputs and settings 416 such as user name, address, birth date, gender, email address, wireless phone number, wireless carrier, time zone, wireless device type, social security number, and pharmacy/PBM/health plan/EHR provider numbers 418, among others;
    modify a daily/hourly scheduler which selects the timing of transmitted wireless prescription reminders by superimposing the user's selected schedule with the dosing indications from the prescription source data 420;
    select their wireless message format (SMS, EMS, MMS, WAP, BREW), other format such as email or voicemail, or wireless device type for auto-message format selection by the system 422;
    select wireless media formats and content to be received such as text and multi-media messages, audio, video, and other formats 424;
    opt to receive wireless refill reminders and select the lead time for those notifications 426;
    add additional OTC drugs, vitamins, supplements, and herbal remedies to their wireless reminder service 428 and specify details such as names, dosages, dosing instructions, term of treatment, and other data 430;
    add billing and claims information such as health insurance numbers and third party payor and other billing/claims numbers 432;
    add credit card and bank account information for billing 434;
    select and deselect the source prescriptions to be used in conjunction with the wireless reminder service 436;
    authorize system access for HIPAA eligible individuals on behalf of the user 438;
    authorize and sign a HIPAA release of the user's PHI for selected individuals with authorized access to the user's account and system 440;
    authorize approved individuals to receive wireless prescription reminders on behalf of the user 442;
    authorize user billing and claims for individuals selected to receive wireless reminders on behalf of the user 444;
    add names, wireless phone numbers, and contact information for the selected individuals above with granted access to the user's system 446;
    add contact information and provide a HIPAA release for data used in conjunction with health care assistance or emergency medical service notification 448;
    manipulate, edit, and customize the compliance data compiled for review and analysis 450;
    view an analysis of compliance or non-compliance with user prescription treatments in formats such as graphs, tables, and other media 452, and;
    access additional data fields and features.

Wireless Messaging Platform

The object of the wireless messaging platform is to generate, format, and transmit wireless prescription reminder messages which are automatically scheduled and transmitted to the user's mobile phone or wireless device at the appropriate dosing times for each drug the user is taking. The standard wireless message delivery protocol for 2G-3G mobile phones is an audible alert, accompanied by the message display on the user's screen or mobile display, and a required response by the user to close or reply to the message. In most cases, there is no handset programming for the user to do.

FIGS. 9A-9F illustrate different embodiments of wireless prescription reminder messages received by the users. These wireless prescription reminder messages include the time, user's name, drug name, dosage, dosing instructions, and other information and content which might be helpful to the user as a treatment aid. Examples of additional message content include Web or WAP links with further instructions, pill images for the medication in question, links to websites related to the medication in question, brand versus generic pricing evaluations, advertisements, corporate logos, and others.

The wireless prescription reminders received by users are derived from the data and content stored in the secondary database system. Specifically, the settings, features, parameters, and output for each wireless message comes from a user account in the secondary database, which is the result of integrating and processing data from the primary health care databases and user interface.

The wireless messaging platform can deliver messages to the user's mobile phone and wireless device, as well as voicemail and email, based on the information stored in the user's account. Wireless messages may be delivered using different formats such as SMS, EMS, MMS, WAP, WAP-Push, BREW, SIP, HTML, and XHTML. These message formats may include standard text, formatted and enhanced text, pictures, graphics, icons, audio, video, or other multi-media content. Wireless messages may be mobile originated (MO), mobile terminated (MT), and priced as bulk or premium content. Standardized formats may be used based on the data contained in the message and the specific type of message being transmitted.

In order to give all users access to the system, it is critical to offer this prescription management and compliance solution on the devices users prefer. The platform supports diverse wireless technologies such as 2G, 2.5G, and 3G mobile phones, Smartphones, WAP phones, personal digital assistants (PDAs), Research In Motion (RIM), Palm, Web, Pocket PC, and other devices. It is fully functional with a variety of wireless device operating systems including Palm OS, Pocket PC, RIM, Epoc, Qtopia, Helix, Symbian, Smartphone, WAP, BREW, J2ME, iMode, J-Phone, Windows Mobile, Linux, and others.

The platform provides intelligent message formatting, depending on the settings in the user's account and capabilities of the user's wireless device. Examples of optimized data delivery to all device types include: intelligently rendering messages to the screen size of diverse mobile devices, intelligent formatting messages depending on the device capabilities, like one-way, two-way, WAP, and Palm, intelligent routing for global inter-carrier messaging, enterprise-class, end-to-end security, including login on all the interfaces, encryption, and SSL using digital certificates for authentication and security. The wireless messaging platform can also deliver a selective messaging solution with a blend of media, based on the device type specified in the user's account (i.e., audio and text messaging for SMS devices, text, graphics and audio for WAP devices, or text, graphics, audio, and video for MMS devices). An enhanced messaging solution capable of delivering blended media within a single application optimizes the end-user experience and improves observance and compliance with the user's prescription drug treatment.

The platform also supports inter-carrier messaging that is device and carrier agnostic as well as all popular mobile and paging protocols including TDMA, CDMA, CDMA2000, GSM, PCS, PCN, Flex, CDPD, Mobitex, GPRS, EDGE, WiDEN, UMTS, W-CDMA, HSPDA, HSUPA, and 4G. It processes both outgoing and incoming messages and data via one and two-way messaging and incorporates that data back into the secondary database system for further use and additional features.

Mobile phones, PDAs, and other wireless devices are now standard technologies which are used by over 70% of the U.S. population. The benefits of deploying the system through wireless phones and devices are (i) that consumers are already educated and well-versed in the use of mobile phone and device technologies, (ii) there is no need to purchase additional equipment, (iii) portability, convenience, and ease of use, (iv) real-time message delivery, and (v) reinforcement of the user's prescription treatments through technology association, since the system is linked to a device which is already perpetually present and used by the individual. In effect, since the mobile phone is already incorporated into the individual's daily routine, anything which is subsequently functionally linked to the device becomes integrated into the routine as well. By increasing presence, awareness, and automation, the system overcomes a number of the obstacles which prevent prescription compliance for most individuals.

The wireless messaging platform also provides the user with enhanced prescription health care features such as (i) compliance analysis, (ii) real-time health care assistance, and (iii) real-time emergency medical service notification.

Compliance analysis is derived from user-based interactive responses to the wireless prescription messages, indicating compliance or non-compliance with that dosing event. The response may take the form of a two-way or MO-based reply to the initial message (with a "Y" or "N"), a message sent to a predetermined short code, a WAP-Push link, an IVR (Interactive Voice Response) session, a link or communication to a phone number, or other method. Responses are processed by the wireless messaging platform and secondary database system and stored for compilation and analysis. The stored data may then be transformed into a graphical or other format and accessed through the user interface for viewing and interpretation of actual versus perceived compliance with that prescription drug treatment.

The health care assistance and emergency notification systems are intended to assist individuals who are having adverse medical reactions by providing emergency support in the form of family, health care professional, and location-based emergency medical service support.

For example, in the case of real-time health care assistance, a user may initiate the notification service by sending an MO-based message with a specific character/key rely, message to a specific short code, initiating an IVR session through an embedded phone number, or using WAP-Push to enter IP-based data. The secondary database system and wireless messaging platform can process the data and enable several options including: (i) having their selected physician notified of the event, (ii) notifying their selected emergency contact, or (iii) notifying selected third parties such as family members. Notification may take the form of an automated call, email, wireless message, or other communication, and contacted parties may be provided with information on the user and their prescription and dosing information, in order to streamline assistance for the user.

In the case of emergency medical service notification, in addition to the processes and notifications carried out for health care assistance, the system may also notify location-based real-time emergency medical services that emergency assistance is required. The integration of the system with the user's mobile phone provides for added mobile functionality through the use of RTLS (real-time location services). RTLS are a new breed of wireless network service that integrate location tracking capabilities with existing 802.11 (Wi-Fi) wireless networks to allow real-time location of users wherever wireless network coverage is provided. Systems such as the Cisco 2700 Wireless Location Appliance or the Ekahau Positioning Engine can display the location of wireless devices, laptops, PDAs or any item carrying an radio frequency identification (RFID) tag or Wi-Fi tag, on screen, graphically, and in real-time. By using these resources, an EMS response can be initiated and dispatched in real-time according to the precise location of the mobile individual.

Figure 10:
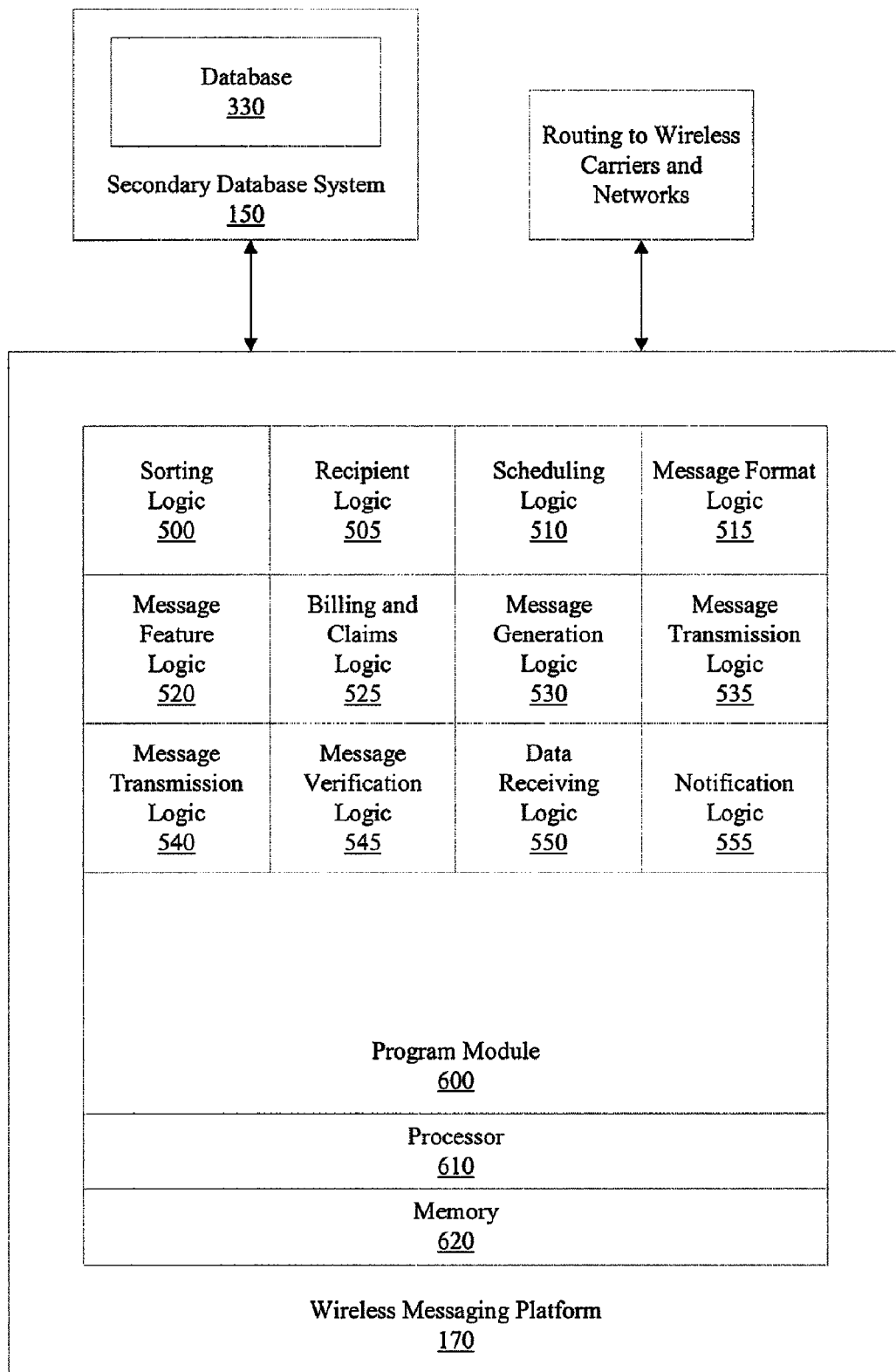
FIG. 10 is a block diagram of an exemplary wireless messaging platform and method for a program module in accordance with the present invention.

FIG. 10 is a block diagram of an exemplary wireless messaging platform in accordance with the present invention. The wireless messaging platform 170 is comprised of a program module 600, processor 610, and memory 620. Program module 600 includes Logic 500-550. Logic 500-550 can be processor 610 executable code loaded from memory 620. This processor-executable code can be part of a single executable program or can be components of a number of different executable programs. Program module 600 (i) encapsulates information such as data fields, database content, Web content, Java classes, EJBs (Enterprise Java Beans), PL/SQL (Procedural Language/Structural Query Language) procedures, or other applications from the secondary database system 150, (ii) has an execution flow that can handle events, transformations, and conditional logic, (iii) and processes, executes, routes, and transmits formatted wireless message content using Logic 500-550.

Specifically, sorting logic 500 sorts specified parameters in the user's account within the secondary database 330 including time, time zone, user name, output data fields, and others. Recipient logic 505 determines the message recipients, including names, phone numbers, email addresses, and other contact details from the user's account in the secondary database 330. Scheduling logic 510 sorts and queues the message order based on a predetermined time to transmission and other settings. Message format logic 515 selects the user's message format based on data outputs, interface selections, and/or device selections stored in the user's account within the secondary database 330. Message content, inclusions, and limitations are determined by message format and corresponding parameters stored in the user's account within the secondary database 330. Message feature logic 520 incorporates two-way messaging, reply options, and health care assistance and EMS buttons or reply options into message content or features, based on settings in the user's account within the secondary database 330. Billing and claims logic 525 determines processes for billing, including the user's wireless account, other recipient's wireless account, or other billing and claims methods based on settings in the user's account within the secondary database 330. Message generation logic 530 processes and generates wireless messages based on data and content in the user's account within the secondary database 330. Message generation logic 530 determines alphanumeric limitations associated with device displays, message format, and other parameters, and may create concatenated or additional messages based on the data needed to complete the transmission. Message transmission logic 535 formats the data into packets and transmits and distributes messages via a modem, ISDN-device, wireless network device, TCP/IP connection, or other method. Message routing logic 540 routes messages through wireless carriers and networks to the end users. Application content can connect to the wireless network operator via a fixed wire-line or wireless network interface using protocols like short message peer-to-peer (SMPP), external machine interface/universal computer protocol (EMI/UCP), computer interface to message distribution (CIMD), and open interface specification (OIS), which are then connected to either a short message service centre (SMSC), messaging gateway, or content aggregator. To better handle volume, message handling and processing may make use of an always up-to-date (AUTD) server, batch loader, or other bulk message processing/queuing system. Message verification logic 545 verifies message delivery, receipt, time of receipt, and other information from the SMSC and wireless carrier corresponding to the individual's wireless service. Message verification logic 545 also processes and stores said data on the secondary database 330 for billing and claims. Data receiving logic 550 receives and processes user data from MO replies, two-way data transfers, IVR sessions, short code messages, and other methods into the secondary database system 150 for storage or processing. Notification logic 555 processes data transfers and system notification responses in conjunction with the secondary database system 150. Notification logic 555 then (i) determines contacts and content for notifications from secondary database 330 output parameters, (ii) formats, generates, transmits, routes, and verifies notification messages or other communications in a form similar to the one described above herein, and (iii) incorporates pertinent user data and content into those notifications including user name, drug name, dose, time taken, RTLS location, or other information.

The wireless messaging platform 170 is functionally integrated with the secondary database system 150 and is directly and/or indirectly integrated with the wireless carriers and wireless networks, which route, transmit, and deliver mobile content to wireless subscribers.

The wireless messaging platform may be integrated with the secondary database system and use different APIs or layers such as Web Services, SOAP, Java 2 platform micro edition (J2ME), distributed component object model (DCOM), Java remote method invocation (RMI), CORBA, WAP, BREW, Java mobile information device profile (Java MIDP), computer interface to message distribution (CIMD), XML-RPC, and others. The data from the secondary database system is made accessible to these APIs through a variety of API interfaces and communication layers such as HTTP, SMPP, SMTP, FTP, XML, .NET, COM Object, RPC, SOA, REST, and others.

There are a number of software alternatives which define the API, communication protocol, and object/service information models that then enable applications running on various platforms to interoperate. Most wireless platforms now employ wireless open standard protocols and technologies on some level. Open standards such as short message peer-to-peer (SMPP), hyper text transfer protocol (HTTP), simple mail transfer protocol (SMTP), Extensible Markup Language (XML), Web Services, and SOAP are publicly available and implementable standards which enable development and integration regardless of the underlying type of software or hardware. There are a number of different ways to blend and implement both open standard and proprietary architectures. For example, different products and platforms may be created by combining APIs or API layers, API interfaces, linked programming languages, and security implementations, and by introducing other SOA, EAI, and EII components into the platform. One example of such an implementation would be an open source implementation of a two-way SOAP to CORBA bridge.

One sample open standard API protocol is Web Services, which may be used to generate and process the user-based prescription content used in the wireless prescription reminders. Web Services may be implemented using a variety of communications protocols and architectures including remote procedure call (RPC), service-oriented architectures (SOA), and representational state transfer (REST). There are a number of core specifications which may be selected, modified, or substituted based on the underlying technologies or other specifications.

In one embodiment, SOAP forms the foundation layer of the Web Services stack, providing a basic messaging framework which more abstract layers can build on. SOAP uses an XML-based, extensible message envelope format, with "bindings" to underlying protocols (e.g., HTTP, SMTP, TCP/IP, and XMPP). The Web service may use Web Services description language (WSDL), an XML-based service description on how to communicate using the web service and specifying the protocol bindings and message formats required to interact with the web services listed in its directory. Special datatypes may be embedded in the WSDL file in the form of XML Schema. Web services typically use a universal description, discovery, and integration (UDDI) registry, which is designed to be interrogated by SOAP messages and to provide access to WSDL documents describing the protocol bindings and message formats required to interact with the web services listed in its directory. To create secure communications, a Web Service security (WSS) communications protocol contains specifications on how integrity and confidentiality can be enforced on Web Services messaging. It defines how to use XML encryption and XML signatures in SOAP to secure message exchanges. Integrity and confidentiality can also be enforced through the use of a transport security layer (TLS). Lastly, the Web Service uses a Web Services-reliable exchange protocol for reliable messaging between two Web Services. There are a number of organizations such as OASIS, W3C, and WS-I which define and provide standards and specifications Web Services and Web Services messaging.

Other alternatives to SOAP in the WS Stack include: XML remote procedure call protocol (XML-RPC), JavaScript object notation RPC (JSON-RPC), XML interface for network services (XINS), Burlap, Global XML Web Services architecture (GXA), Hessian Web Service Protocol, representational state transfer (REST), plain old XML-over-HTTP (POX/HTTP), Modbus, and blocks extensible exchange protocol (BEEP), among others.

In terms of messaging and network compatibility, SMS is currently transmitted over the GSM network, while EMS is available on the CDMA, TDMA, and GSM networks. Transmission of SMS and EMS between the SMSC and mobile device can be done through different protocols such as the traditional circuit based SS7 network within the GSM MAP framework or TCP/IP within the same standard. MMS is designed to work with mobile packet data services such as GPRS, EDGE, or CDMA2000, although some control messages may still traverse the SS7 signaling network. WAP and WAP-Push are designed to operate on competing networks such as GSM and CDMA. SMS is used as a transport to implement the WAP stack on top of the SMSC bear. BREW is air-interface independent and supported by GSM/GPRS, UMTS/3GSM, and CDMA. SIP is a protocol which defines a method of passing instant messages between endpoints, similar to SMS. SIP is a peer-to-peer protocol and requires a simple core network, distributed to the networked edge, and embedded in endpoints. Newer versions of IM are enabling real-time text-based communication to take place over various wireless networks, instead of the just over the Internet. Messaging compatibility with wireless networks will continue to evolve as handsets and systems are upgraded from 2G to 3G and 3.5G networks such as W-CDMA, HSPDA, and HSUPA.

In the future, wireless messaging architectures will migrate toward 3G all IP-based infrastructures as wireless messaging traffic and the need for bandwidth increases. Future alternatives will include (i) the use of Signaling Transport (SIGTRAN) technology with translation protocol layers to take traditional SS7 traffic from a circuit-based network to a packet-based IP network, and (ii) use of a first delivery attempt (FDA) at the edge of the mobile network, providing a message-handling function where SMS traffic is intercepted, offloaded from the SS7 network, and delivered using IP-based massaging protocols.

The wireless messaging platform's ultimate function is to provide users with automated, real-time wireless prescription dosing reminders and networked services to assist users with prescription management and compliance. This would not be possible without the integration of the various components which comprise this system framework.

The foregoing disclosure, system configuration, and methods for integrating system components has been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An integrated prescription management and compliance system comprising:

at least one primary health care database containing user-specific prescription medication data for one or more individuals selected from the group consisting of one or more pharmacies, pharmacy benefit managers (PBM), health insurance companies, National Council for Prescription Drug Program (NCPDP) database providers, electronic health record (EHR) providers, and other primary health care databases containing user-specific prescription medication data for one or more individuals stored or hosted on at least one primary health care computer server and connected to one or more networks;

a secondary database system comprising at least one database, database management system, program module, application program, and algorithm stored or hosted on at least one computer server and connected via one or more networks and integrated with a user interface, a wireless messaging platform, and at least one primary health care database or primary health care computer server that (i) enables one or more individuals to create and access user accounts in conjunction with a user interface Web application, WAP application, or mobile application, (ii) enables users to access a user account set up algorithm which requires each user to enter, scan in, or otherwise specify at least their schedule data, current time zone, wireless phone number or wireless device identifier, and one or more personal identifiers, primary health care account identifiers, or combinations thereof into their user account to complete the algorithm, (iii) utilizes the personal identifiers, primary health care account identifiers, or combinations thereof specified in each user account as part of the user account set up algorithm to execute user authentication and authorization processes with at least one primary health care database or primary health care computer server and uploads, processes, and stores user-specific prescription medication data from at least one primary health care database or primary health care computer server into the secondary database system and each user account, (iv) enables each user to select prescription medications in their user account for further system use from among all prescription medications uploaded or added to their user account, (v) enables each user to enter, scan in, select, or otherwise specify data in their user account and combine this data with the user-specific prescription medication data uploaded or added to their user account, (vi) utilizes data entered, scanned in, or otherwise specified by each user as part of the user account set up algorithm to perform calculations for each user and configure user-specific system settings, (vii) calculates a user and time-specific medication dosing regimen for each prescription medication selected in each user account using a medication dosing regimen formula, one or more schedule variables selected from the schedule data each user specifies in their user account as part of the user account set up algorithm, and one or more dosage variables selected from the user-specific prescription medication data for each prescription medication in each user account, (viii) generates user and time-specific medication dosing instructions for each dose of prescription medication based on the user and time-specific medication dosing regimen calculated by the system for that user and prescription medication, (ix) enables each user to optionally enhance their user and time-specific medication dosing instructions with a medication image, Internet medication link, Internet treatment link, advertisement, or logo based on user account selections made via the user interface, and (x) makes said user and time-specific medication dosing instructions and other user account data available to the wireless messaging platform;

a user interface comprising at least one Web application, WAP application, mobile application, or combination thereof stored or hosted on at least one computer server, connected via one or more networks and integrated with the secondary database system, and accessible to users via at least one Web site, WAP site, mobile site, or combination thereof over one or more networks which, in conjunction with the secondary database system, (i) enables one or more individuals to create user accounts, (ii) enables users to enter, scan in, select, or otherwise specify data in their user accounts, (iii) enables users to access, view, and modify data in their user accounts, and (iv) enables users to access a user account set up algorithm which requires each user to enter, scan in, or otherwise specify data items in their user account which are then used by the secondary database system to perform calculations for each user and configure user-specific system settings;

a wireless messaging platform comprising at least one database, program module, and application program stored or hosted on at least one computer server, connected via one or more networks and integrated with the secondary database system, and connected via one or more networks to one or more wireless carriers or wireless messaging gateways which (i) determines message recipients, formats, and schedules data-based messages containing the user and time-specific medication dosing instructions generated by the system utilizing user account data including each user's current time zone and specified wireless phone number or wireless device identifier, and (ii) transmits said data-based messages containing user and time-specific medication dosing instructions over one or more networks to one or more wireless carriers or wireless messaging gateways for wireless delivery over one or more wireless networks to each user at system-determined medication dose times on each user's wireless phone, Smartphone, personal digital assistant (PDA), wireless device, or combinations thereof via Short Message Service (SMS), Enhanced Message Service (EMS), Multimedia Message Service (MMS), Wireless Application Protocol Push (WAP-Push), Binary Runtime Environment for Wireless (BREW), Instant Message (IM), Session Initiation Protocol (SIP), email, or combinations thereof.

2. The system of claim 1 wherein the user interface and secondary database system enable individuals including parents and legal guardians to create user accounts for their children, spouses, legal dependents, or combinations thereof, also defined as system users, and perform requisite user actions on each child's, spouse's, or legal dependent's behalf.

3. The system of claim 1 wherein the data-based messages containing user and time-specific medication dosing instructions include at least the (i) user's name, (ii) dose time, (iii) prescription medication name, and (iv) number and type of units of prescription medication to be taken at that dose time including the prescribed unit dose, the prescribed volume of drug in solution, or the prescribed number of dosage forms.

4. The system of claim 1 wherein the user account set up algorithm requires users to digitally sign electronic legal documents in order to authorize and upload their electronic user-specific prescription medication data into their user account from at least one primary health care database or primary health care computer server under the Health Insurance Portability and Accountability Act (HIPAA).

5. The system of claim 1 wherein the user interface and secondary database system enable individuals including parents and legal guardians to create user accounts and perform requisite user actions on behalf of their children, spouses, legal dependents, or combinations thereof, also defined as system users, and wherein the user account set up algorithm requires said individuals, children, spouses, or legal dependents to digitally sign electronic legal documents in order to authorize and upload each child's, spouse's, or legal dependent's electronic user-specific prescription medication data from at least one primary health care database or primary health care computer server into each respective child's, spouse's, or legal dependent's user account under the Health Insurance Portability and Accountability Act (HIPAA).

6. The system of claim 1 wherein user accounts enable users to sign electronic legal documents authorizing the distribution of their electronic user-specific prescription medication data to third party individuals under the Health Insurance Portability and Accountability Act.

7. The system of claim 1 wherein data required to be entered, scanned in, or otherwise specified in each user account for completion of the user account set up algorithm includes at least each user's (i) account username/email address and account password, (ii) one or more personal identifiers, primary health care account identifiers, or combinations thereof selected from the group consisting of each user's name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, and prescription medication barcodes, (iii) schedule data including weekday and weekend wake times, weekday and weekend bed times, weekday and weekend breakfast times, weekday and weekend lunch times, and weekday and weekend dinner times, (iv) current time zone, and (v) wireless phone number or wireless device identifier.

8. The system of claim 1 wherein data required to be entered, scanned in, or otherwise specified in each user account for completion of the user account set up algorithm includes at least each user's (i) account username/email address and account password, (ii) one or more personal identifiers, primary health care account identifiers, or combinations thereof selected from the group consisting of each user's name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, and prescription medication barcodes, (iii) schedule data including wake time, bed time, breakfast time, lunch time, and dinner time, (iv) current time zone, and (v) wireless phone number or wireless device identifier.

9. The system of claim 1 wherein the user interface and secondary database system enable individuals including parents and legal guardians to create user accounts and perform requisite user actions on behalf of their children, spouses, legal dependents, or combinations thereof, also defined as system users, and wherein data required to be entered, scanned in, or otherwise specified in each child's, spouse's, or legal dependent's user account for completion of the user account set up algorithm includes at least (i) an account username/email address and account password, (ii) one or more personal identifiers, primary health care account identifiers, or combinations thereof selected from the group consisting of each child's, spouse's, or legal dependent's name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, and prescription medication barcodes, (iii) schedule data including weekday and weekend wake times, weekday and weekend bed times, weekday and weekend breakfast times, weekday and weekend lunch times, and weekday and weekend dinner times, (iv) current time zone, and (v) at least one wireless phone number or wireless device identifier for the individual, parent, legal guardian, child, spouse, legal dependent, or combination thereof.

10. The system of claim 1 wherein the user interface and secondary database system enable individuals including parents and legal guardians to create user accounts and perform requisite user actions on behalf of their children, spouses, legal dependents, or combinations thereof, also defined as system users, and wherein data required to be entered, scanned in, or otherwise specified in each child's, spouse's, or legal dependent's user account for completion of the user account set up algorithm includes at least (i) an account username/email address and account password, (ii) one or more personal identifiers, primary health care account identifiers, or combinations thereof selected from the group consisting of each child's, spouse's, or legal dependent's name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, and prescription medication barcodes, (iii) schedule data including a wake time, bed time, breakfast time, lunch time, and dinner time, (iv) current time zone, and (v) at least one wireless phone number or wireless device identifier for the individual, parent, legal guardian, child, spouse, legal dependent, or combination thereof.

11. The system of claim 1 wherein the user account set up algorithm enables users to select one or more defaults for requisite algorithm data fields including weekday and weekend wake times, weekday and weekend bed times, weekday and weekend breakfast times, weekday and weekend lunch times, weekday and weekend dinner times, time zone, wireless message format, and which wireless phone, health insurance, bank, or credit card account to bill for wireless messaging charges, thereby prompting the system to determine the data item used for that algorithm data field instead of the user.

12. The system of claim 1 wherein the user interface and secondary database system enable individuals including parents and legal guardians to create user accounts and perform requisite user actions on behalf of their children, spouses, legal dependents, or combinations thereof, also defined as system users, and wherein the user account set up algorithm enables users to select one or more defaults for requisite algorithm data fields including weekday and weekend wake times, weekday and weekend bed times, weekday and weekend breakfast times, weekday and weekend lunch times, weekday and weekend dinner times, time zone, wireless message format, and which wireless phone, health insurance, bank, or credit card account to bill for wireless messaging charges, thereby prompting the system to determine the data item used for that algorithm data field instead of the user.

13. The system of claim 1 wherein the secondary database system utilizes one or more secondary database system identifiers including a system Federal Employer Identification Number (FEIN) and one or more user personal identifiers, user primary health care account identifiers, or combinations thereof selected from the group consisting of each user's name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, and prescription medication barcodes entered, scanned in, or otherwise specified in each user account as part of the user account set up algorithm to authenticate the system and each user against at least one primary health care database or primary health care computer server and authorize and upload user-specific prescription medication data from said primary health care database or primary health care computer server into the secondary database system and each user account.

14. The system of claim 1 wherein the user interface and secondary database system enable individuals including parents and legal guardians to create user accounts and perform requisite user actions on behalf of their children, spouses, legal dependents, or combinations thereof, also defined as system users, and wherein the secondary database system utilizes secondary database system identifiers including a system Federal Employer Identification Number (FEIN) and one or more user personal identifiers, user primary health care account identifiers, or combinations thereof selected from the group consisting of each child's, spouse's, or legal dependent's name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, and prescription medication barcodes entered, scanned in, or otherwise specified in each child's, spouse's, or legal dependent's user account as part of the user account set up algorithm to authenticate the system and each child, spouse, or legal dependent against at least one primary health care database or primary health care network sever computer and authorize and upload each child's, spouse's, or legal dependent's user-specific prescription medication data from said primary health care database or primary health care computer server into the secondary database system and each respective user account.

15. The system of claim 1 wherein the secondary database system automatically updates the user-specific prescription medication data uploaded into each user account from each respective primary health care database or primary health care computer server and modifies each user and time-specific medication dosing regimen, user and time-specific medication dosing instruction, and related data-based messages containing user and time-specific dosing instructions to reflect any changes in each user's underlying user-specific prescription medication data from at least one primary health care database.

16. The system of claim 1 wherein the user interface and secondary database system enable individuals to create user accounts for their children, spouses, legal dependents, or combinations thereof, also defined as system users, and wherein the secondary database system automatically updates the user-specific prescription medication data uploaded into each child's, spouse's, or legal dependent's user account from each respective primary health care database or primary health care computer server and modifies each child's, spouse's, or legal dependent's user and time-specific medication dosing regimens, user and time-specific medication dosing instructions, and related data-based messages containing user and time-specific dosing instructions to reflect any changes in the underlying user-specific prescription medication data from at least one primary health care database.

17. The system of claim 1 wherein data entered, scanned in, modified, or otherwise specified in each user account can include each user's first and last name, birth date, weight, gender, ethnicity, country, address, language, social security number, email address, account username, account password, name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, prescription medication identifiers including each medication's brand name, scientific name, generic name, National Drug Code, prescription number, prescription barcode, prescription medication barcode, and universal product code, prescription medication dosage data including each medication's prescribed dosage, number and type of units per dose, unit dose, volume of drug in solution, dosage form, route of administration, sig codes, additional dosing indications, quantity in terms of number of units, and quantity in terms of number of days of supply, medication order dates, medication expiration dates, dates medications were dispensed, refill dates, prescribing physician names, prescribing physician identification numbers, prescribing physician addresses and telephone numbers, alternative medications including over-the-counter medications, vitamins, supplements, and herbal medications and their respective brand names, scientific names, barcodes, universal product codes, dosages, number and type of units per dose, unit doses, volume of drug in solution, dosage forms, routes of administration, sig codes, additional dosing indications, quantity in terms of number units, and quantity in terms of number of days of supply, medical conditions associated with each prescription or alternative medication, medical treatments associated with each prescription or alternative medication, prescription medications and related dosage data selected for further system use from among all prescription medications uploaded, scanned in, or entered into user accounts, alternative medications and related dosage data selected for further system use from among all alternative medications entered or scanned into user accounts, user-specific prescription medication data including prescription medication names, National Drug Codes, prescription numbers, prescription barcodes, prescription medication barcodes, dosages, number and type of units per dose, unit doses, volume of drug in solution, dosage forms, routes of administration, sig codes, additional dosing indications, quantity in terms of number units, and quantity in terms of number of days of supply, weekday and weekend wake times, weekday and weekend bed times, weekday and weekend breakfast times, weekday and weekend lunch times, weekday and weekend dinner times, current time zone, wireless phone number, wireless device identifier, name of wireless carrier, wireless phone brand, wireless device brand, wireless handset model, wireless device model, bank account number, credit card number, billing address, preferred payment method, digital signature for electronic legal documents, emergency medical contact information including names and telephone numbers, selections to add medication images, Internet medication links, Internet treatment links, prescription pricing comparisons, advertisements, logos, audio files, or video files to user and time-specific medication dosing instructions, or any combination thereof.

18. The system of claim 1 wherein the user interface and secondary database system enable individuals to create user accounts and perform requisite user actions on behalf of their children, spouses, legal dependents, or combinations thereof, also defined as system users, and wherein data entered, scanned in, modified, or otherwise specified in each child's, spouse's, or legal dependent's user account can include each child's, spouse's, or legal dependent's first and last name, birth date, weight, gender, country, address, language, social security number, email address, account username, account password, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, prescription medication identifiers including each medication's brand name, scientific name, generic name, National Drug Code, prescription number, prescription barcode, prescription medication barcode, and universal product code, prescription medication dosage data including each medication's prescribed dosage, number and type of units per dose, unit dose, volume of drug in solution, dosage form, route of administration, sig codes, additional dosing indications, quantity in terms of number of units, and quantity in terms of number of days of supply, medication order dates, medication expiration dates, dates medications were dispensed, refill dates, prescribing physician names, prescribing physician identification numbers, prescribing physician addresses and telephone numbers, alternative medications including over-the-counter medications, vitamins, supplements, and herbal medications and their respective brand names, scientific names, dosages, number and type of units per dose, unit doses, dosage forms, volume of drug in solution, routes of administration, sig codes, additional dosing indications, barcodes, universal product codes, quantity in terms of number of units, and quantity in terms of number of days of supply, medical conditions associated with each prescription or alternative medication, medical treatments associated with each prescription or alternative medication, prescription medications and related dosage data selected for further system use from among all prescription medications uploaded, scanned in, or entered into user accounts, alternative medications and related dosage data selected for further system use from among all alternative medications entered or scanned into user accounts, user-specific prescription medication data including prescription medication names, National Drug Codes, prescription numbers, prescription barcodes, prescription medication barcodes, universal product codes, dosages, number and type of units per dose, unit doses, dosage forms, volume of drug in solution, routes of administration, sig codes, additional dosing indications, quantity in terms of number of units, and quantity in terms of number of days of supply, weekday and weekend wake times, weekday and weekend bed times, weekday and weekend breakfast times, weekday and weekend lunch times, weekday and weekend dinner times, current time zone, wireless phone number, wireless device identifier, name of wireless carrier, wireless phone brand, wireless device brand, wireless handset model, wireless device model, bank account number, credit card number, billing address, preferred billing and payment method, digital signature for electronic legal documents, emergency medical contact information including names and telephone numbers, selections to add medication images, Internet medication links, Internet treatment links, prescription pricing comparisons, advertisements, corporate logos, audio files, or video files to user and time-specific medication dosing instructions, or combinations thereof.

19. The system of claim 1 wherein user-specific prescription medication data required to calculate user and time-specific medication dosing regimens and uploaded into each user account from at least one primary health care database or primary health care computer server or entered, scanned in, modified, or otherwise specified by each user in each user account includes at least (i) a prescription medication identifier including the medication name, National Drug Code (NDC), prescription barcode, prescription medication barcode, or universal product code for each medication prescribed to each user, (ii) the prescribed number and type of units per dose including the unit dose, the volume of drug solution, or the number of dosage forms for each medication prescribed to each user, and (iii) the prescribed dosage for each medication prescribed to each user, wherein dosage comprises at least the prescribed dose and frequency and can also include duration, route of administration, and additional sig codes and dosing indications.

20. The system of claim 1 wherein the user interface and secondary database system enable individuals to create user accounts and perform requisite user actions on behalf of their children, spouses, legal dependents, or combinations thereof, also defined as system users, and wherein user-specific prescription medication data required to calculate user and time-specific medication dosing regimens and uploaded into each user account from at least one primary health care database or primary health care computer server or entered, scanned in, modified, or otherwise specified by each user in each user account includes at least (i) a prescription medication identifier including the medication name, National Drug Code (NDC), prescription barcode, prescription medication barcode, or universal product code for each medication prescribed to each child, spouse, or legal dependent, (ii) the prescribed number and type of units per dose including the unit dose, the volume of drug solution, or the number of dosage forms for each medication prescribed to each child, spouse, or legal dependent, and (iii) the prescribed dosage for each medication prescribed to each child, spouse, or legal dependent, wherein dosage comprises at least the prescribed dose and frequency and can also include duration, route of administration, and additional sig codes and dosing indications.

21. The system of claim 1 wherein user-specific prescription medication data uploaded into each user account from at least one primary health care database or primary health care computer server can include each user's first and last name, birth date, age, gender, weight, ethnicity, address, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, prescription medication identifiers including each medication's brand name, generic name, scientific name, National Drug Code, prescription number, prescription barcode, prescription medication barcode, and universal product code, prescribed dosage data including each medication's dosage, number and type of units per dose, unit dose, volume of drug in solution, dosage form, routes of administration, sig codes, additional dosing indications, quantity of medication in terms of number of units, quantity of medication in terms of number of days of supply, substitutions made for the aforementioned data, generic drug substitutes, interaction warnings, date dispensed, refill date, prescription order date, medication expiration date, medication refill number, and indication of retail or mail order purchase for each medication prescribed to each user, prescription drug prices, prescription drug wholesale prices, generic drug prices, price comparisons, prescription medication images, Internet medication links, Internet treatment links, prescription pricing comparisons, advertisements, logos, prescribing physician names, prescribing physician identification numbers, prescribing physician addresses and telephone numbers, and medical conditions or medical treatments associated with each medication prescribed to each user.

22. The system of claim 1 wherein the user interface and secondary database system enable individuals to create user accounts and perform requisite user actions on behalf of their children, spouses, legal dependents, or combinations thereof, also defined as system users, and wherein user-specific prescription medication data uploaded into each user account from at least one primary health care database or primary health care computer server can include each child's, spouse's, or legal dependent's first and last name, birth date, age, gender, weight, ethnicity, address, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, prescription medication identifiers including each medication's brand name, generic name, scientific name, National Drug Code, prescription number, prescription barcode, prescription medication barcode, and universal product code, prescribed dosage data including each medication's dosage, number and type of units per dose, unit dose, volume of drug in solution, dosage form, route of administration, sig codes, additional dosing indications, quantity of medication in terms of number of units, quantity of medication in terms of number of days of supply, substitutions made for the aforementioned data, generic drug substitutes, interaction warnings, date dispensed, refill date, prescription order date, medication expiration date, medication refill number, and indication of retail or mail order purchase for each medication prescribed to each child, spouse, or legal dependent, prescription drug prices, prescription drug wholesale prices, generic drug prices, price comparisons, prescription medication images, Internet medication links, Internet treatment links, prescription pricing comparisons, advertisements, logos, prescribing physician names, prescribing physician identification numbers, prescribing physician addresses and telephone numbers, and medical conditions or medical treatments associated with each medication prescribed to each child, spouse, or legal dependent.

23. The system of claim 1 wherein (i) the user account set up algorithm requires that each user enter or specify schedule data including their weekday and weekend wake times, weekday and weekend bed times, weekday and weekend breakfast times, weekday and weekend lunch times, and weekday and weekend dinner times into their user account to complete the algorithm, (ii) the user account set up algorithm requires that each user enter, scan in, or specify one or more personal identifiers, primary health care account identifiers, or combinations thereof selected from the group consisting of their name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, prescription medication barcodes, and universal product codes into their user account to complete the algorithm, (iii) user-specific prescription medication data uploaded into each user account from at least one primary health care database/primary health care computer server or entered, scanned in, modified, or otherwise specified by each user in each user account includes one or more prescription medication identifiers selected from the group consisting of prescription medication brand names, prescription medication generic names, prescription medication scientific names, National Drug Codes, prescription numbers, prescription barcodes, and prescription medication barcodes for each medication, each medication's prescribed dosage, and each medication's prescribed number and type of units per dose including the unit dose, the volume of drug in solution, or the number of dosage forms, (iv) user-specific prescription medication data uploaded into each user account from at least one primary health care database/primary health care computer server or entered, scanned in, modified, or otherwise specified by each user in each user account can include optional dosage data including routes of administration, sig codes, additional dosing indications, quantity of medication in number of units, quantity of medication in number of days of supply, prescription medication order dates, prescription medication refill dates, the dates prescription medications were dispensed, prescription medication images, Internet prescription medication links, Internet treatment links, and interaction warnings for each medication prescribed to each user, and (v) the secondary database system calculates a user and time-specific medication dosing regimen for each prescription medication selected in each user account using one or more schedule variables selected from the schedule data in each user account, one or more dosage variables selected from the user-specific prescription medication data in each user account including at least the prescribed dosage and prescribed number and type of units per dose for each prescription medication, and a medication dosing regimen formula selected from the group consisting of "once in the morning" or "once a day" medication dosing regimens calculated by setting the dose times to each user's specified weekday and weekend wake times, weekday and weekend wake times plus an additional time interval, or weekday and weekend breakfast times, "once before bed" or "once at night" medication dosing regimens calculated by setting the dose times to each user's specified weekday and weekend bed times, weekday and weekend bed times minus an additional time interval, or weekday and weekend dinner times, "dosing with meals" medication dosing regimens calculated by setting the dose times to each user's specified weekday and weekend breakfast, lunch, and dinner times or weekday and weekend breakfast, lunch, and dinner times plus or minus an additional time interval, "dosing before meals" medication dosing regimens calculated by setting the dose times to each user's specified weekday and weekend breakfast, lunch, and dinner times minus an additional time interval, "dosing after meals" medication dosing regimens calculated by setting the dose times to each user's specified weekday and weekend breakfast, lunch, and dinner times plus an additional time interval, "dosing 'n' times per day" medication dosing regimens calculated by setting the first dose to each user's specified weekday and weekend wake times, weekday and weekend wake times plus an additional time interval, or weekday and weekend breakfast times, setting the final dose to each user's specified weekday and weekend bed times, weekday and weekend bed times minus an additional time interval, or weekday and weekend dinner times, and calculating additional dose times by dividing the number of remaining hours in each user's weekday and weekend day by 'n–1' and setting additional dose times at each time interval other than the first or final dose times, "dosing every 'n' hours" medication dosing regimens calculated by starting the calculations and setting the first dose to each user's specified weekday and weekend wake times, weekday and weekend wake times plus an additional time interval, or weekday and weekend breakfast times, setting subsequent dose times every 'n' hours after each start time, and stopping the calculations at each user's specified weekday and weekend bed times or continuing the calculation throughout subsequent 24 hour periods, "medications prescribed to be taken with a dose of another medication" dosing regimens calculated by linking the dependent medication's dosing indications to those calculated for the primary medication in each user account, "every other day" medication dosings regimens calculated by setting the dose times to each user's specified weekday and weekend wake times, weekday and weekend wake times plus an additional time interval, or weekday and weekend breakfast times and alternating the daily dosing events, "once a week, once every two weeks, or once a month" medication dosing regimens calculated by enabling each user to select their preferred time and day the dose is to be taken and setting subsequent dose times on a weekly, bi-weekly, or monthly basis, and any other medication dosing regimen formula calculated using one or more schedule variables selected from the schedule data in each user account, optional lead time variables for those schedule events, one or more dosage variables selected from the user-specific prescription medication data in each user account, and optional user-specific variables from each user account including each user's age, weight, or gender.

24. The system of claim 1 wherein (i) the user interface and secondary database system enable individuals including parents and legal guardians to create user accounts and perform requisite user actions on behalf of their children, spouses, legal dependents, or combinations thereof, also defined as system users, (ii) the user account set up algorithm requires that each user enter or specify schedule data including weekday and weekend wake times, weekday and weekend bed times, weekday and weekend breakfast times, weekday and weekend lunch times, and weekday and weekend dinner times into each child's, spouse's, or legal dependent's user account to complete the algorithm, (iii) the user account set up algorithm requires that each user enter, scan in, or otherwise specify one or more personal identifiers, primary health care account identifiers, or combinations thereof selected from the group consisting of each child's, spouse's, or legal dependent's name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, prescription medication barcodes, and universal product codes into each child's, spouse's, or legal dependent's user account to complete the algorithm, (iv) user-specific prescription medication data uploaded into each child's, spouse's, or legal dependent's user account from at least one primary health care database/primary health care computer server or entered, scanned in, modified, or otherwise specified by each user in each child's, spouse's, or legal dependent's user account includes one or more prescription medication identifiers selected from the group consisting of prescription medication brand names, prescription medication generic names, prescription medication scientific names, National Drug Codes, prescription numbers, prescription barcodes, and prescription medication barcodes for each medication, each medication's prescribed dosage, and each medication's prescribed number and type of units per dose including the unit dose, the volume of drug in solution, or the number of dosage forms, (v) user-specific prescription medication data uploaded into each child's, spouse's, or legal dependent's user account from at least one primary health care database/primary health care computer server or entered, scanned in, modified, or otherwise specified by each user in each child's, spouse's, or legal dependent's user account can include optional dosage data including routes of administration, sig codes, additional dosing indications, quantity of medication in number of units, quantity of medication in number of days of supply, prescription medication order dates, prescription medication refill dates, the dates prescription medications were dispensed, prescription medication images, Internet prescription medication links, Internet treatment links, and interaction warnings for each medication prescribed to each child, spouse, or legal dependent, and (vi) the secondary database system calculates a user and time-specific medication dosing regimen for each prescription medication selected in each child's, spouse's, or legal dependent's user account using one or more schedule variables selected from the schedule data in each child's, spouse's, or legal dependent's user account, one or more dosage variables selected from the user-specific prescription medication data in each child's, spouse's, or legal dependent's user account including at least the prescribed dosage and prescribed number and type of units per dose for each prescription medication, and a medication dosing regimen formula selected from the group consisting of "once in the morning" or "once a day" medication dosing regimens calculated by setting the dose times to each user's specified weekday and weekend wake times, weekday and weekend wake times plus an additional time interval, or weekday and weekend breakfast times, "once before bed" or "once at night" medication dosing regimens calculated by setting the dose times to each user's specified weekday and weekend bed times, weekday and weekend bed times minus an additional time interval, or weekday and weekend dinner times, "dosing with meals" medication dosing regimens calculated by setting the dose times to each user's specified weekday and weekend breakfast, lunch, and dinner times or weekday and weekend breakfast, lunch, and dinner times plus or minus an additional time interval, "dosing before meals" medication dosing regimens calculated by setting the dose times to each user's specified weekday and weekend breakfast, lunch, and dinner times minus an additional time interval, "dosing after meals" medication dosing regimens calculated by setting the dose times to each user's specified weekday and weekend breakfast, lunch, and dinner times plus an additional time interval, "dosing 'n' times per day" medication dosing regimens calculated by setting the first dose to each user's specified weekday and weekend wake times, weekday and weekend wake times plus an additional time interval, or weekday and weekend breakfast times, setting the final dose to each user's specified weekday and weekend bed times, weekday and weekend bed times minus an additional time interval, or weekday and weekend dinner times, and calculating additional dose times by dividing the number of remaining hours in each user's weekday and weekend day by 'n–1' and setting additional dose times at each time interval other than the first or final dose times, "dosing every 'n' hours" medication dosing regimens calculated by starting the calculations and setting the first dose to each user's specified weekday and weekend wake times, weekday and weekend wake times plus an additional time interval, or weekday and weekend breakfast times, setting subsequent dose times every 'n' hours after each start time, and stopping the calculation at each user's specified weekday and weekend bed times or continuing the calculation throughout subsequent 24 hour periods, "medications to be taken with a dose of another medication" dosing regimens calculated by linking the dependent medication's dosing indications to those calculated for the primary medication in each user account, "every other day" medication dosing regimens calculated by setting the dose times to each user's specified weekday and weekend wake times, weekday and weekend wake times plus an additional time interval, or weekday and weekend breakfast times, and alternating the daily dosing events, "once a week, once every two weeks, or once a month" medication dosing regimens calculated by enabling each user to select their preferred time and day the dose is to be taken and setting subsequent dose times on a weekly, bi-weekly, or monthly basis, and any other medication dosing regimen formula calculated using one or more schedule variables selected from the schedule data in each child's, spouse's, or legal dependent's user account, optional lead time variables for those schedule events, one or more dosage variables selected from the user-specific prescription medication data in each child's, spouse's, or legal dependent's user account, and optional user-specific variables from each child's, spouse's, or legal dependent's user account including their age, weight, or gender.

25. The system of claim 1 wherein (i) the user account set up algorithm requires that each user enter or specify schedule data including their weekday and weekend wake times, weekday and weekend bed times, weekday and weekend breakfast times, weekday and weekend lunch times, and weekday and weekend dinner times into their user account to complete the algorithm, (ii) the user account set up algorithm requires that each user enter, scan in, or specify one or more personal identifiers, primary health care account identifiers, or combinations thereof selected from the group consisting of their name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, prescription medication barcodes, and universal product codes into their user account to complete the algorithm, (iii) the user interface and secondary database system enable each user to select which prescription medications and related user-specific prescription medication data to upload from among the prescription medications identified from each particular primary health care database source in each user account, (iv) user-specific prescription medication data uploaded into each user account from at least one primary health care database/primary health care computer server or entered, scanned in, modified, or otherwise specified by each user in each user account includes one or more prescription medication identifiers selected from the group consisting of prescription medication brand names, prescription medication generic names, prescription medication scientific names, National Drug Codes, prescription numbers, prescription barcodes, and prescription medication barcodes for each medication, each medication's prescribed dosage, and each medication's prescribed number and type of units per dose including the unit dose, the volume of drug in solution, or the number of dosage forms, (v) user-specific prescription medication data uploaded into each user account from at least one primary health care database/primary health care computer server or entered, scanned in, modified, or otherwise specified by each user in each user account can include optional dosage data including routes of administration, sig codes, additional dosing indications, quantity of medication in number of units, quantity of medication in number of days of supply, prescription medication order dates, prescription medication refill dates, the dates prescription medications were dispensed, prescription medication images, Internet prescription medication links, Internet treatment links, and interaction warnings for each medication prescribed to each user, and (vi) the secondary database system calculates a user and time-specific medication dosing regimen for each prescription medication selected in each user account using one or more schedule variables selected from the schedule data in each user account, one or more dosage variables selected from the user-specific prescription medication data in each user account including at least the prescribed dosage and prescribed number and type of units per dose for each prescription medication, and a medication dosing regimen formula selected from the group consisting of "once in the morning" or "once a day" medication dosing regimens calculated by setting the dose times to each user's specified weekday and weekend wake times, weekday and weekend wake times plus an additional time interval, or weekday and weekend breakfast times, "once before bed" or "once at night" medication dosing regimens calculated by setting the dose times to each user's specified weekday and weekend bed times, weekday and weekend bed times minus an additional time interval, or weekday and weekend dinner times, "dosing with meals" medication dosing regimens calculated by setting the dose times to each user's specified weekday and weekend breakfast, lunch, and dinner times or weekday and weekend breakfast, lunch, and dinner times plus or minus an additional time interval, "dosing before meals" medication dosing regimens calculated by setting the dose times to each user's specified weekday and weekend breakfast, lunch, and dinner times minus an additional time interval, "dosing after meals" medication dosing regimens calculated by setting the dose times to each user's specified weekday and weekend breakfast, lunch, and dinner times plus an additional time interval, "dosing 'n' times per day" medication dosing regimens calculated by setting the first dose to each user's specified weekday and weekend wake times, weekday and weekend wake times plus an additional time interval, or weekday and weekend breakfast times, setting the final dose to each user's specified weekday and weekend bed times, weekday and weekend bed times minus an additional time interval, or weekday and weekend dinner times, and calculating additional dose times by dividing the number of remaining hours in each user's weekday and weekend day by 'n−1' and setting additional dose times at each time interval other than the first or final dose times, "dosing every 'n' hours" medication dosing regimens calculated by starting the calculations and setting the first dose to each user's specified weekday and weekend wake times, weekday and weekend wake times plus an additional time interval, or weekday and weekend breakfast times, setting subsequent dose times every 'n' hours after each start time, and stopping the calculations at each user's specified weekday and weekend bed times or continuing the calculation throughout subsequent 24 hour periods, "medications prescribed to be taken with a dose of another medication" dosing regimens calculated by linking the dependent medication's dosing indications to those calculated for the primary medication in each user account, "every other day" medication dosings regimens calculated by setting the dose times to each user's specified weekday and weekend wake times, weekday and weekend wake times plus an additional time interval, or weekday and weekend breakfast times and alternating the daily dosing events, "once a week, once every two weeks, or once a month" medication dosing regimens calculated by enabling each user to select their preferred time and day the dose is to be taken and setting subsequent dose times on a weekly, bi-weekly, or monthly basis, and any other medication dosing regimen formula calculated using one or more schedule variables selected from the schedule data in each user account, optional lead time variables for those schedule events, one or more dosage variables selected from the user-specific prescription medication data in each user account, and optional user-specific variables from each user account including each user's age, weight, or gender.

26. The system of claim 1 wherein (i) the user interface and secondary database system enable individuals including parents and legal guardians to create user accounts and perform requisite user actions on behalf of their children, spouses, legal dependents, or combinations thereof, also defined as system users, (ii) the user account set up algorithm requires that each user enter or specify schedule data including weekday and weekend wake times, weekday and weekend bed times, weekday and weekend breakfast times, weekday and weekend lunch times, and weekday and weekend dinner times into each child's, spouse's, or legal dependent's user account to complete the algorithm, (iii) the user account set up algorithm requires that each user enter, scan in, or otherwise specify one or more personal identifiers, primary health care account identifiers, or combinations thereof selected from the group consisting of each child's, spouse's, or legal dependent's name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, prescription medication barcodes, and universal product codes into each child's, spouse's, or legal dependent's user account to complete the algorithm, (iv) the user interface and secondary database system enable each user to select which prescription medications and related user-specific prescription medication data to upload from among the prescription medications identified from each particular primary health care database source in each child's, spouse's, or legal dependent's user account, (v) user-specific prescription medication data uploaded into each child's, spouse's, or legal dependent's user account from at least one primary health care database/primary health care computer server or entered, scanned in, modified, or otherwise specified by each user in each child's, spouse's, or legal dependent's user account includes one or more prescription medication identifiers selected from the group consisting of prescription medication brand names, prescription medication generic names, prescription medication scientific names, National Drug Codes, prescription numbers, prescription barcodes, and prescription medication barcodes for each medication, each medication's prescribed dosage, and each medication's prescribed number and type of units per dose including the unit dose, the volume of drug in solution, or the number of dosage forms, (vi) user-specific prescription medication data uploaded into each child's, spouse's, or legal dependent's user account from at least one primary health care database/primary health care computer server or entered, scanned in, modified, or otherwise specified by each user in each child's, spouse's, or legal dependent's user account can include optional dosage data including routes of administration, sig codes, additional dosing indications, quantity of medication in number of units, quantity of medication in number of days of supply, prescription medication order dates, prescription medication refill dates, the dates prescription medications were dispensed, prescription medication images, Internet prescription medication links, Internet treatment links, and interaction warnings for each medication prescribed to each child, spouse, or legal dependent, and (vii) the secondary database system calculates a user and time-specific medication dosing regimen for each prescription medication selected in each child's, spouse's, or legal dependent's user account using one or more schedule variables selected from the schedule data in each child's, spouse's, or legal dependent's user account, one or more dosage variables selected from the user-specific prescription medication data in each child's, spouse's, or legal dependent's user account including at least the prescribed dosage and prescribed number and type of units per dose for each prescription medication, and a medication dosing regimen formula selected from the group consisting of "once in the morning" or "once a day" medication dosing regimens calculated by setting the dose times to each user's specified weekday and weekend wake times, weekday and weekend wake times plus an additional time interval, or weekday and weekend breakfast times, "once before bed" or "once at night" medication dosing regimens calculated by setting the dose times to each user's specified weekday and weekend bed times, weekday and weekend bed times minus an additional time interval, or weekday and weekend dinner times, "dosing with meals" medication dosing regimens calculated by setting the dose times to each user's specified weekday and weekend breakfast, lunch, and dinner times or weekday and weekend breakfast, lunch, and dinner times plus or minus an additional time interval, "dosing before meals" medication dosing regimens calculated by setting the dose times to each user's specified weekday and weekend breakfast, lunch, and dinner times minus an additional time interval, "dosing after meals" medication dosing regimens calculated by setting the dose times to each user's specified weekday and weekend breakfast, lunch, and dinner times plus an additional time interval, "dosing 'n' times per day" medication dosing regimens calculated by setting the first dose to each user's specified weekday and weekend wake times, weekday and weekend wake times plus an additional time interval, or weekday and weekend breakfast times, setting the final dose to each user's specified weekday and weekend bed times, weekday and weekend bed times minus an additional time interval, or weekday and weekend dinner times, and calculating additional dose times by dividing the number of remaining hours in each user's weekday and weekend day by 'n–1' and setting additional dose times at each time interval other than the first or final dose times, "dosing every 'n' hours" medication dosing regimens calculated by starting the calculations and setting the first dose to each user's specified weekday and weekend wake times, weekday and weekend wake times plus an additional time interval, or weekday and weekend breakfast times, setting subsequent dose times every 'n' hours after each start time, and stopping the calculation at each user's specified weekday and weekend bed times or continuing the calculation throughout subsequent 24 hour periods, "medications to be taken with a dose of another medication" dosing regimens calculated by linking the dependent medication's dosing indications to those calculated for the primary medication in each user account, "every other day" medication dosing regimens calculated by setting the dose times to each user's specified weekday and weekend wake times, weekday and weekend wake times plus an additional time interval, or weekday and weekend breakfast times, and alternating the daily dosing events, "once a week, once every two weeks, or once a month" medication dosing regimens calculated by enabling each user to select their preferred time and day the dose is to be taken and setting subsequent dose times on a weekly, bi-weekly, or monthly basis, and any other medication dosing regimen formula calculated using one or more schedule variables selected from the schedule data in each child's, spouse's, or legal dependent's user account, optional lead time variables for those schedule events, one or more dosage variables selected from the user-specific prescription medication data in each child's, spouse's, or legal dependent's user account, and optional user-specific variables from each child's, spouse's, or legal dependent's user account including their age, weight, or gender.

27. The system of claim 1 wherein (i) the user account set up algorithm requires that each user enter or specify schedule data including their weekday and weekend wake times, weekday and weekend bed times, weekday and weekend breakfast times, weekday and weekend lunch times, and weekday and weekend dinner times into their user account to complete the algorithm, (ii) the user account set up algorithm requires that each user enter, scan in, or otherwise specify one or more personal identifiers, primary health care account identifiers, prescription medication identifiers, or combinations thereof selected from the group consisting of each user's name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, prescription medication barcodes, and universal product codes into their user account to complete the algorithm, (iii) the secondary database system utilizes said personal identifiers, primary health care account identifiers, prescription medication identifiers, or combinations thereof to authenticate each user and prescription medication against at least one primary health care database or primary health care computer server and authorize and upload user-specific prescription medication data for each identified prescription medication from each primary health care database or primary health care computer server into the secondary database system and each user account, (iv) user-specific prescription medication data uploaded into each user account from at least one primary health care database/primary health care computer server or entered, scanned in, modified, or otherwise specified by each user in each user account includes one or more prescription medication identifiers selected from the group consisting of prescription medication brand names, prescription medication generic names, prescription medication scientific names, National Drug Codes, prescription numbers, prescription barcodes, and prescription medication barcodes for each medication, each medication's prescribed dosage, and each medication's prescribed number and type of units per dose including the unit dose, the volume of drug in solution, or the number of dosage forms, (v) user-specific prescription medication data uploaded into each user account from at least one primary health care database/primary health care computer server or entered, scanned in, modified, or otherwise specified by each user in each user account can include optional dosage data including routes of administration, sig codes, additional dosing indications, quantity of medication in number of units, quantity of medication in number of days of supply, prescription medication order dates, prescription medication refill dates, the dates prescription medications were dispensed, prescription medication images, Internet prescription medication links, Internet treatment links, and interaction warnings for each medication prescribed to each user, and (vi) the secondary database system calculates a user and time-specific medication dosing regimen for each prescription medication in each user account using one or more schedule variables selected from the schedule data in each user account, one or more dosage variables selected from the user-specific prescription medication data in each user account including at least the prescribed dosage and prescribed number and type of units per dose for each prescription medication, and a medication dosing regimen formula selected from the group consisting of "once in the morning" or "once a day" medication dosing regimens calculated by setting the dose times to each user's specified weekday and weekend wake times, weekday and weekend wake times plus an additional time interval, or weekday and weekend breakfast times, "once before bed" or "once at night" medication dosing regimens calculated by setting the dose times to each user's specified weekday and weekend bed times, weekday and weekend bed times minus an additional time interval, or weekday and weekend dinner times, "dosing with meals" medication dosing regimens calculated by setting the dose times to each user's specified weekday and weekend breakfast, lunch, and dinner times or weekday and weekend breakfast, lunch, and dinner times plus or minus an additional time interval, "dosing before meals" medication dosing regimens calculated by setting the dose times to each user's specified weekday and weekend breakfast, lunch, and dinner times minus an additional time interval, "dosing after meals" medication dosing regimens calculated by setting the dose times to each user's specified weekday and weekend breakfast, lunch, and dinner times plus an additional time interval, "dosing 'n' times per day" medication dosing regimens calculated by setting the first dose to each user's specified weekday and weekend wake times, weekday and weekend wake times plus an additional time interval, or weekday and weekend breakfast times, setting the final dose to each user's specified weekday and weekend bed times, weekday and weekend bed times minus an additional time interval, or weekday and weekend dinner times, and calculating additional dose times by dividing the number of remaining hours in each user's weekday and weekend day by 'n–1' and setting additional dose times at each time interval other than the first or final dose times, "dosing every 'n' hours" medication dosing regimens calculated by starting the calculations and setting the first dose to each user's specified weekday and weekend wake times, weekday and weekend wake times plus an additional time interval, or weekday and weekend breakfast times, setting subsequent dose times every 'n' hours after each start time, and stopping the calculations at each user's specified weekday and weekend bed times or continuing the calculation throughout subsequent 24 hour periods, "medications prescribed to be taken with a dose of another medication" dosing regimens calculated by linking the dependent medication's dosing indications to those calculated for the primary medication in each user account, "every other day" medication dosings regimens calculated by setting the dose times to each user's specified weekday and weekend wake times, weekday and weekend wake times plus an additional time interval, or weekday and weekend breakfast times and alternating the daily dosing events, "once a week, once every two weeks, or once a month" medication dosing regimens calculated by enabling each user to select their preferred time and day the dose is to be taken and setting subsequent dose times on a weekly, bi-weekly, or monthly basis, and any other medication dosing regimen formula calculated using one or more schedule variables selected from the schedule data in each user account, optional lead time variables for those schedule events, one or more dosage variables selected from the user-specific prescription medication data in each user account, and optional user-specific variables from each user account including each user's age, weight, or gender.

28. The system of claim 1 wherein (i) the user interface and secondary database system enable individuals including parents and legal guardians to create user accounts and perform requisite user actions on behalf of their children, spouses, legal dependents, or combinations thereof, also defined as system users, (ii) the user account set up algorithm requires that each user enter or specify schedule data including weekday and weekend wake times, weekday and weekend bed times, weekday and weekend breakfast times, weekday and weekend lunch times, and weekday and weekend dinner times in each child's, spouse's, or legal dependent's user account to complete the algorithm, (iii) the user account set up algorithm requires that each user enter, scan in, or otherwise specify one or more personal identifiers, primary health care account identifiers, prescription medication identifiers, or combinations thereof selected from the group consisting of each child's, spouse's, or legal dependent's name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, prescription medication barcodes, and universal product codes into each child's, spouse's, or legal dependent's user account to complete the algorithm, (iv) the secondary database system utilizes said personal identifiers, primary health care account identifiers, prescription medication identifiers, or combinations thereof from each child's, spouse's, or legal dependent's user account to authenticate each prescription medication and child, spouse, or legal dependent against at least one primary health care database or primary health care computer server and authorize and upload user-specific prescription medication data for each identified prescription medication from each primary health care database or primary health care computer server into the secondary database system and each child's, spouse's, or legal dependent's user account, (v) user-specific prescription medication data uploaded into each child's, spouse's, or legal dependent's user account from at least one primary health care database/primary health care computer server or entered, scanned in, modified, or otherwise specified by each user in each child's, spouse's, or legal dependent's user account includes one or more prescription medication identifiers selected from the group consisting of prescription medication brand names, prescription medication generic names, prescription medication scientific names, National Drug Codes, prescription numbers, prescription barcodes, and prescription medication barcodes for each medication, each medication's prescribed dosage, and each medication's prescribed number and type of units per dose including the unit dose, the volume of drug in solution, or the number of dosage forms, (vi) user-specific prescription medication data uploaded into each child's, spouse's, or legal dependent's user account from at least one primary health care database/primary health care computer server or entered, scanned in, modified, or otherwise specified by each user in each child's, spouse's, or legal dependent's user account can include optional dosage data including routes of administration, sig codes, additional dosing indications, quantity of medication in number of units, quantity of medication in number of days of supply, prescription medication order dates, prescription medication refill dates, the dates prescription medications were dispensed, prescription medication images, Internet prescription medication links, Internet treatment links, and interaction warnings for each medication prescribed to each child, spouse, or legal dependent, and (vii) the secondary database system calculates a user and time-specific medication dosing regimen for each prescription medication in each child's, spouse's, or legal dependent's user account using one or more schedule variables selected from the schedule data in each child's, spouse's, or legal dependent's user account, one or more dosage variables selected from the user-specific prescription medication data in each child's, spouse's, or legal dependent's user account including at least the prescribed dosage and prescribed number and type of units per dose for each prescription medication, and a medication dosing regimen formula selected from the group consisting of "once in the morning" or "once a day" medication dosing regimens calculated by setting the dose times to each user's specified weekday and weekend wake times, weekday and weekend wake times plus an additional time interval, or weekday and weekend breakfast times, "once before bed" or "once at night" medication dosing regimens calculated by setting the dose times to each user's specified weekday and weekend bed times, weekday and weekend bed times minus an additional time interval, or weekday and weekend dinner times, "dosing with meals" medication dosing regimens calculated by setting the dose times to each user's specified weekday and weekend breakfast, lunch, and dinner times or weekday and weekend breakfast, lunch, and dinner times plus or minus an additional time interval, "dosing before meals" medication dosing regimens calculated by setting the dose times to each user's specified weekday and weekend breakfast, lunch, and dinner times minus an additional time interval, "dosing after meals" medication dosing regimens calculated by setting the dose times to each user's specified weekday and weekend breakfast, lunch, and dinner times plus an additional time interval, "dosing 'n' times per day" medication dosing regimens calculated by setting the first dose to each user's specified weekday and weekend wake times, weekday and weekend wake times plus an additional time interval, or weekday and weekend breakfast times, setting the final dose to each user's specified weekday and weekend bed times, weekday and weekend bed times minus an additional time interval, or weekday and weekend dinner times, and calculating additional dose times by dividing the number of remaining hours in each user's weekday and weekend day by 'n−1' and setting additional dose times at each time interval other than the first or final dose times, "dosing every 'n' hours" medication dosing regimens calculated by starting the calculations and setting the first dose to each user's specified weekday and weekend wake times, weekday and weekend wake times plus an additional time interval, or weekday and weekend breakfast times, setting subsequent dose times every 'n' hours after each start time, and stopping the calculation at each user's specified weekday and weekend bed times or continuing the calculation throughout subsequent 24 hour periods, "medications to be taken with a dose of another medication" dosing regimens calculated by linking the dependent medication's dosing indications to those calculated for the primary medication in each user account, "every other day" medication dosing regimens calculated by setting the dose times to each user's specified weekday and weekend wake times, weekday and weekend wake times plus an additional time interval, or weekday and weekend breakfast times, and alternating the daily dosing events, "once a week, once every two weeks, or once a month" medication dosing regimens calculated by enabling each user to select their preferred time and day the dose is to be taken and setting subsequent dose times on a weekly, bi-weekly, or monthly basis, and any other medication dosing regimen formula calculated using one or more schedule variables selected from the schedule data in each child's, spouse's, or legal dependent's user account, optional lead time variables for those schedule events, one or more dosage variables selected from the user-specific prescription medication data in each child's, spouse's, or legal dependent's user account, and optional user-specific variables from each child's, spouse's, or legal dependent's user account including their age, weight, or gender.

29. The system of claim 1 wherein (i) the user account set up algorithm requires that each user enter or specify schedule data including their weekday and weekend wake times, weekday and weekend bed times, weekday and weekend breakfast times, weekday and weekend lunch times, and weekday and weekend dinner times into their user account to complete the algorithm, (ii) the user account set up algorithm requires that each user enter, scan in, or otherwise specify one or more personal identifiers, primary health care account identifiers, or combinations thereof selected from the group consisting of their name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, prescription medication barcodes, and universal product codes into their user account to complete the algorithm, (iii) user-specific prescription medication data uploaded into each user account from at least one primary health care database/primary health care computer server or entered, scanned in, modified, or otherwise specified by each user in each user account includes one or more prescription medication identifiers selected from the group consisting of prescription medication brand names, prescription medication generic names, prescription medication scientific names, National Drug Codes, prescription numbers, prescription barcodes, and prescription medication barcodes for each medication, each medication's prescribed dosage, and each medication's prescribed number and type of units per dose including the unit dose, the volume of drug in solution, or the number of dosage forms, (iv) user-specific prescription medication data uploaded into each user account from at least one primary health care database/primary health care computer server or entered, scanned in, modified, or otherwise specified by each user in each user account can include optional dosage data including routes of administration, sig codes, additional dosing indications, quantity of medication in number of units, quantity of medication in number of days of supply, prescription medication order dates, prescription medication refill dates, the dates prescription medications were dispensed, prescription medication images, Internet prescription medication links, Internet treatment links, and interaction warnings for each medication prescribed to each user, (v) the secondary database system uploads non user-specific prescription medication data which can include prescription medication brand names, prescription medication generic names, prescription medication scientific names, and each medication's indicated unit doses, dosage forms, volume of drug in solution, dosages, routes of administration, sig codes, quantity of medication in number of units, quantity of medication in number of days of supply, National Drug Codes, medication barcodes, universal product codes, medication images, Internet medication links, Internet treatment links, prescription drug prices, prescription drug wholesale prices, generic drug prices, price comparisons, generic drug substitutes, and interaction warnings into a secondary database system database from at least one primary health care database or primary health care computer server, (vi) the secondary database system uploads alternative medication data which can include over-the-counter medications, vitamins, supplements, and herbal medications and their corresponding names, barcodes, universal product codes, unit doses, dosage forms, dosages, routes of administration, sig codes, quantity of alternative medication in number of units, quantity of medication in number of days of supply, alternative medication images, Internet alternative medication links, and Internet treatment links into a secondary database system database from at least one primary health care database or primary health care computer server, (vii) the user interface and secondary database system enable each user to select, add, and modify non user-specific prescription medication data, over-the-counter medication data, vitamin data, supplement data, herbal medication data, or combinations thereof from said secondary database system database into their user account including one or more prescription medications, over-the-counter medications, vitamins, supplements, or herbal medications and their corresponding names, dosages, number and type of units per dose, and optional additional dosage data, (viii) the user interface and secondary database system enable each user to select prescription medications, over-the-counter medications, vitamins, supplements, and herbal medications in their user account for further system use, (ix) the secondary database system calculates a user and time-specific medication dosing regimen for each user-specific prescription medication, non user-specific prescription medication, over-the-counter medication, vitamin, supplement, or herbal medication selected in each user account using one or more schedule variables selected from the schedule data in each user account, one or more dosage variables selected from the user-specific prescription medication data in each user account for each user-specific prescription medication or the dosage data entered, selected, or otherwise specified by each user in each user account for each non user-specific prescription medication, over-the-counter medication, vitamin, supplement, or herbal medication, and a medication dosing regimen formula selected from the group consisting of "once in the morning" or "once a day" medication dosing regimens calculated by setting the dose times to each user's specified weekday and weekend wake times, weekday and weekend wake times plus an additional time interval, or weekday and weekend breakfast times, "once before bed" or "once at night" medication dosing regimens calculated by setting the dose times to each user's specified weekday and weekend bed times, weekday and weekend bed times minus an additional time interval, or weekday and weekend dinner times, "dosing with meals" medication dosing regimens calculated by setting the dose times to each user's specified weekday and weekend breakfast, lunch, and dinner times or weekday and weekend breakfast, lunch, and dinner times plus or minus an additional time interval, "dosing before meals" medication dosing regimens calculated by setting the dose times to each user's specified weekday and weekend breakfast, lunch, and dinner times minus an additional time interval, "dosing after meals" medication dosing regimens calculated by setting the dose times to each user's specified weekday and weekend breakfast, lunch, and dinner times plus an additional time interval, "dosing 'n' times per day" medication dosing regimens calculated by setting the first dose to each user's specified weekday and weekend wake times, weekday and weekend wake times plus an additional time interval, or weekday and weekend breakfast times, setting the final dose to each user's specified weekday and weekend bed times, weekday and weekend bed times minus an additional time interval, or weekday and weekend dinner times, and calculating additional dose times by dividing the number of remaining hours in each user's weekday and weekend day by 'n−1' and setting additional dose times at each time interval other than the first or final dose times, "dosing every 'n' hours" medication dosing regimens calculated by starting the calculations and setting the first dose time to each user's specified weekday and weekend wake times, weekday and weekend wake times plus an additional time interval, or weekday and weekend breakfast times, setting subsequent dose times every 'n' hours after each start time, and stopping the calculation at each user's specified weekday and weekend bed times or continuing the calculation throughout subsequent 24 hour periods, "medications prescribed to be taken with a dose of another medication" dosing regimens calculated by linking the dependent medication's dosing indications to those calculated for the primary medication in that user account, "every other day" medication dosing regimens calculated by setting the dose times to each user's specified weekday and weekend wake times, weekday and weekend wake times plus an additional time interval, or weekday and weekend breakfast times, and alternating the daily dosing events, "once a week, once every two weeks, or once a month" medication dosing regimens calculated by enabling each user to select their preferred time and day the dose is to be taken and setting subsequent dose times on a weekly, bi-weekly, or monthly basis, and any other medication dosing regimen formula calculated using one or more schedule variables selected from the schedule data in each user's account, optional lead time variables for those schedule events, one or more dosage variables selected from the user-specific prescription medication data in each user account for each user-specific medication or the dosage data specified in each user account for each non user-specific prescription medication, over-the-counter medication, vitamin, supplement, or herbal medication, and optional user-specific variables from each user account including each user's age, weight, and gender, (viii) the secondary database system generates user and time-specific medication dosing instructions for each dose of user-specific prescription medication, non user-specific prescription medication, over-the-counter medication, vitamin, supplement, or herbal medication selected in each user account including at least the user's name, prescription or alternative medication name, dose time, and number and type of units to be taken at that dose time based on the medication dosing regimen calculated for that user, day, and prescription or alternative medication, (ix) the user interface and secondary database system enable each user to optionally enhance their user and time-specific medication dosing instructions with a prescription or alternative medication image, Internet prescription or alternative medication link, or Internet treatment link based on user account selections, and (x) the wireless messaging platform utilizes said user and time-specific medication dosing instructions in conjunction with data in each user account including each user's current time zone and wireless phone number or wireless device identifier to determine wireless message recipients and format, schedule, and transmit data-based messages containing user and time-specific medication dosing instructions over one or more networks to wireless carriers or wireless messaging gateways for wireless delivery to each user at system-determined medication dose times on their wireless phones, Smartphones, PDAs, wireless devices, or combinations thereof via SMS, EMS, MMS, WAP-Push, BREW, SIP, IM, email, or any combination thereof.

30. The system of claim 1 wherein (i) the user interface and secondary database system enable individuals including parents and legal guardians to create user accounts and perform requisite user actions on behalf of their children, spouses, legal dependents, or combinations thereof, also defined as system users, (ii) the user account set up algorithm requires that each user enter or specify schedule data including weekday and weekend wake times, weekday and weekend bed times, weekday and weekend breakfast times, weekday and weekend lunch times, and weekday and weekend dinner times into their child's, spouse's, or legal dependent's user account to complete the algorithm, (iii) the user account set up algorithm requires that each user enter, scan in, or otherwise specify one or more personal identifiers, primary health care account identifiers, or combinations thereof selected from the group consisting of each child's, spouse's, or legal dependent's name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, prescription medication barcodes, and universal product codes into their child's, spouse's, or legal dependent's user account to complete the algorithm, (iv) user-specific prescription medication data uploaded into each child's, spouse's, or legal dependent's user account from at least one primary health care database/primary health care computer server or entered, scanned in, modified, or otherwise specified by each user in each child's, spouse's, or legal dependent's user account includes one or more prescription medication identifiers selected from the group consisting of prescription medication brand names, prescription medication generic names, prescription medication scientific names, National Drug Codes, prescription numbers, prescription barcodes, and prescription medication barcodes for each medication, each medication's prescribed dosage, and each medication's prescribed number and type of units per dose including the unit dose, the volume of drug in solution, or the number of dosage forms, (v) user-specific prescription medication data uploaded into each child's, spouse's, or legal dependent's user account from at least one primary health care database/primary health care computer server or entered, scanned in, modified, or otherwise specified by each user in each child's, spouse's, or legal dependent's user account can include optional dosage data including routes of administration, sig codes, additional dosing indications, quantity of medication in number of units, quantity of medication in number of days of supply, prescription medication order dates, prescription medication refill dates, the dates prescription medications were dispensed, prescription medication images, Internet prescription medication links, Internet treatment links, and interaction warnings for each medication prescribed to each child, spouse, or legal dependent, (vi) the secondary database system uploads non user-specific prescription medication data which can include prescription medication brand names, prescription medication generic names, prescription medication scientific names, and their indicated dosages, number and type of units per dose, unit doses, dosage forms, volume of drug in solution, routes of administration, sig codes, additional dosing indications, quantity of medication in number of units, quantity of medication in number of days of supply, National Drug Codes, medication barcodes, universal product codes, prescription medication images, Internet prescription medication links, Internet treatment links, prescription drug prices, prescription drug wholesale prices, generic drug prices, price comparisons, generic drug substitutes, and interaction warnings into a secondary database system database from at least one primary health care database or primary health care computer server, (vii) the secondary database system uploads alternative medication data which can include over-the-counter medications, vitamins, supplements, and herbal medications and their corresponding names, barcodes, universal product codes, unit doses, dosage forms, volume of drug in solution, dosages, routes of administration, quantity of alternative medication in number of units, quantity of alternative medication in number of days of supply, alternative medication images, Internet alternative medication links, and Internet treatment links into a secondary database system database from at least one primary health care database or primary health care computer server, (viii) the user interface and secondary database system enable each user to select, add, and modify non user-specific prescription medication data, over-the-counter medication data, vitamin data, supplement data, herbal medication data, or combinations thereof from the secondary database system database into their child's, spouse's, or legal dependent's user account including one or more prescription medications, over-the-counter medications, vitamins, supplements, or herbal medications and their corresponding names, dosages, number and type of units per dose including unit dose, volume of drug solution, or number of dosage forms, and optional additional dosage data, (ix) the user interface and secondary database system enable each user to select prescription medications, over-the-counter medications, vitamins, supplements, or herbal medications in their child's, spouse's, or legal dependent's user account for further system use, (x) the secondary database system calculates a user-specific medication dosing regimen for each user-specific prescription medication, non user-specific prescription medication, over-the-counter medication, vitamin, supplement, or herbal medication selected in each child's, spouse's, or legal dependent's user account using one or more schedule variables selected from the schedule data in each child's, spouse's, or legal dependent's user account, one or more dosage variables selected from the user-specific prescription medication data for each user-specific prescription medication in each child's, spouse's, or legal dependent's user account or the dosage data selected, added, or otherwise specified by each user for each non user-specific prescription medication, over-the-counter medication, vitamin, supplement, or herbal medication in each child's, spouse's, or legal dependent's user account, and a medication dosing regimen formula selected from the group consisting of "once in the morning" or "once a day" medication dosing regimens calculated by setting the dose times to each user's specified weekday and weekend wake times, weekday and weekend wake times plus an additional time interval, or weekday and weekend breakfast times, "once before bed" or "once at night" medication dosing regimens calculated by setting the dose times to each user's specified weekday and weekend bed times, weekday and weekend bed times minus an additional time interval, or weekday and weekend dinner times, "dosing with meals" medication dosing regimens calculated by setting the dose times to each user's specified weekday and weekend breakfast, lunch, and dinner times or weekday and weekend breakfast, lunch, and dinner times plus or minus an additional time interval, "dosing before meals" medication dosing regimens calculated by setting the dose times to each user's specified weekday and weekend breakfast, lunch, and dinner times minus an additional time interval, "dosing after meals" medication dosing regimens calculated by setting the dose times to each user's specified weekday and weekend breakfast, lunch, and dinner times plus an additional time interval, "dosing 'n' times per day" medication dosing regimens calculated by setting the first dose to each user's specified weekday and weekend wake times, weekday and weekend wake times plus an additional time interval, or weekday and weekend breakfast times, setting the final dose to each user's specified weekday and weekend bed times, weekday and weekend bed times minus an additional time interval, or weekday and weekend dinner times, and calculating additional dose times by dividing the number of remaining hours in each user's weekday and weekend day by 'n–1' and setting additional dose times at each time interval other than the first or final dose times, "dosing every 'n' hours" medication dosing regimens calculated by starting the calculations at each user's specified weekday and weekend wake times, weekday and weekend wake times plus an additional time interval, or weekday and weekend breakfast times, setting subsequent dose times every 'n' hours after each start time, and stopping the calculations at each user's specified weekday and weekend bed times or continuing the calculation throughout subsequent 24 hour periods, "medications prescribed to be taken with a dose of another medication" dosing regimens calculated by linking the dependent medication's dosing indications to those calculated for the primary medication in that user account, "every other day" medication dosing regimens calculated by setting the dose times to each user's specified weekday and weekend wake times, weekday and weekend wake times plus an additional time interval, or weekday and weekend breakfast times, and alternating the daily dosing events, "once a week, once every two weeks, or once a month" medication dosing regimen calculations by enabling each user to select their preferred time and day the dose is to be taken and setting subsequent dose times on a weekly, bi-weekly, or monthly basis, and any other medication dosing regimen formula calculated using one or more schedule variables selected from the schedule data in each child's, spouse's, or legal dependent's user account, optional lead time variables for those schedule events, one or more dosage variables selected from the user-specific prescription medication data in each child's, spouse's, or legal dependent's user account for each user-specific prescription medication or the dosage data specified in each child's, spouse's, or legal dependent's user account for each non user-specific prescription medication, over-the-counter medication, vitamin, supplement, or herbal medication, and optional user-specific variables from each child's, spouse's, or legal dependent's user account including their age, weight, and gender, (xi) the secondary database system generates user and time-specific medication dosing instructions for each dose of prescription medication, over-the-counter medication, vitamin, supplement, or herbal medication selected in each child's, spouse's, or legal dependent's user account including at least the user's name, dose time, prescription or alternative medication name, and number and type of units to be taken at that dose time based on the system-calculated dosing regimen for that user, day, and prescription or alternative medication, (xii) the user interface and secondary database system enable each user to optionally enhance their child's, spouse's, or legal dependent's user-specific medication dosing instructions with a prescription or alternative medication image, Internet prescription or alternative medication link, or Internet treatment link based on user selections in each child's, spouse's, or legal dependent's user account, and (xiii) the wireless messaging platform utilizes said user-specific medication dosing instructions in conjunction with data in each child's, spouse's, or legal dependent's user account including the specified current time zone and wireless phone number or wireless device identifier to determine wireless message recipients and format, schedule, and transmit data-based messages containing said user-specific medication dosing instructions over one or more networks to wireless carriers or wireless messaging gateways for wireless delivery to users including individuals, parents, legal guardians, children, spouses, legal dependents, or combinations thereof at system-determined medication dose times on their wireless phones, Smartphones, PDAs, wireless devices, or combinations thereof via SMS, EMS, MMS, WAP-Push, BREW, SIP, IM, email, or any combination thereof.

31. The system of claim 1 wherein (i) the user account set up algorithm requires that each user enter or specify schedule data including their weekday and weekend wake times, weekday and weekend bed times, weekday and weekend breakfast times, weekday and weekend lunch times, and weekday and weekend dinner times into their user account to complete the algorithm, (ii) the user account set up algorithm requires that each user enter, scan in, or otherwise specify one or more personal identifiers, primary health care account identifiers, or combinations thereof selected from the group consisting of their name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, and prescription medication barcodes into their user account to complete the algorithm, (iii) user-specific prescription medication data uploaded into each user account from at least one primary health care database/primary health care computer server or entered, scanned in, modified, or otherwise specified by each user in each user account includes one or more prescription medication identifiers selected from the group consisting of prescription medication brand names, prescription medication generic names, prescription medication scientific names, National Drug Codes, prescription numbers, prescription barcodes, and prescription medication barcodes for each medication, each medication's prescribed dosage, and each medication's prescribed number and type of units per dose including the unit dose, the volume of drug in solution, or the number of dosage forms, (iv) user-specific prescription medication data uploaded into each user account from at least one primary health care database/primary health care computer server or entered, scanned in, modified, or otherwise specified by each user in each user account can include optional dosage data including routes of administration, sig codes, additional dosing indications, quantity of medication in number of units, quantity of medication in number of days of supply, prescription medication order dates, prescription medication refill dates, the dates prescription medications were dispensed, prescription medication images, Internet prescription medication links, Internet treatment links, and interactions warnings for each medication prescribed to each user, (v) the user interface and secondary database system enable each user to select or add additional alternative medications and related dosage data into their user account including one or more over-the-counter medications, vitamins, supplements, herbal medications and their corresponding names, dosages, routes of administration, and number and type of units per dose, (vi) the user interface and secondary database system enable each user to select prescription medications, over-the-counter medications, vitamins, supplements, and herbal medications in each user account for further system use, (vii) the secondary database system calculates a user and time-specific medication dosing regimen for each prescription medication, over-the-counter medication, vitamin, supplement, or herbal medication selected in each user account using one or more schedule variables selected from the schedule data in each user account, one or more dosage variables selected from the user-specific prescription medication data in each user account for each prescription medication or the dosage data entered, selected, or otherwise specified by each user in each user account for each over-the-counter medication, vitamin, supplement, or herbal medication including at least the dosage and number and type of units per dose, and a medication dosing regimen formula selected from the group consisting of "once in the morning" or "once a day" medication dosing regimens calculated by setting the dose times to each user's specified weekday and weekend wake times, weekday and weekend wake times plus an additional time interval, or weekday and weekend breakfast times, "once before bed" or "once at night" medication dosing regimens calculated by setting the dose times to each user's specified weekday and weekend bed times, weekday and weekend bed times minus an additional time interval, or weekday and weekend dinner times, "dosing with meals" medication dosing regimens calculated by setting the dose times to each user's specified weekday and weekend breakfast, lunch, and dinner times or weekday and weekend breakfast, lunch, and dinner times plus or minus an additional time interval, "dosing before meals" medication dosing regimens calculated by setting the dose times to each user's specified weekday and weekend breakfast, lunch, and dinner times minus an additional time interval, "dosing after meals" medication dosing regimens calculated by setting the dose times to each user's specified weekday and weekend breakfast, lunch, and dinner times plus an additional time interval, "dosing 'n' times per day" medication dosing regimens calculated by setting the first dose to each user's specified weekday and weekend wake times, weekday and weekend wake times plus an additional time interval, or weekday and weekend breakfast times, setting the final dose to each user's specified weekday and weekend bed times, weekday and weekend bed times minus an additional time interval, or weekday and weekend dinner times, and calculating additional dose times by dividing the number of remaining hours in each user's weekday and weekend day by 'n−1' and setting additional dose times at each time interval other than the first or final dose times, "dosing every 'n' hours" medication dosing regimens calculated by starting the calculations and setting the first dose time to each user's specified weekday and weekend wake times, weekday and weekend wake times plus an additional time interval, or weekday and weekend breakfast times, setting subsequent dose times every 'n' hours after each start time, and stopping the calculation at each user's specified weekday and weekend bed times or continuing the calculation throughout subsequent 24 hour periods, "medications prescribed to be taken with a dose of another medication" dosing regimens calculated by linking the dependent medication's dosing indications to those calculated for the primary medication in that user account, "every other day" medication dosing regimens calculated by setting the dose times to each user's specified weekday and weekend wake times, weekday and weekend wake times plus an additional time interval, or weekday and weekend breakfast times, and alternating the daily dosing events, "once a week, once every two weeks, or once a month" medication dosing regimens calculated by enabling each user to select their preferred time and day the dose is to be taken and setting subsequent dose times on a weekly, bi-weekly, or monthly basis, and any other medication dosing regimen formula calculated using one or more schedule variables selected from the schedule data in each user account, optional lead time variables for those schedule events, one or more dosage variables selected from the user-specific prescription medication data in each user account for each prescription medication or the dosage data specified in each user account for each alternative medication, and optional user-specific variables from each user account including each user's age, weight, and gender, (vii) the secondary database system generates user and time-specific medication dosing instructions for each dose of selected prescription medication, over-the-counter medication, vitamin, supplement, or herbal medication including at least the dose time, user's name, prescription or alternative medication name, and number and type of units to be taken at that dose time, based on the medication dosing regimen calculated for that user, day, and prescription or alternative medication, (viii) the user interface and secondary database system enable users to optionally enhance their user and time-specific medication dosing instructions with a prescription or alternative medication image, Internet prescription or alternative medication link, Internet treatment link, advertisement, or logo based on user account selections, and (ix) the wireless messaging platform utilizes said user and time-specific medication dosing instructions in conjunction with data in user accounts including each user's current time zone and wireless phone number or wireless device identifier to determine wireless message recipients and format, schedule, and transmit data-based messages containing said user and time-specific medication dosing instructions over one or more networks to wireless carriers or wireless messaging gateways for wireless delivery to each user at system-determined medication dose times on their wireless phones, Smartphones, PDAs, wireless devices, or combinations thereof via SMS, EMS, MMS, WAP-Push, BREW, SIP, IM, email, or any combination thereof.

32. The system of claim 1 wherein (i) the user interface and secondary database system enable individuals including parents and legal guardians to create user accounts and perform requisite user actions on behalf of their children, spouses, legal dependents, or combinations thereof, also defined as system users, (ii) the user account set up algorithm requires that each user enter or specify schedule data including weekday and weekend wake times, weekday and weekend bed times, weekday and weekend breakfast times, weekday and weekend lunch times, and weekday and weekend dinner times in each child's, spouse's, or legal dependent's user account to complete the algorithm, (iii) the user account set up algorithm requires that each user enter, scan in, or otherwise specify one or more personal identifiers, primary health care account identifiers, or combinations thereof selected from the group consisting of each child's, spouse's, or legal dependent's name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, and prescription medication barcodes in each child's, spouse's, or legal dependent's user account to complete the algorithm, (iv) user-specific prescription medication data uploaded into each child's, spouse's, or legal dependent's user account from at least one primary health care database/primary health care computer server or entered, scanned in, modified, or otherwise specified by each user in each child's, spouse's, or legal dependent's user account includes one or more prescription medication identifiers selected from the group consisting of prescription medication brand names, prescription medication generic names, prescription medication scientific names, National Drug Codes, prescription numbers, prescription barcodes, and prescription medication barcodes for each medication, each medication's prescribed dosage, and each medication's prescribed number and type of units per dose including the unit dose, the volume of drug in solution, or the number of dosage forms, (v) user-specific prescription medication data uploaded into each child's, spouse's, or legal dependent's user account from at least one primary health care database/primary health care computer server or entered, scanned in, modified, or otherwise specified by each user in each child's, spouse's, or legal dependent's user account can include optional dosage data including routes of administration, sig codes, additional dosing indications, quantity of medication in number of units, quantity of medication in number of days of supply, prescription medication order dates, prescription medication refill dates, the dates prescription medications were dispensed, prescription medication images, Internet prescription medication links, Internet treatment links, and interaction warnings for each medication prescribed to each child, spouse, or legal dependent, (vi) the user interface and secondary database system enable each user to select or add additional alternative medications and dosage data into each child's, spouse's, or legal dependent's user account including one or more over-the-counter medications, vitamins, supplements, herbal medications and their corresponding names, dosages, routes of administration, and number and type of units per dose including unit doses, volume of drug in solution, and number of dosage forms, (vii) the user interface and secondary database system enable each user to select prescription medications, over-the-counter medications, vitamins, supplements, or herbal medications in each child's, spouse's, or legal dependent's user account for further system use, (viii) the secondary database system calculates a user-specific medication dosing regimen for each user-specific prescription medication, over-the-counter medication, vitamin, supplement, or herbal medication selected in each child's, spouse's, or legal dependent's user account using one or more schedule variables selected from the schedule data in each child's, spouse's, or legal dependent's user account, one or more dosage variables selected from the user-specific prescription medication data in each child's, spouse's, or legal dependent's user account for each prescription medication or the dosage data added or otherwise specified in each child's, spouse's, or legal dependent's user account for each over-the-counter medication, vitamin, supplement, or herbal medication including at least the dosage and number and type of units per dose, and a medication dosing regimen formula selected from the group consisting of "once in the morning" or "once a day" medication dosing regimens calculated by setting the dose times to each user's specified weekday and weekend wake times, weekday and weekend wake times plus an additional time interval, or weekday and weekend breakfast times, "once before bed" or "once at night" medication dosing regimens calculated by setting the dose times to each user's specified weekday and weekend bed times, weekday and weekend bed times minus an additional time interval, or weekday and weekend dinner times, "dosing with meals" medication dosing regimens calculated by setting the dose times to each user's specified weekday and weekend breakfast, lunch, and dinner times or weekday and weekend breakfast, lunch, and dinner times plus or minus an additional time interval, "dosing before meals" medication dosing regimens calculated by setting the dose times to each user's specified weekday and weekend breakfast, lunch, and dinner times minus an additional time interval, "dosing after meals" medication dosing regimens calculated by setting the dose times to each user's specified weekday and weekend breakfast, lunch, and dinner times plus an additional time interval, "dosing 'n' times per day" medication dosing regimens calculated by setting the first dose to each user's specified weekday and weekend wake times, weekday and weekend wake times plus an additional time interval, or weekday and weekend breakfast times, setting the final dose to each user's specified weekday and weekend bed times, weekday and weekend bed times minus an additional time interval, or weekday and weekend dinner times, and calculating additional dose times by dividing the number of remaining hours in each user's weekday and weekend day by 'n−1' and setting additional dose times at each time interval other than the first or final dose times, "dosing every 'n' hours" medication dosing regimens calculated by starting the calculations at each user's specified weekday and weekend wake times, weekday and weekend wake times plus an additional time interval, or weekday and weekend breakfast times, setting subsequent dose times every 'n' hours after each start time, and stopping the calculations at each user's specified weekday and weekend bed times or continuing the calculation throughout subsequent 24 hour periods, "medications prescribed to be taken with a dose of another medication" dosing regimens calculated by linking the dependent medication's dosing indications to those calculated for the primary medication in that user account or sub-account, "every other day" medication dosing regimens calculated by setting the dose times to each user's specified weekday and weekend wake times, weekday and weekend wake times plus an additional time interval, or weekday and weekend breakfast times, and alternating the daily dosing events, "once a week, once every two weeks, or once a month" medication dosing regimen calculations by enabling each user to select their preferred time and day the dose is to be taken and setting subsequent dose times on a weekly, bi-weekly, or monthly basis, and any other medication dosing regimen formula calculated using one or more schedule variables selected from each user's specified weekday and weekend wake times, weekday and weekend bed times, weekday and weekend breakfast times, weekday and weekend lunch times, and weekday and weekend dinner times, optional lead time variables for those schedule events, one or more dosage variables selected from the user-specific prescription medication data in each user account for each prescription medication or the dosage data specified in each user account for each over-the-counter medication, vitamin, supplement, or herbal medication, and optional user-specific variables from each user account including each child's, spouse's, or legal dependent's age, weight, and gender, (ix) the secondary database system generates user and time-specific medication dosing instructions for each dose of prescription or alternative medication including at least the dose time, user's name, prescription or alternative medication name, and number and type of units to be taken at that dose time based on the system-calculated user and time-specific medication dosing regimen for that user, time, and prescription or alternative medication, (x) the user interface and secondary database system enable each user to optionally enhance their child's, spouse's, or legal dependent's user-specific medication dosing instructions with a prescription or alternative medication image, Internet prescription or alternative medication link, Internet treatment link, advertisement, or logo based on user account selections, and (xi) the wireless messaging platform utilizes said user-specific medication dosing instructions in conjunction with user data in each child's, spouse's, or legal dependent's user account including the specified current time zone and wireless phone number or wireless device identifier to determine wireless message recipients and format, schedule, and transmit data-based messages containing user-specific medication dosing instructions over one or more networks to wireless carriers or wireless messaging gateways for wireless delivery to users including individuals, parents, legal guardians, children, spouses, legal dependents, or combinations thereof at system-determined medication dose times on their wireless phones, Smartphones, PDAs, wireless devices, or combinations thereof via SMS, EMS, MMS, WAP-Push, BREW, SIP, IM, email, or any combination thereof.

33. The system of claim 1 wherein user-specific prescription medication data uploaded into the secondary database system from at least one primary health care database or primary health care computer server can include one or more prescription medication images, Internet medication links, Internet treatment links, prescription pricing comparisons, advertisements, logos, audio files, video files, or combinations thereof, which are integrated with related data in user accounts and incorporated into user and time-specific medication dosing instructions for each medication based on user account selections opting for their incorporation.

34. The system of claim 1 wherein the user interface and secondary database system enable individuals to create user accounts and perform requisite user actions for their children, spouses, legal dependents, or combinations thereof, also defined as system users, and wherein user-specific prescription medication data uploaded into the secondary database system from at least one primary health care database or primary health care computer server can include one or more prescription medication images, Internet medication links, Internet treatment links, prescription pricing comparisons, advertisements, logos, audio files, video files, or combinations thereof, which are integrated with related data in each child's, spouse's, or legal dependent's user account and incorporated into user and time-specific medication dosing instructions for each medication based on user account selections opting for their incorporation.

35. The system of claim 1 wherein the user interface and secondary database enable each user to select at least one message format in their user account from the group consisting of SMS, EMS, MMS, SIP, IM, WAP-Push, BREW, and email, and wherein the wireless message platform utilizes said message format selections to format and transmit each user's data-based messages containing user and time-specific medication dosing instructions to each user via that selected message format.

36. The system of claim 1 wherein the user interface and secondary database enable each user to select one or more media types in their user account from the group consisting of text, images, multi-media, Internet links, audio, and video for the content incorporated into their user and time-specific medication dosing instructions, and wherein the secondary database system utilizes said media selections to incorporate content into the user and time-specific medication dosing instructions and related data-based messages which are transmitted to each particular user.

37. The system of claim 1 wherein the user interface and secondary database system enable users to create sub-accounts containing at least the name and wireless phone number or wireless device identifier of third party individuals, and wherein this data is made available to the wireless messaging platform to determine message recipients and format, schedule, and transmit copies of each user's data-based messages containing user and time-specific medication dosing instructions over one or more networks to wireless carriers or wireless messaging gateways for wireless delivery to said third party individuals on their wireless phones, Smartphones, PDAs, wireless devices, or combinations thereof via SMS, EMS, MMS, WAP-Push, BREW, SIP, IM, or email.

38. The system of claim 1 wherein the secondary database system or wireless messaging platform bill the wireless phone account, bank account, credit card, health insurance account, or other payment method specified in each user account for wireless messaging charges.

39. The system of claim 1 wherein the user interface and secondary database system enable individuals including parents and legal guardians to create user accounts and perform requisite user actions on behalf of their children, spouses, legal dependents, or combinations thereof, also defined as system users, and wherein the secondary database system or wireless messaging platform bill the wireless phone account, bank account, credit card, health insurance account, or other payment method specified in each user account for wireless messaging charges, including accounts for each child, spouse, or legal dependent and their parents or legal guardians.

40. The system of claim 1 wherein the secondary database system or wireless messaging platform incorporate a reply-to key into wireless messages or assign a handset key or short code to enable users to send reply messages to system-generated, data-based messages containing user and time-specific medication dosing instructions, wherein said reply messages indicate that a particular user (i) did take the specific dose of medication referenced in a particular user and time-specific medication dosing instruction, or (ii) did not take the specific dose of medication referenced in a particular user and time-specific medication dosing instruction, and wherein the wireless messaging platform receives and passes said data on to the secondary database system, which processes, stores, and transforms said data into a graphical or tabular format which each user can view in their user account via the user interface.

41. The system of claim 1 wherein (i) the secondary database system or wireless messaging platform incorporate a reply-to key into wireless messages or assign a handset key or short code to enable users to send reply messages to system-generated, data-based messages containing user and time-specific medication dosing instructions, (ii) said reply messages indicate that a particular user is having an emergency related to a specific dose of medication or a condition associated with that medication, (iii) said reply messages are processed by the wireless messaging platform and secondary database system and initiate a system-generated, data-based voice call, data-based message, or other notification containing one or more data items selected from the group consisting of each user's name, medication name, National Drug Code, unit dose, dosage form, route of administration, dose time, medical condition related to that medication, medical treatment related to that medication, and Global Positioning System (GPS) or Radio Frequency Identification (RFID) location-based information from each user's wireless phone, Smartphone, PDA, or wireless device to emergency medical services or emergency contacts entered or specified in each user account.

42. The system of claim 1 wherein the wireless messaging platform formats user and time-specific medication dosing instructions into data-based messages and transmits said data-based messages using one or more communications protocols over one or more networks to one or more wireless carriers or wireless messaging gateways, which employ at least one short message service center (SMSC), multi-media message service center (MMSC), Signaling System No. 7 (SS7) gateway, wireless network operations center, wireless interface, mobile switching center, media gateway, server, router, base station controller, or other wireless network infrastructure to route and deliver said wireless data-based messages to users at system-determined medication dose times on their wireless phones, Smartphones, PDAs, wireless devices, or combinations thereof via SMS, EMS, MMS, WAP-Push, BREW, IP, SIP, or email over one or more wireless networks selected from the group consisting of wireless Internet, wireless local area networks (WLAN), Session Initiation Protocol (SIP) networks, Worldwide Interoperability for Microwave Access (WiMAX), Signaling System No. 7 (SS7) networks, Advanced Mobile Phone System (AMPS), Code Division Multiple Access (CDMA), Time Division Multiple Access (TDMA), Global System for Mobile Communications (GSM), Personal Communications Service (PCS), General Packet Radio Service (GPRS), Enhanced Data Rates for GSM Evolution (EDGE), Universal Mobile Telecommunications System (UMTS), High Speed Download Packet Access (HSDPA), High Speed Uplink Packet Access (HSUPA), Second Generation Wireless Telephone Technology (2G), Third Generation Wireless Telephone Technology (3G), Fourth Generation Wireless Telephone Technology (4G), other wireless computer networks, other wireless communications networks, and combinations thereof.

43. The system of claim 1 wherein the user interface and secondary database system enable individuals including parents and legal guardians to create user accounts and perform user actions on behalf of their children, spouses, legal dependents, or combinations thereof, also defined as system users, and wherein the wireless messaging platform formats user and time-specific medication dosing instructions for said children, spouses, or legal dependents into data-based messages and transmits said data-based messages using one or more communications protocols over one or more networks to one or more wireless carriers or wireless messaging gateways, which employ at least one short message service center (SMSC), multi-media message service center (MMSC), Signaling System No. 7 (SS7) gateway, wireless network operations center, wireless interface, mobile switching center, media gateway, server, router, base station controller, or other wireless network infrastructure to route and deliver said wireless data-based messages to users, parents, legal guardians, children, spouses, legal dependents, or combinations thereof at system-determined medication dose times on their wireless phones, Smartphones, PDAs, wireless devices, or combinations thereof via SMS, EMS, MMS, WAP-Push, BREW, IP, SIP, or email over one or more wireless networks selected from the group consisting of wireless Internet, wireless local area networks (WLAN), Session Initiation Protocol (SIP) networks, Worldwide Interoperability for Microwave Access (WiMAX), Signaling System No. 7 (SS7) networks, Advanced Mobile Phone System (AMPS), Code Division Multiple Access (CDMA), Time Division Multiple Access (TDMA), Global System for Mobile Communications (GSM), Personal Communications Service (PCS), General Packet Radio Service (GPRS), Enhanced Data Rates for GSM Evolution (EDGE), Universal Mobile Telecommunications System (UMTS), High Speed Download Packet Access (HSDPA), High Speed Uplink Packet Access (HSUPA), Second Generation Wireless Telephone Technology (2G), Third Generation Wireless Telephone Technology (3G), Fourth Generation Wireless Telephone Technology (4G), other wireless computer networks, other wireless communications networks, and combinations thereof.

44. The system of claim 1 wherein the user interface, secondary database system, and wireless messaging platform comprise at least one Web, WAP, or mobile application accessible to users via a client/server network architecture, connected via at least one network and integrated with at least one primary health care database or primary health care computer server, and connected to wireless carriers or wireless messaging gateways via one or more networks.

45. The system of claim 1 wherein the secondary database system and at least one primary health care database comprise a single database system stored or hosted on at least one database server, connected via one or more networks and integrated with the user interface and wireless messaging platform.

46. The system of claim 1 wherein a primary health care database can comprise a legacy system, data warehouse, central database which aggregates branch account data, relational database, object database, real-time database, distributed database, database management system (DBMS), data processing system, mainframe database, client/server database, cloud database, online transaction processing system (OLTP) database, development database, test and staging database, live production database, data mart, database server, computer server, electronic store of user-specific prescription medication data, electronic store of non user-specific prescription medication data, electronic store of user-specific personal health records, or any combination thereof.

47. The system of claim 1 wherein the user interface, secondary database system, wireless messaging platform, and at least one primary health care database or primary health care computer server are connected via a distributed network architecture and integrated using one or more integration methods selected from the group consisting of extract, transfer, and load (ETL), client/server method, cloud method, Web Services, Simple Object Access Protocol (SOAP), Distributed Component Object Model (DCOM), ActiveX Data Objects (ADO), ADO.NET, Java Remote Method Invocation (RMI), XML-Remote Procedure Calls (RPC), Representational State Transfer (REST), application programming interfaces (API), system interfaces, system adapters, system brokers, Open Database Connectivity (ODBC), Java Database Connectivity (JDBC), Object Linking and Embedding Database (OLE DB), Perl Database Interface (Perl DBI), middleware, Object Request Brokers (ORB), Common Object Request Broker Architecture (CORBA), software bridges, enterprise service buses, enterprise information integration solutions, enterprise application integration solutions, service oriented architectures, customized integration methods, and combinations thereof.

48. The system of claim 1 wherein one or more application programs include processor-executable code loaded from memory which (i) encapsulate data including data items and procedural language/structural query language procedures, (ii) execute an application flow triggered by data or events entered or uploaded into user accounts, (iii) process and transform the data entered and uploaded into user accounts using conditional logic, (iv) perform user-specific calculations and configure user-specific system settings for each user based on data entered or uploaded into user accounts, and (v) execute and process system actions based on data, triggers, or settings in each user account.

49. The system of claim 1 wherein one or more application programs or algorithms perform system operations including (i) user account creation, (ii) securely verifying and processing user sign up and sign in data, (iii) organizing user accounts by user name, user number, account number, primary key, or other personal identifiers, (iv) initiating communication between the secondary database system and at least one primary health care database or primary health care computer server over one or more networks, (v) processing tags, commands, or transformations which enable data transfer between at least one primary health care database or primary health care computer server and the secondary database system, (vi) connecting to at least one primary health care database or primary health care computer server and utilizing one or more personal identifiers primary health care account identifiers, or combinations thereof from each user account to authenticate and authorize the upload of user-specific prescription medication data into each user account from at least one primary health care database or primary health care computer server, (vii) uploading user-specific prescription medication data from at least one primary health care database or primary health care computer server into user accounts in the secondary database system, (viii) transforming National Drug Codes, barcodes, or universal product codes into their underlying data components, (ix) enabling users to select medications from among all medications uploaded or added into user accounts for further system use based on user account selections, (x) configuring user-specific system settings for each user based on data entered, scanned in, or otherwise specified in each user account, (xi) integrating additional data into user accounts, (xii) creating optional, additional wireless recipients for each user by processing and incorporating additional contact information entered into user accounts, (xiii) calculating user and time-specific medication dosing regimens for medications in user accounts using at least one medication dosing regimen formula, one or more schedule variables selected from the schedule data each user is required to enter or specify to complete the user account set up algorithm including their weekday and weekend wake times, weekday and weekend bed times, weekday and weekend breakfast times, weekday and weekend lunch times, and weekday and weekend dinner times, and one or more dosage variables selected from the dosage data uploaded or added to each account with user-specific medication data including the prescribed medication dosage and number and type of units per dose including the unit dose, the volume of solution, or the number of dosage forms, (xiv) incorporating optional, additional content into user and time-specific medication dosing instructions including prescription medication images, Internet medication links, or Internet treatment links based on user account selections, (xv) generating user and time-specific medication dosing instructions for medications in user accounts based on the user and time-specific medication dosing regimens calculated for each user and medication, (xvi) formatting user and time-specific medication dosing instructions into data-based messages based on message formats specified by users in user accounts, (xvii) determining message recipients for the transmission of data-based messages containing user and time-specific medication dosing instructions including users, children, spouses, legal dependents, or additional recipients, (xviii) scheduling data-based messages containing user and time-specific medication dosing instructions for transmission over one or more networks to wireless carriers or wireless messaging gateways for wireless delivery to users at system-determined medication dose times, (xix) sorting and queuing message transmissions by at least one data item selected from the group consisting of current time, use's current time zone, dose time, and lead time to transmission, (xx) determining alphanumeric limitations associated with message formats, wireless phone displays, or wireless device displays and generating and transmitting concatenated messages for each data-based message that exceeds the alphanumeric limit, (xxi) transmitting data-based messages containing user and time-specific medication dosing instructions over one or more networks to wireless carriers or wireless messaging gateways or combinations thereof for wireless delivery to users at system-determined medication dose times on their wireless phones, Smartphones, PDAs, wireless devices, or combinations thereof, (xxii) billing user wireless phone accounts, bank accounts, credit cards, insurance company accounts, or other payment methods for wireless messaging charges, (xxiii) verifying message delivery or time of receipt for each data-based message delivered from a SMSC, MMSC, wireless carrier, wireless messaging gateway, or other wireless network infrastructure, and (xxiv) executing system actions based on data in user accounts.

50. An integrated prescription management and compliance system comprising:
at least one primary health care database containing user-specific prescription medication data for one or more individuals selected from the group consisting of one or more pharmacies, pharmacy benefit managers (PBM), health insurance companies, National Council for Prescription Drug Program (NCPDP) database providers, electronic health record (EHR) providers, and other primary health care databases containing user-specific prescription medication data for one or more individuals stored or hosted on at least one primary health care computer server and connected to one or more networks;
a mobile software application comprising a user interface, database, and one or more application programs and algorithms installed and stored on one or more user wireless phones, Smartphones, personal digital assistants (PDA), or wireless devices and connected to at least one primary health care database or primary health care computer server over one or more wireless and wire line networks that (i) enables one or more individuals to create user accounts via the user interface rendered on each respective user's wireless phone, Smartphone, PDA, or wireless device display, (ii) enables users to create additional user accounts and perform requisite user actions on behalf of their children, spouses, legal dependents, or combinations thereof via the user interface rendered on each user's wireless phone, Smartphone, PDA, or wireless device display, (iii) enables users to enter, select, scan in, or otherwise specify data in user accounts via the user interface, (iv) enables users to access, view, and modify data in user accounts via the user interface, (v) enables each user to access a user account set up algorithm via the user interface which requires each user to enter, scan in, or otherwise specify at least their schedule data and one or more personal identifiers, primary health care account identifiers, or combinations thereof in their user account to complete the algorithm, (vi) utilizes the personal identifiers, primary health care account identifiers, or combinations thereof specified in each user account as part of the user account set up algorithm to execute user authentication and authorization processes with at least one primary health care database or primary health care computer server and uploads, processes, and stores user-specific prescription medication data from at least one primary health care database or primary health care computer server into each user account, (vii) enables each user to select prescription medications for uploading or further system use from among prescription medications identified from each particular primary health care database source in each user account, (viii) enables each user to manually enter, scan in, modify, or otherwise specify data in their user account and combine this data with user-specific prescription medication data uploaded into their user account from at least one primary health care database or primary health care computer server, (ix) utilizes data entered, scanned in, or otherwise specified by each user as part of the user account set up algorithm to perform calculations for each user and configure user-specific system settings, (x) calculates a user and time-specific medication dosing regimen for each prescription medication selected in each user account using a medication dosing regimen formula, one or more schedule variables selected from the schedule data each user specifies in their user account as part of the user account set up algorithm, and one or more dosage variables selected from the user-specific prescription medication data uploaded, added, or modified in each user account for each prescription medication, (xi) generates user and time-specific medication dosing instructions for each dose of prescription medication based on the user and time-specific medication dosing regimen calculated by the system for that user and prescription medication, (xii) enables each user to optionally enhance their user and time-specific medication dosing instructions with a medication image, Internet medication link, Internet treatment link, advertisement, logo, or other additional content based on user account selections, (xiii) formats said user and time-specific medication dosing instructions into data-based messages containing at least the current dose time, medication name, and number and type of units to be taken at that dose time, and (xiv) schedules, opens, and displays said data-based messages at system-determined medication dose times on each user's wireless phone, Smartphone, PDA, or wireless device display.

51. The system of claim 50 wherein the mobile software application enables individuals including parents and legal guardians to create user accounts and perform user actions on behalf of their children, spouses, legal dependents, or combinations thereof, and wherein a user comprises (i) an individual who creates a user account, (ii) a child, spouse, or legal dependent for whom a user account is created, or (iii) an individual, parent, or legal guardian who creates a user account for their child, spouse, or legal dependent.

52. The system of claim 50 wherein data required to be entered, scanned in, or otherwise specified in each user account for completion of the user account set up algorithm includes at least (i) one or more personal identifiers, primary health care account identifiers, or combinations thereof selected from the group consisting of each user's name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, prescription medication barcodes, and universal product codes, and (ii) each user's schedule data including weekday and weekend wake times, weekday and weekend bed times, weekday and weekend breakfast times, weekday and weekend lunch times, and weekday and weekend dinner times.

53. The system of claim 50 wherein user-specific prescription medication data required to calculate user and time-specific medication dosing regimens and uploaded into each user account from at least one primary health care database or primary health care computer server or entered, scanned in, modified, or otherwise specified by each user in each user account via the user interface includes at least (i) a prescription medication identifier including the medication name, National Drug Code (NDC), prescription barcode, prescription medication barcode, or universal product code for each medication prescribed to each user, (ii) the prescribed number and type of units per dose including the unit dose, the volume of drug solution, or the number of dosage forms for each medication prescribed to each user, and (iii) the prescribed dosage for each medication prescribed to each user, wherein dosage comprises at least the prescribed dose and frequency and can also include duration, route of administration, sig codes, and other dosage data.

54. The system of claim 50 wherein user-specific prescription medication data uploaded into each user account from at least one primary health care database or primary health care computer server can include each user's first and last name, birth date, age, gender, weight, ethnicity, address, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, prescription medication identifiers including each medication's respective brand name, generic name, scientific name, National Drug Code, prescription number, prescription barcode, prescription medication barcode, and universal product code, prescription medication dosage data including each medication's unit dose, dosage, number and type of units per dose, volume of drug in solution, dosage form, routes of administration, sig codes, additional dosing indications, quantity of medication in terms of number of units, quantity of medication in terms of number of days of supply, substitutions made for the aforementioned data, generic drug substitutes, medication interaction warnings, dates dispensed, refill dates, prescription order dates, medication expiration dates, medication refill numbers, and indication of retail or mail order purchase for each medication prescribed to each user, prescription drug prices, prescription drug wholesale prices, generic drug prices, price comparisons, prescription medication images, Internet medication links, Internet treatment links, prescription pricing comparisons, advertisements, logos, prescribing physician names, prescribing physician identification numbers, prescribing physician addresses and telephone numbers, and medical conditions or medical treatments associated with each medication prescribed to each user.

55. The system of claim 50 wherein the mobile software application automatically updates the user-specific prescription medication data uploaded into each user account from each respective primary health care database or primary health care computer server and modifies each user and time-specific medication dosing regimen, user and time-specific medication dosing instruction, and related data-based messages containing user and time-specific dosing instructions to reflect any changes in each user's underlying user-specific prescription medication data stored in at least one primary health care database.

56. The system of claim 50 wherein data entered, scanned in, modified, or otherwise specified in each user account via the user interface can include each user's first and last name, birth date, weight, gender, ethnicity, country, address, language, social security number, email address, account username, account password, name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, prescription medication identifiers including each medication's respective brand name, scientific name, generic name, National Drug Code, prescription number, prescription barcode, prescription medication barcode, and universal product code, prescription medication dosage data including each medication's prescribed unit dose, dosage, number and type of units per dose, volume of drug in solution, dosage form, routes of administration, sig codes, additional dosing indications, quantity in terms of number of units, and quantity in terms of days of supply, medication order dates, medication expiration dates, dates medications are dispensed, refill dates, prescribing physician names, prescribing physician identification numbers, prescribing physician addresses and telephone numbers, alternative medications including over-the-counter medications, vitamins, supplements, and herbal medications and their respective brand names, scientific names, barcodes, universal product codes, unit doses, dosages, number and type of units per dose, volume of drug in solution, dosage forms, routes of administration, sig codes, additional dosing indications, quantity in terms of number units, and quantity in terms of number of days of supply for each alternative medication, medical conditions associated with each prescription or alternative medication, medical treatments associated with each prescription or alternative medication, prescription medications and related dosage data selected for further system use from among all prescription medications uploaded, scanned in, or entered into user accounts, alternative medications and related dosage data selected for further system use from among all alternative medications entered or scanned into user accounts, user-specific prescription medication data including prescription medication names, National Drug Codes, prescription numbers, prescription barcodes, prescription medication barcodes, universal product codes, dosages, unit doses, number and type of units per dose, volume of drug in solution, dosage forms, routes of administration, sig codes, additional dosing indications, quantity in terms of number units, and quantity in terms of number of days of supply for each prescription medication, weekday and weekend wake times, weekday and weekend bed times, weekday and weekend breakfast times, weekday and weekend lunch times, weekday and weekend dinner times, current time zone, wireless phone number, wireless device identifier, name of wireless carrier, wireless phone brand, wireless device brand, wireless handset model, wireless device model, bank account number, credit card number, billing address, preferred payment method, digital signature for electronic legal documents, emergency medical contact information including names and telephone numbers, selections to add medication images, Internet medication links, Internet treatment links, prescription pricing comparisons, advertisements, logos, audio files, or video files to user and time-specific medication dosing instructions, or combinations thereof.

57. The system of claim 50 wherein (i) the user account set up algorithm requires that each user enter or specify schedule data including their weekday and weekend wake times, weekday and weekend bed times, weekday and weekend breakfast times, weekday and weekend lunch times, and weekday and weekend dinner times into their user account via the user interface to complete the algorithm, (ii) the user account set up algorithm requires that each user enter, scan in, or otherwise specify one or more personal identifiers, primary health care account identifiers, or combinations thereof selected from the group consisting of their name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, prescription medication barcodes, and universal product codes into their user account to complete the algorithm, (iii) user-specific prescription medication data uploaded into each user account from at least one primary health care database/primary health care computer server or entered, scanned in, modified, or otherwise specified by each user in each user account includes one or more prescription medication identifiers selected from the group consisting of prescription medication brand names, prescription medication generic names, prescription medication scientific names, National Drug Codes, prescription numbers, prescription barcodes, and prescription medication barcodes, each medication's prescribed dosage, and each medication's prescribed number and type of units per dose, (iv) user-specific prescription medication data uploaded into each user account from at least one primary health care database/primary health care computer server or entered, scanned in, modified, or otherwise specified by each user in each user account via the user interface can include optional dosage data including routes of administration, sig codes, additional dosing indications, quantity of medication in number of units, quantity of medication in number of days of supply, prescription medication order dates, prescription medication refill dates, the dates prescription medications were dispensed, prescription medication images, Internet prescription medication links, Internet treatment links, and interaction warnings for each medication prescribed to each user, and (v) the mobile software application calculates a user and time-specific medication dosing regimen for each prescription medication selected in each user account using one or more schedule variables selected from the schedule data in each user account, one or more dosage variables selected from the user-specific prescription medication data in each user account including at least the prescribed dosage and prescribed number and type of units per dose for each prescription medication, and a medication dosing regimen formula selected from the group consisting of "once in the morning" or "once a day" medication dosing regimens calculated by setting the dose times to each user's specified weekday and weekend wake times, weekday and weekend wake times plus an additional time interval, or weekday and weekend breakfast times, "once before bed" or "once at night" medication dosing regimens calculated by setting the dose times to each user's specified weekday and weekend bed times, weekday and weekend bed times minus an additional time interval, or weekday and weekend dinner times, "dosing with meals" medication dosing regimens calculated by setting the dose times to each user's specified weekday and weekend breakfast, lunch, and dinner times or weekday and weekend breakfast, lunch, and dinner times plus or minus an additional time interval, "dosing before meals" medication dosing regimens calculated by setting the dose times to each user's specified weekday and weekend breakfast, lunch, and dinner times minus an additional time interval, "dosing after meals" medication dosing regimens calculated by setting the dose times to each user's specified weekday and weekend breakfast, lunch, and dinner times plus an additional time interval, "dosing 'n' times per day" medication dosing regimens calculated by setting the first dose to each user's specified weekday and weekend wake times, weekday and weekend wake times plus an additional time interval, or weekday and weekend breakfast times, setting the final dose to each user's specified weekday and weekend bed times, weekday and weekend bed times minus an additional time interval, or weekday and weekend dinner times, and calculating additional dose times by dividing the number of remaining hours in each user's weekday and weekend day by 'n–1' and setting additional dose times at each time interval other than the first or final dose times, "dosing every 'n' hours" medication dosing regimens calculated by starting the calculations and setting the first dose to each user's specified weekday and weekend wake times, weekday and weekend wake times plus an additional time interval, or weekday and weekend breakfast times, setting subsequent dose times every 'n' hours after each start time, and stopping the calculations at each user's specified weekday and weekend bed times or continuing the calculation throughout subsequent 24 hour periods, "medications prescribed to be taken with a dose of another medication" dosing regimens calculated by linking the dependent medication's dosing indications to those calculated for the primary medication in each user account, "every other day" medication dosings regimens calculated by setting the dose times to each user's specified weekday and weekend wake times, weekday and weekend wake times plus an additional time interval, or weekday and weekend breakfast times and alternating the daily dosing events, "once a week, once every two weeks, or once a month" medication dosing regimens calculated by enabling each user to select their preferred time and day the dose is to be taken and setting subsequent dose times on a weekly, bi-weekly, or monthly basis, and any other medication dosing regimen formula calculated using one or more schedule variables selected from the schedule data in each user account, optional lead time variables for those schedule events, one or more dosage variables selected from the user-specific prescription medication data in each user account, and optional user-specific variables from each user account including each user's age, weight, or gender.

58. The system of claim 50 wherein (i) the user account set up algorithm requires that each user enter or specify schedule data including their weekday and weekend wake times, weekday and weekend bed times, weekday and weekend breakfast times, weekday and weekend lunch times, and weekday and weekend dinner times into their user account to complete the algorithm, (ii) the user account set up algorithm requires that each user enter, scan in, or otherwise specify one or more personal identifiers, primary health care account identifiers, prescription medication identifiers, or combinations thereof selected from the group consisting of each user's name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, prescription medication barcodes, and universal product codes into their user account to complete the algorithm, (iii) the mobile software application utilizes said personal identifiers, primary health care account identifiers, prescription medication identifiers, or combinations thereof to authenticate each user and prescription medication against at least one primary health care database or primary health care computer server and authorize and upload user-specific prescription medication data for each identified prescription medication from said primary health care database or primary health care computer server into each user account, (iv) user-specific prescription medication data uploaded into each user account from at least one primary health care database/primary health care computer server or entered, scanned in, modified, or otherwise specified by each user in each user account includes one or more prescription medication identifiers selected from the group consisting of prescription medication brand names, prescription medication generic names, prescription medication scientific names, National Drug Codes, prescription numbers, prescription barcodes, prescription medication barcodes, and universal product codes, each medication's prescribed dosage, and each medication's prescribed number and type of units per dose, (v) user-specific prescription medication data uploaded into each user account from at least one primary health care database/primary health care computer server or entered, scanned in, modified, or otherwise specified by each user in each user account can include optional dosage data including routes of administration, sig codes, additional dosing indications, quantity of medication in number of units, quantity of medication in number of days of supply, prescription medication order dates, prescription medication refill dates, the dates prescription medications were dispensed, prescription medication images, Internet prescription medication links, Internet treatment links, and interaction warnings for each medication prescribed to each user, and (vi) the mobile software application calculates a user and time-specific medication dosing regimen for each prescription medication in each user account using one or more schedule variables selected from the schedule data in each user account, one or more dosage variables selected from the user-specific prescription medication data in each user account including at least the prescribed dosage and prescribed number and type of units per dose for each prescription medication, and a medication dosing regimen formula selected from the group consisting of "once in the morning" or "once a day" medication dosing regimens calculated by setting the dose times to each user's specified weekday and weekend wake times, weekday and weekend wake times plus an additional time interval, or weekday and weekend breakfast times, "once before bed" or "once at night" medication dosing regimens calculated by setting the dose times to each user's specified weekday and weekend bed times, weekday and weekend bed times minus an additional time interval, or weekday and weekend dinner times, "dosing with meals" medication dosing regimens calculated by setting the dose times to each user's specified weekday and weekend breakfast, lunch, and dinner times or weekday and weekend breakfast, lunch, and dinner times plus or minus an additional time interval, "dosing before meals" medication dosing regimens calculated by setting the dose times to each user's specified weekday and weekend breakfast, lunch, and dinner times minus an additional time interval, "dosing after meals" medication dosing regimens calculated by setting the dose times to each user's specified weekday and weekend breakfast, lunch, and dinner times plus an additional time interval, "dosing 'n' times per day" medication dosing regimens calculated by setting the first dose to each user's specified weekday and weekend wake times, weekday and weekend wake times plus an additional time interval, or weekday and weekend breakfast times, setting the final dose to each user's specified weekday and weekend bed times, weekday and weekend bed times minus an additional time interval, or weekday and weekend dinner times, and calculating additional dose times by dividing the number of remaining hours in each user's weekday and weekend day by 'n−1' and setting additional dose times at each time interval other than the first or final dose times, "dosing every 'n' hours" medication dosing regimens calculated by starting the calculations and setting the first dose to each user's specified weekday and weekend wake times, weekday and weekend wake times plus an additional time interval, or weekday and weekend breakfast times, setting subsequent dose times every 'n' hours after each start time, and stopping the calculations at each user's specified weekday and weekend bed times or continuing the calculation throughout subsequent 24 hour periods, "medications prescribed to be taken with a dose of another medication" dosing regimens calculated by linking the dependent medication's dosing indications to those calculated for the primary medication in each user account, "every other day" medication dosings regimens calculated by setting the dose times to each user's specified weekday and weekend wake times, weekday and weekend wake times plus an additional time interval, or weekday and weekend breakfast times and alternating the daily dosing events, "once a week, once every two weeks, or once a month" medication dosing regimens calculated by enabling each user to select their preferred time and day the dose is to be taken and setting subsequent dose times on a weekly, bi-weekly, or monthly basis, and any other medication dosing regimen formula calculated using one or more schedule variables selected from the schedule data in each user account, optional lead time variables for those schedule events, one or more dosage variables selected from the user-specific prescription medication data in each user account, and optional user-specific variables from each user account including each user's age, weight, or gender.

59. The system of claim 50 wherein (i) the user account set up algorithm requires that each user enter or specify schedule data including their weekday and weekend wake times, weekday and weekend bed times, weekday and weekend breakfast times, weekday and weekend lunch times, and weekday and weekend dinner times into their user account to complete the algorithm, (ii) the user account set up algorithm requires that each user enter, scan in, or otherwise specify one or more personal identifiers, primary health care account identifiers, or combinations thereof selected from the group consisting of their name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, prescription medication barcodes, and universal product codes into their user account to complete the algorithm, (iii) user-specific prescription medication data uploaded into each user account from at least one primary health care database/primary health care computer server or entered, scanned in, modified, or otherwise specified by each user in each user account includes one or more prescription medication identifiers selected from the group consisting of prescription medication brand names, prescription medication generic names, prescription medication scientific names, National Drug Codes, prescription numbers, prescription barcodes, and prescription medication barcodes, each medication's prescribed dosage, and each medication's prescribed number and type of units per dose, (iv) user-specific prescription medication data uploaded into each user account from at least one primary health care database/primary health care computer server or entered, scanned in, modified, or otherwise specified by each user in each user account can include optional dosage data including routes of administration, sig codes, additional dosing indications, quantity of medication in number of units, quantity of medication in number of days of supply, prescription medication order dates, prescription medication refill dates, the dates prescription medications were dispensed, prescription medication images, Internet prescription medication links, Internet treatment links, and interaction warnings for each medication prescribed to each user, (v) the mobile software application enables each user to enter or otherwise specify additional medications and related dosage data into their user account including one or more over-the-counter medications, vitamins, supplements, herbal medications and their corresponding names, dosages, routes of administration, and number and type of units per dose, (vi) the mobile software application enables each user to select prescription medications, over-the-counter medications, vitamins, supplements, and herbal medications in each user account for further system use based on user account selections, (vii) the mobile software application calculates a user and time-specific medication dosing regimen for each prescription medication, over-the-counter medication, vitamin, supplement, or herbal medication selected in each user account using one or more schedule variables selected from the schedule data in each user account, one or more dosage variables selected from the user-specific prescription medication data in each user account for each prescription medication or the dosage data entered, selected, or otherwise specified by each user for each over-the-counter medication, vitamin, supplement, or herbal medication in each user account including at least the dosage and number and type of units per dose, and a medication dosing regimen formula selected from the group consisting of "once in the morning" or "once a day" medication dosing regimens calculated by setting the dose times to each user's specified weekday and weekend wake times, weekday and weekend wake times plus an additional time interval, or weekday and weekend breakfast times, "once before bed" or "once at night" medication dosing regimens calculated by setting the dose times to each user's specified weekday and weekend bed times, weekday and weekend bed times minus an additional time interval, or weekday and weekend dinner times, "dosing with meals" medication dosing regimens calculated by setting the dose times to each user's specified weekday and weekend breakfast, lunch, and dinner times or weekday and weekend breakfast, lunch, and dinner times plus or minus an additional time interval, "dosing before meals" medication dosing regimens calculated by setting the dose times to each user's specified weekday and weekend breakfast, lunch, and dinner times minus an additional time interval, "dosing after meals" medication dosing regimens calculated by setting the dose times to each user's specified weekday and weekend breakfast, lunch, and dinner times plus an additional time interval, "dosing 'n' times per day" medication dosing regimens calculated by setting the first dose to each user's specified weekday and weekend wake times, weekday and weekend wake times plus an additional time interval, or weekday and weekend breakfast times, setting the final dose to each user's specified weekday and weekend bed times, weekday and weekend bed times minus an additional time interval, or weekday and weekend dinner times, and calculating additional dose times by dividing the number of remaining hours in each user's weekday and weekend day by 'n−1' and setting additional dose times at each time interval other than the first or final dose times, "dosing every 'n' hours" medication dosing regimens calculated by starting the calculations and setting the first dose time to each user's specified weekday and weekend wake times, weekday and weekend wake times plus an additional time interval, or weekday and weekend breakfast times, setting subsequent dose times every 'n' hours after each start time, and stopping the calculation at each user's specified weekday and weekend bed times or continuing the calculation throughout subsequent 24 hour periods, "medications prescribed to be taken with a dose of another medication" dosing regimens calculated by linking the dependent medication's dosing indications to those calculated for the primary medication in that user account, "every other day" medication dosing regimens calculated by setting the dose times to each user's specified weekday and weekend wake times, weekday and weekend wake times plus an additional time interval, or weekday and weekend breakfast times, and alternating the daily dosing events, "once a week, once every two weeks, or once a month" medication dosing regimens calculated by enabling each user to select their preferred time and day the dose is to be taken and setting subsequent dose times on a weekly, bi-weekly, or monthly basis, and any other medication dosing regimen formula calculated using one or more schedule variables selected from the schedule data in each user account, optional lead time variables for those schedule events, one or more dosage variables selected from the user-specific prescription medication data in each user account for each prescription medication or the dosage data specified in each user account for each over-the-counter medication, vitamin, supplement, or herbal medication including at least a dosage and number and type of units per dose, and optional user-specific variables from each user account including each user's age, weight, and gender, (viii) the mobile software application generates user and time-specific medication dosing instructions for each dose of selected prescription medication, over-the-counter medication, vitamin, supplement, or herbal medication including at least the dose time, medication name, and number and type of units to be taken at that dose time based on the medication dosing regimen calculated for that user, day, and prescription medication, over-the-counter medication, vitamin, supplement, or herbal medication, (ix) the mobile software application enables each user to optionally enhance their user and time-specific medication dosing instructions with a medication image, Internet medication link, or Internet treatment link based on user account selections, (x) the mobile software application formats said user and time-specific medication dosing instructions into data-based messages containing at least the current dose time, number and type of units to be taken at that dose time, and prescription medication, over-the-counter medication, vitamin, supplement, or herbal medication name, and (xi) the mobile software application schedules, opens, and displays said data-based messages at system-determined medication dose times on each user's wireless phone, Smartphone, PDA, or wireless device display.

60. The system of claim 50 wherein (i) the user account set up algorithm requires that each user enter or specify schedule data including their weekday and weekend wake times, weekday and weekend bed times, weekday and weekend breakfast times, weekday and weekend lunch times, and weekday and weekend dinner times into their user account to complete the algorithm, (ii) the user account set up algorithm requires that each user enter, scan in, or otherwise specify one or more personal identifiers, primary health care account identifiers, or combinations thereof selected from the group consisting of their name, address, date of birth, social security number, personal identification numbers, personal identification data, user identification barcodes, pharmacy account identification numbers, pharmacy account identification data, pharmacy prescription numbers, pharmacy identification numbers, PBM account identification numbers, PBM policy numbers, PBM account identification data, health insurance account identification numbers, health insurance policy numbers, health insurance account identification data, NCPDP account identification numbers, NCPDP account identification data, EHR account identification numbers, EHR account identification data, other primary health care account identification numbers, other primary health care account identification data, National Drug Codes, prescription barcodes, and prescription medication barcodes into their user account to complete the algorithm, (iii) user-specific prescription medication data uploaded into each user account from at least one primary health care database or primary health care computer server includes one or more prescription medication identifiers selected from the group consisting of prescription medication brand names, prescription medication generic names, prescription medication scientific names, National Drug Codes, prescription numbers, prescription barcodes, and prescription medication barcodes, each medication's prescribed dosage, and each medication's prescribed number and type of units per dose, (iv) user-specific prescription medication data uploaded into each user account from at least one primary health care database or primary health care computer server can include optional dosage data including routes of administration, sig codes, additional dosing indications, quantity of medication in number of units, quantity of medication in number of days of supply, prescription medication order dates, prescription medication refill dates, interaction warnings, and the dates prescription medications were dispensed for each medication prescribed to each user, (v) the mobile software application uploads non user-specific prescription medication data which can include prescription medication brand names, prescription medication generic names, prescription medication scientific names, National Drug Codes, medication barcodes, universal product codes, prescription medication images, Internet prescription medication links, Internet treatment links, and each medication's indicated unit doses, dosage forms, routes of administration, volume of drug in solution, dosages, brand drug price, generic drug price, wholesale drug price, price comparisons, generic drug substitutes, and interaction warnings into the mobile software application database, (vi) the mobile software application uploads alternative medication data which can include over-the-counter medications, vitamins, supplements, and herbal medications and their corresponding names, barcodes, universal product codes, unit doses, dosage forms, volume of drug in solution, dosages, images, and routes of administration into the mobile software application database, (vii) the mobile software application enables each user to select, add, or modify non user-specific prescription medication data, over-the-counter medication data, vitamin data, supplement data, herbal medication data, or combinations thereof from the mobile software application database into their user account including one or more prescription medications, over-the-counter medications, vitamins, supplements, or herbal medications and their corresponding names, routes of administration, dosages, number and type of units per dose, and optional additional dosage data, (viii) the mobile software application enables each user to select prescription medications, over-the-counter medications, vitamins, supplements, and herbal medications in their user account for further system use based on user account selections, (ix) the mobile software application calculates a user and time-specific medication dosing regimen for each prescription medication, over-the-counter medication, vitamin, supplement, or herbal medication selected in each user account using one or more schedule variables selected from the schedule data in each user account, one or more dosage variables selected from the user-specific prescription medication data in each user account for each prescription medication or the dosage data entered, selected, or otherwise specified by each user for each over-the-counter medication, vitamin, supplement, or herbal medication in each user account including at least the dosage and number and type of units per dose, and a medication dosing regimen formula selected from the group consisting of "once in the morning" or "once a day" medication dosing regimens calculated by setting the dose times to each user's specified weekday and weekend wake times, weekday and weekend wake times plus an additional time interval, or weekday and weekend breakfast times, "once before bed" or "once at night" medication dosing regimens calculated by setting the dose times to each user's specified weekday and weekend bed times, weekday and weekend bed times minus an additional time interval, or weekday and weekend dinner times, "dosing with meals" medication dosing regimens calculated by setting the dose times to each user's specified weekday and weekend breakfast, lunch, and dinner times or weekday and weekend breakfast, lunch, and dinner times plus or minus an additional time interval, "dosing before meals" medication dosing regimens calculated by setting the dose times to each user's specified weekday and weekend breakfast, lunch, and dinner times minus an additional time interval, "dosing after meals" medication dosing regimens calculated by setting the dose times to each user's specified weekday and weekend breakfast, lunch, and dinner times plus an additional time interval, "dosing 'n' times per day" medication dosing regimens calculated by setting the first dose to each user's specified weekday and weekend wake times, weekday and weekend wake times plus an additional time interval, or weekday and weekend breakfast times, setting the final dose to each user's specified weekday and weekend bed times, weekday and weekend bed times minus an additional time interval, or weekday and weekend dinner times, and calculating additional dose times by dividing the number of remaining hours in each user's weekday and weekend day by 'n−1' and setting additional dose times at each time interval other than the first or final dose times, "dosing every 'n' hours" medication dosing regimens calculated by starting the calculations and setting the first dose time to each user's specified weekday and weekend wake times, weekday and weekend wake times plus an additional time interval, or weekday and weekend breakfast times, setting subsequent dose times every 'n' hours after each start time, and stopping the calculation at each user's specified weekday and weekend bed times or continuing the calculation throughout subsequent 24 hour periods, "medications prescribed to be taken with a dose of another medication" dosing regimens calculated by linking the dependent medication's dosing indications to those calculated for the primary medication in that user account, "every other day" medication dosing regimens calculated by setting the dose times to each user's specified weekday and weekend wake times, weekday and weekend wake times plus an additional time interval, or weekday and weekend breakfast times, and alternating the daily dosing events, "once a week, once every two weeks, or once a month" medication dosing regimens calculated by enabling each user to select their preferred time and day the dose is to be taken and setting subsequent dose times on a weekly, bi-weekly, or monthly basis, and any other medication dosing regimen formula calculated using one or more schedule variables selected from the schedule data in each user account, optional lead time variables for those schedule events, one or more dosage variables selected from the user-specific prescription medication data in each user account for each prescription medication or the dosage data specified in each user account for each over-the-counter medication, vitamin, supplement, or herbal medication, and optional user-specific variables from each user account including each user's age, weight, and gender, (x) the mobile software application generates user and time-specific medication dosing instructions for each dose of selected prescription medication, over-the-counter medication, vitamin, supplement, or herbal medication including at least the dose time, medication name, and number and type of units to be taken at that dose time, based on the medication dosing regimen calculated for that user, day, and prescription medication, over-the-counter medication, vitamin, supplement, or herbal medication, (xi) the mobile software application enables each user to optionally enhance their user and time-specific medication dosing instructions with a medication image, Internet medication link, or Internet treatment link based on user account selections made via the user interface, (xii) the mobile software application formats said user and time-specific medication dosing instructions into data-based messages containing at least the current dose time, prescription medication, over-the-counter medication, vitamin, supplement, or herbal medication name, and number and type of units to be taken at that dose time, and (xiii) the mobile software application schedules, opens, and displays said data-based messages at system-determined medication dose times on each user's wireless phone, Smartphone, PDA, or wireless device display.

61. The system of claim 50 wherein the mobile software application enables each user to select a media format for their data-based messages containing user-specific medication dosing instructions including at least one media format selected from the group consisting of text, images, multimedia, audio, video, and Internet links.

62. The system of claim 50 wherein the mobile software application incorporates a reply key into data-based messages containing user and time-specific medication dosing instructions to enable users to select a reply indicating that a particular user (i) did take the specific dose of medication referenced in a particular user and time-specific medication dosing instruction, or (ii) did not take the specific dose of medication referenced in a particular user and time-specific medication dosing instruction, and wherein the mobile software application receives, processes, stores, and transforms said data into a graphical or tabular format which each user can view in their user account.

63. The system of claim 50 wherein a primary health care database can comprise a legacy system, data warehouse, central database which aggregates branch account data, relational database, object database, real-time database, distributed database, database management system (DBMS), data processing system, mainframe database, client/server database, cloud database, online transaction processing system (OLTP) database, development database, test and staging database, live production database, data mart, database server, computer server, electronic store of user-specific prescription medication data, electronic store of non user-specific prescription medication data, electronic store of user-specific personal health records, or any combination thereof.

64. The system of claim 50 wherein one or more application programs or algorithms perform system operations including (i) user account creation, (ii) securely verifying and processing user sign up and sign in information, (iii) initiating communication between the mobile software application and at least one primary health care database or primary health care computer server over one or more networks, (iv) processing tags, commands, or transformations which enable data transfer between at least one primary health care database or primary health care computer server and the mobile software application, (v) connecting to at least one primary health care database or primary health care computer server and authenticating and authorizing user-specific prescription medication data uploads from at least one primary health care database or primary health care computer server utilizing one or more personal identifiers, primary health care account identifiers, or combinations thereof specified in each user account, (vi) uploading user-specific prescription medication data from at least one primary health care database or primary health care computer server into the mobile software application, (vii) transforming National Drug Codes, barcodes, or universal product codes into their underlying data components, (viii) enabling users to select medications from among all medications uploaded or added into user accounts for further system use based on user account selections, (ix) configuring user-specific system settings for each user based on data entered or otherwise specified in each user account via, (x) adding and integrating additional data into user accounts, (xi) calculating user and time-specific medication dosing regimens for medications in user accounts using at least one medication dosing regimen formula, one or more schedule variables selected from each user's weekday and weekend wake times, weekday and weekend bed times, weekday and weekend breakfast times, weekday and weekend lunch times, and weekday and weekend diner times, and one or more dosage variables selected from the dosage data uploaded or added to each account for each medication including the prescribed medication dosage and number and type of units per dose including unit dose, volume of solution, or number of dosage forms, (xii) incorporating optional, additional content into user and time-specific medication dosing instructions including prescription medication images, Internet medication links, Internet treatment links, advertisements, or logos based on user account selections, (xiii) generating user and time-specific medication dosing instructions for medications in user accounts based on the user and time-specific medication dosing regimens calculated for each user and medication, (xiv) formatting user and time-specific medication dosing instructions into data-based messages based on message formats specified in each user account, and (xv) scheduling data-based messages containing user and time-specific medication dosing instructions for display to users at system-determined medication dose times.

* * * * *